(12) United States Patent
Saadat et al.

(10) Patent No.: US 8,235,985 B2
(45) Date of Patent: Aug. 7, 2012

(54) VISUALIZATION AND ABLATION SYSTEM VARIATIONS

(75) Inventors: Vahid Saadat, Atherton, CA (US);
Ruey-Feng Peh, Mountain View, CA (US); Zachary J. Malchano, San Francisco, CA (US); Chris A. Rothe, San Mateo, CA (US)

(73) Assignee: Voyage Medical, Inc., Redwood City, CA (US)

( * ) Notice: Subject to any disclaimer, the term of this patent is extended or adjusted under 35 U.S.C. 154(b) by 909 days.

(21) Appl. No.: 12/209,057

(22) Filed: Sep. 11, 2008

(65) Prior Publication Data
US 2009/0076498 A1    Mar. 19, 2009

Related U.S. Application Data

(63) Continuation-in-part of application No. 12/201,811, filed on Aug. 29, 2008.

(60) Provisional application No. 60/971,462, filed on Sep. 11, 2007, provisional application No. 60/969,511, filed on Aug. 31, 2007.

(51) Int. Cl.
*A61B 18/18* (2006.01)

(52) U.S. Cl. .......................................................... 606/41

(58) Field of Classification Search ............... 606/34–45, 606/151, 108; 604/96.01, 104–109
See application file for complete search history.

(56) References Cited

U.S. PATENT DOCUMENTS

| | | | |
|---|---|---|---|
| 623,022 A | 4/1899 | Johnson | |
| 2,305,462 A | 12/1942 | Wolf | |
| 2,453,862 A | 11/1948 | Peter | |
| 3,874,388 A | 4/1975 | King et al. | |
| 4,175,545 A | 11/1979 | Termanini | |
| 4,326,529 A | 4/1982 | Doss et al. | |
| 4,445,892 A | 5/1984 | Hussein et al. | |
| 4,470,407 A | 9/1984 | Hussein et al. | |
| 4,517,976 A | 5/1985 | Murakoshi et al. | |
| 4,569,335 A | 2/1986 | Tsuno | |
| 4,576,146 A | 3/1986 | Kawazoe et al. | |
| 4,615,333 A | 10/1986 | Taguchi | |
| 4,619,247 A | 10/1986 | Inoue et al. | |
| 4,676,258 A | 6/1987 | Inokuchi et al. | |
| 4,681,093 A | 7/1987 | Ono et al. | |
| 4,709,698 A | 12/1987 | Johnston et al. | |
| 4,710,192 A | 12/1987 | Liotta et al. | |
| 4,727,418 A | 2/1988 | Kato et al. | |

(Continued)

FOREIGN PATENT DOCUMENTS

DE        10028155 A1    12/2000

(Continued)

OTHER PUBLICATIONS

U.S. Appl. No. 11/259,498, filed Oct. 25, 2005 in the name of Saadat, Notice of Allowance mailed Nov. 15, 2010.

(Continued)

*Primary Examiner* — Christopher D Koharski
(74) *Attorney, Agent, or Firm* — Levine Bagade Han LLP

(57) ABSTRACT

Visualization and ablation system variations are described which utilize various tissue ablation arrangements. Such assemblies are configured to facilitate the application of bipolar energy delivery, such as RF ablation, to an underlying target tissue for treatment in a controlled manner while directly visualizing the tissue during the bipolar ablation process.

15 Claims, 35 Drawing Sheets

U.S. PATENT DOCUMENTS

| | | |
|---|---|---|
| 4,784,133 A | 11/1988 | Mackin |
| 4,848,323 A | 7/1989 | Marijnissen et al. |
| 4,911,148 A | 3/1990 | Sosnowski et al. |
| 4,914,521 A | 4/1990 | Adair |
| 4,943,290 A | 7/1990 | Rexroth et al. |
| 4,950,285 A | 8/1990 | Wilk |
| 4,957,484 A | 9/1990 | Murtfeldt |
| 4,961,738 A | 10/1990 | Mackin |
| 4,976,710 A | 12/1990 | Mackin |
| 4,991,578 A | 2/1991 | Cohen |
| 4,994,069 A | 2/1991 | Ritchart et al. |
| 4,998,916 A | 3/1991 | Hammerslag et al. |
| 4,998,972 A | 3/1991 | Chin et al. |
| 5,047,028 A | 9/1991 | Qian |
| 5,057,106 A | 10/1991 | Kasevich et al. |
| 5,090,959 A | 2/1992 | Samson et al. |
| 5,123,428 A | 6/1992 | Schwarz |
| RE34,002 E | 7/1992 | Adair |
| 5,156,141 A | 10/1992 | Krebs et al. |
| 5,171,259 A | 12/1992 | Inoue |
| 5,281,238 A | 1/1994 | Chin et al. |
| 5,282,827 A | 2/1994 | Kensey et al. |
| 5,306,234 A | 4/1994 | Johnson |
| 5,313,943 A | 5/1994 | Houser et al. |
| 5,330,496 A | 7/1994 | Alferness |
| 5,334,159 A | 8/1994 | Turkel |
| 5,334,193 A | 8/1994 | Nardella |
| 5,336,252 A | 8/1994 | Cohen |
| 5,339,800 A | 8/1994 | Wilta et al. |
| 5,348,554 A | 9/1994 | Imran et al. |
| 5,353,792 A | 10/1994 | Lubbers et al. |
| 5,370,647 A | 12/1994 | Graber et al. |
| 5,373,840 A | 12/1994 | Knighton |
| 5,375,612 A | 12/1994 | Cottenceau et al. |
| 5,385,148 A | 1/1995 | Lesh et al. |
| 5,403,326 A | 4/1995 | Harrison et al. |
| 5,405,376 A | 4/1995 | Mulier et al. |
| 5,421,338 A | 6/1995 | Crowley et al. |
| 5,431,649 A | 7/1995 | Mulier et al. |
| 5,453,785 A | 9/1995 | Lenhardt et al. |
| 5,462,521 A | 10/1995 | Brucker et al. |
| 5,471,515 A | 11/1995 | Fossum et al. |
| 5,498,230 A | 3/1996 | Adair |
| 5,505,730 A | 4/1996 | Edwards |
| 5,515,853 A | 5/1996 | Smith et al. |
| 5,527,338 A | 6/1996 | Purdy |
| 5,549,603 A | 8/1996 | Feiring |
| 5,558,619 A | 9/1996 | Kami et al. |
| 5,571,088 A | 11/1996 | Lennox et al. |
| 5,575,756 A | 11/1996 | Karasawa et al. |
| 5,575,810 A | 11/1996 | Swanson et al. |
| 5,584,872 A | 12/1996 | LaFontaine et al. |
| 5,591,119 A | 1/1997 | Adair |
| 5,593,422 A | 1/1997 | Muijs Van de Moer et al. |
| 5,593,424 A | 1/1997 | Northrup, III |
| 5,672,153 A | 9/1997 | Lax et al. |
| 5,676,693 A | 10/1997 | LaFontaine |
| 5,681,308 A | 10/1997 | Edwards et al. |
| 5,695,448 A | 12/1997 | Kimura et al. |
| 5,697,281 A | 12/1997 | Eggers et al. |
| 5,697,882 A | 12/1997 | Eggers et al. |
| 5,709,224 A | 1/1998 | Behl et al. |
| 5,713,907 A | 2/1998 | Hogendijk et al. |
| 5,713,946 A | 2/1998 | Ben-Haim |
| 5,716,321 A | 2/1998 | Kerin et al. |
| 5,722,403 A | 3/1998 | McGee et al. |
| 5,725,523 A | 3/1998 | Mueller |
| 5,746,747 A | 5/1998 | McKeating |
| 5,749,846 A | 5/1998 | Edwards et al. |
| 5,749,890 A | 5/1998 | Shaknovich |
| 5,754,313 A | 5/1998 | Pelchy et al. |
| 5,766,137 A | 6/1998 | Omata |
| 5,769,846 A | 6/1998 | Edwards et al. |
| 5,792,045 A | 8/1998 | Adair |
| 5,797,903 A | 8/1998 | Swanson et al. |
| 5,823,947 A | 10/1998 | Yoon et al. |
| 5,827,268 A | 10/1998 | Laufer |
| 5,829,447 A | 11/1998 | Stevens et al. |
| 5,842,973 A | 12/1998 | Bullard |
| 5,843,118 A | 12/1998 | Sepetka et al. |
| 5,848,969 A | 12/1998 | Panescu et al. |
| 5,860,974 A | 1/1999 | Abele |
| 5,860,991 A | 1/1999 | Klein et al. |
| 5,865,791 A | 2/1999 | Whayne et al. |
| 5,873,815 A | 2/1999 | Kerin et al. |
| 5,879,366 A | 3/1999 | Shaw et al. |
| 5,895,417 A | 4/1999 | Pomeranz et al. |
| 5,897,487 A | 4/1999 | Ouchi |
| 5,897,553 A | 4/1999 | Mulier et al. |
| 5,902,328 A | 5/1999 | LaFontaine et al. |
| 5,904,651 A | 5/1999 | Swanson et al. |
| 5,908,445 A | 6/1999 | Whayne et al. |
| 5,925,038 A | 7/1999 | Panescu et al. |
| 5,928,250 A | 7/1999 | Koike et al. |
| 5,929,901 A | 7/1999 | Adair et al. |
| 5,941,845 A | 8/1999 | Tu et al. |
| 5,944,690 A | 8/1999 | Falwell et al. |
| 5,964,755 A | 10/1999 | Edwards |
| 5,968,053 A | 10/1999 | Revelas |
| 5,971,983 A | 10/1999 | Lesh |
| 5,986,693 A | 11/1999 | Adair et al. |
| 5,997,571 A | 12/1999 | Farr et al. |
| 6,004,269 A | 12/1999 | Crowley et al. |
| 6,012,457 A | 1/2000 | Lesh |
| 6,024,740 A | 2/2000 | Lesh et al. |
| 6,027,501 A | 2/2000 | Goble et al. |
| 6,036,685 A | 3/2000 | Mueller |
| 6,043,839 A | 3/2000 | Adair et al. |
| 6,047,218 A | 4/2000 | Whayne et al. |
| 6,063,077 A | 5/2000 | Schaer |
| 6,063,081 A | 5/2000 | Mulier et al. |
| 6,068,653 A | 5/2000 | LaFontaine |
| 6,071,279 A | 6/2000 | Whayne et al. |
| 6,071,302 A | 6/2000 | Sinofsky et al. |
| 6,081,740 A | 6/2000 | Gombrich et al. |
| 6,086,528 A | 7/2000 | Adair |
| 6,086,534 A | 7/2000 | Kesten |
| 6,099,498 A | 8/2000 | Addis |
| 6,099,514 A | 8/2000 | Sharkey et al. |
| 6,102,905 A | 8/2000 | Baxter et al. |
| 6,112,123 A | 8/2000 | Kelleher et al. |
| 6,115,626 A | 9/2000 | Whayne et al. |
| 6,123,703 A | 9/2000 | Tu et al. |
| 6,123,718 A | 9/2000 | Tu et al. |
| 6,129,724 A | 10/2000 | Fleischman et al. |
| 6,139,508 A | 10/2000 | Simpson et al. |
| 6,142,993 A | 11/2000 | Whayne et al. |
| 6,152,144 A | 11/2000 | Lesh et al. |
| 6,156,350 A | 12/2000 | Constantz |
| 6,159,203 A | 12/2000 | Sinofsky |
| 6,161,543 A | 12/2000 | Cox et al. |
| 6,164,283 A | 12/2000 | Lesh |
| 6,167,297 A | 12/2000 | Benaron |
| 6,168,591 B1 | 1/2001 | Sinofsky |
| 6,168,594 B1 | 1/2001 | LaFontaine et al. |
| 6,174,307 B1 | 1/2001 | Daniel et al. |
| 6,178,346 B1 | 1/2001 | Amundson et al. |
| 6,190,381 B1 | 2/2001 | Olsen et al. |
| 6,211,904 B1 | 4/2001 | Adair et al. |
| 6,224,553 B1 | 5/2001 | Nevo |
| 6,231,561 B1 | 5/2001 | Frazier et al. |
| 6,235,044 B1 | 5/2001 | Root et al. |
| 6,237,605 B1 | 5/2001 | Vaska et al. |
| 6,238,393 B1 | 5/2001 | Mulier et al. |
| 6,240,312 B1 | 5/2001 | Alfano et al. |
| 6,254,598 B1 | 7/2001 | Edwards et al. |
| 6,258,083 B1 | 7/2001 | Daniel et al. |
| 6,263,224 B1 | 7/2001 | West |
| 6,270,492 B1 | 8/2001 | Sinofsky |
| 6,275,255 B1 | 8/2001 | Adair et al. |
| 6,290,689 B1 | 9/2001 | Delaney et al. |
| 6,306,081 B1 | 10/2001 | Ishikawa et al. |
| 6,310,642 B1 | 10/2001 | Adair et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,777 B1 | 11/2001 | Comben |

| Patent | Date | Inventor |
|---|---|---|
| 6,315,778 B1 | 11/2001 | Gambale et al. |
| 6,322,536 B1 | 11/2001 | Rosengart et al. |
| 6,325,797 B1 | 12/2001 | Stewart et al. |
| 6,328,727 B1 | 12/2001 | Frazier et al. |
| 6,358,247 B1 | 3/2002 | Altman et al. |
| 6,358,248 B1 | 3/2002 | Mulier et al. |
| 6,375,654 B1 | 4/2002 | McIntyre |
| 6,379,345 B1 | 4/2002 | Constantz |
| 6,385,476 B1 | 5/2002 | Osadchy et al. |
| 6,387,043 B1 | 5/2002 | Yoon |
| 6,387,071 B1 | 5/2002 | Constantz |
| 6,394,096 B1 | 5/2002 | Constantz |
| 6,396,873 B1 | 5/2002 | Goldstein et al. |
| 6,398,780 B1 | 6/2002 | Farley et al. |
| 6,401,719 B1 | 6/2002 | Farley et al. |
| 6,409,722 B1 | 6/2002 | Hoey et al. |
| 6,416,511 B1 | 7/2002 | Lesh et al. |
| 6,419,669 B1 | 7/2002 | Frazier et al. |
| 6,423,051 B1 | 7/2002 | Kaplan et al. |
| 6,423,055 B1 | 7/2002 | Farr et al. |
| 6,423,058 B1 | 7/2002 | Edwards et al. |
| 6,428,536 B2 | 8/2002 | Panescu et al. |
| 6,436,118 B1 | 8/2002 | Kayan |
| 6,440,061 B1 | 8/2002 | Wenner et al. |
| 6,440,119 B1 | 8/2002 | Nakada et al. |
| 6,458,151 B1 | 10/2002 | Saltiel |
| 6,464,697 B1 | 10/2002 | Edwards et al. |
| 6,474,340 B1 | 11/2002 | Vaska et al. |
| 6,475,223 B1 | 11/2002 | Werp et al. |
| 6,478,769 B1 | 11/2002 | Parker |
| 6,482,162 B1 | 11/2002 | Moore |
| 6,484,727 B1 | 11/2002 | Vaska et al. |
| 6,485,489 B2 | 11/2002 | Teirstein et al. |
| 6,488,671 B1 | 12/2002 | Constantz et al. |
| 6,494,902 B2 | 12/2002 | Hoey et al. |
| 6,497,705 B2 | 12/2002 | Comben |
| 6,500,174 B1 | 12/2002 | Maguire et al. |
| 6,502,576 B1 | 1/2003 | Lesh |
| 6,514,249 B1 | 2/2003 | Maguire et al. |
| 6,517,533 B1 | 2/2003 | Swaminathan |
| 6,527,979 B2 | 3/2003 | Constantz et al. |
| 6,532,380 B1 | 3/2003 | Close et al. |
| 6,533,767 B2 | 3/2003 | Johansson et al. |
| 6,537,272 B2 | 3/2003 | Christopherson et al. |
| 6,540,733 B2 | 4/2003 | Constantz et al. |
| 6,540,744 B2 | 4/2003 | Hassett et al. |
| 6,544,195 B2 | 4/2003 | Wilson et al. |
| 6,547,780 B1 | 4/2003 | Sinofsky |
| 6,558,375 B1 | 5/2003 | Sinofsky et al. |
| 6,558,382 B2 | 5/2003 | Jahns et al. |
| 6,562,020 B1 | 5/2003 | Constantz et al. |
| 6,572,609 B1 | 6/2003 | Farr et al. |
| 6,579,285 B2 | 6/2003 | Sinofsky |
| 6,585,732 B2 | 7/2003 | Mulier et al. |
| 6,587,709 B2 | 7/2003 | Solf et al. |
| 6,593,884 B1 | 7/2003 | Gilboa et al. |
| 6,605,055 B1 | 8/2003 | Sinofsky et al. |
| 6,613,062 B1 | 9/2003 | Leckrone et al. |
| 6,622,732 B2 | 9/2003 | Constantz |
| 6,626,855 B1 | 9/2003 | Weng et al. |
| 6,626,900 B1 | 9/2003 | Sinofsky et al. |
| 6,635,070 B2 | 10/2003 | Leeflang |
| 6,645,202 B1 | 11/2003 | Pless et al. |
| 6,650,923 B1 | 11/2003 | Lesh et al. |
| 6,658,279 B2 | 12/2003 | Swanson et al. |
| 6,659,940 B2 | 12/2003 | Adler |
| 6,673,090 B2 | 1/2004 | Root et al. |
| 6,676,656 B2 | 1/2004 | Sinofsky |
| 6,679,836 B2 | 1/2004 | Couvillon, Jr. |
| 6,682,526 B1 | 1/2004 | Jones |
| 6,689,128 B2 | 2/2004 | Sliwa, Jr. et al. |
| 6,692,430 B2 | 2/2004 | Adler |
| 6,701,581 B2 | 3/2004 | Senovich et al. |
| 6,701,931 B2 | 3/2004 | Sliwa, Jr. et al. |
| 6,702,780 B1 | 3/2004 | Gilboa et al. |
| 6,704,043 B2 | 3/2004 | Goldstein et al. |
| 6,706,039 B2 | 3/2004 | Mulier et al. |
| 6,712,798 B2 | 3/2004 | Constantz |
| 6,719,747 B2 | 4/2004 | Constantz et al. |
| 6,719,755 B2 | 4/2004 | Sliwa, Jr. et al. |
| 6,730,063 B2 | 5/2004 | Delaney et al. |
| 6,736,810 B2 | 5/2004 | Hoey et al. |
| 6,751,492 B2 | 6/2004 | Ben-Haim |
| 6,755,790 B2 | 6/2004 | Stewart et al. |
| 6,755,811 B1 | 6/2004 | Constantz |
| 6,764,487 B2 | 7/2004 | Mulier et al. |
| 6,771,996 B2 | 8/2004 | Bowe et al. |
| 6,773,402 B2 | 8/2004 | Govari et al. |
| 6,780,151 B2 | 8/2004 | Grabover et al. |
| 6,805,128 B1 | 10/2004 | Pless et al. |
| 6,805,129 B1 | 10/2004 | Pless et al. |
| 6,811,562 B1 | 11/2004 | Pless |
| 6,833,814 B2 | 12/2004 | Gilboa et al. |
| 6,840,923 B1 | 1/2005 | Lapcevic |
| 6,840,936 B2 | 1/2005 | Sliwa, Jr. et al. |
| 6,849,073 B2 | 2/2005 | Hoey et al. |
| 6,858,005 B2 | 2/2005 | Ohline et al. |
| 6,858,026 B2 | 2/2005 | Sliwa, Jr. et al. |
| 6,863,668 B2 | 3/2005 | Gillespie et al. |
| 6,866,651 B2 | 3/2005 | Constantz |
| 6,887,237 B2 | 5/2005 | McGaffigan |
| 6,892,091 B1 | 5/2005 | Ben-Haim et al. |
| 6,896,690 B1 | 5/2005 | Lambrecht et al. |
| 6,899,672 B2 | 5/2005 | Chin et al. |
| 6,915,154 B1 | 7/2005 | Docherty et al. |
| 6,916,284 B2 | 7/2005 | Moriyama |
| 6,923,805 B1 | 8/2005 | LaFontaine et al. |
| 6,929,010 B2 | 8/2005 | Vaska et al. |
| 6,932,809 B2 | 8/2005 | Sinofsky |
| 6,939,348 B2 | 9/2005 | Malecki et al. |
| 6,942,657 B2 | 9/2005 | Sinofsky et al. |
| 6,949,095 B2 | 9/2005 | Vaska et al. |
| 6,953,457 B2 | 10/2005 | Farr et al. |
| 6,955,173 B2 | 10/2005 | Lesh |
| 6,962,589 B2 | 11/2005 | Mulier et al. |
| 6,971,394 B2 | 12/2005 | Sliwa, Jr. et al. |
| 6,974,464 B2 | 12/2005 | Quijano et al. |
| 6,979,290 B2 | 12/2005 | Mourlas et al. |
| 6,982,740 B2 | 1/2006 | Adair et al. |
| 6,984,232 B2 | 1/2006 | Vanney et al. |
| 6,994,094 B2 | 2/2006 | Schwartz |
| 7,019,610 B2 | 3/2006 | Creighton, IV et al. |
| 7,025,746 B2 | 4/2006 | Tal |
| 7,030,904 B2 | 4/2006 | Adair et al. |
| 7,041,098 B2 | 5/2006 | Farley et al. |
| 7,042,487 B2 | 5/2006 | Nakashima |
| 7,044,135 B2 | 5/2006 | Lesh |
| 7,052,493 B2 | 5/2006 | Vaska et al. |
| 7,090,683 B2 | 8/2006 | Brock et al. |
| 7,118,566 B2 | 10/2006 | Jahns |
| 7,156,845 B2 | 1/2007 | Mulier et al. |
| 7,163,534 B2 | 1/2007 | Brucker et al. |
| 7,166,537 B2 | 1/2007 | Jacobsen et al. |
| 7,169,144 B2 | 1/2007 | Hoey et al. |
| 7,186,214 B2 | 3/2007 | Ness |
| 7,207,984 B2 | 4/2007 | Farr et al. |
| 7,217,268 B2 | 5/2007 | Eggers et al. |
| 7,242,832 B2 | 7/2007 | Carlin et al. |
| 7,247,155 B2 | 7/2007 | Hoey et al. |
| 7,261,711 B2 | 8/2007 | Mulier et al. |
| 7,263,397 B2 | 8/2007 | Hauck et al. |
| 7,276,061 B2 | 10/2007 | Schaer et al. |
| 7,309,328 B2 | 12/2007 | Kaplan et al. |
| 7,416,552 B2 | 8/2008 | Paul et al. |
| 7,435,248 B2 | 10/2008 | Taimisto et al. |
| 7,527,625 B2 | 5/2009 | Knight et al. |
| 7,534,204 B2 * | 5/2009 | Starksen et al. ............... 600/116 |
| 7,569,052 B2 | 8/2009 | Phan et al. |
| 7,736,347 B2 | 6/2010 | Kaplan et al. |
| 7,758,499 B2 | 7/2010 | Adler |
| 7,860,555 B2 | 12/2010 | Saadat |
| 7,860,556 B2 | 12/2010 | Saadat |
| 8,131,350 B2 | 3/2012 | Saadat et al. |
| 8,137,333 B2 | 3/2012 | Saadat et al. |
| 2001/0005789 A1 | 6/2001 | Root et al. |
| 2001/0020126 A1 | 9/2001 | Swanson et al. |
| 2001/0039416 A1 | 11/2001 | Moorman et al. |
| 2001/0047136 A1 | 11/2001 | Domanik et al. |

| | | |
|---|---|---|
| 2001/0047184 A1 | 11/2001 | Connors |
| 2001/0052930 A1 | 12/2001 | Adair et al. |
| 2002/0004644 A1 | 1/2002 | Koblish |
| 2002/0026145 A1 | 2/2002 | Bagaoisan et al. |
| 2002/0054852 A1 | 5/2002 | Cate |
| 2002/0065455 A1 | 5/2002 | Ben-Haim et al. |
| 2002/0068853 A1 | 6/2002 | Adler |
| 2002/0080248 A1 | 6/2002 | Adair et al. |
| 2002/0087166 A1 | 7/2002 | Brock et al. |
| 2002/0087169 A1 | 7/2002 | Brock et al. |
| 2002/0091304 A1 | 7/2002 | Takeshi et al. |
| 2002/0138088 A1 | 9/2002 | Nash et al. |
| 2002/0165598 A1 | 11/2002 | Wahr et al. |
| 2002/0169377 A1 | 11/2002 | Khairkhahan et al. |
| 2003/0009085 A1 | 1/2003 | Arai et al. |
| 2003/0035156 A1 | 2/2003 | Cooper |
| 2003/0036698 A1 | 2/2003 | Kohler et al. |
| 2003/0069593 A1 | 4/2003 | Tremulis et al. |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0216720 A1 | 11/2003 | Sinofsky et al. |
| 2003/0220574 A1 | 11/2003 | Markus et al. |
| 2003/0222325 A1 | 12/2003 | Jacobsen et al. |
| 2004/0006333 A1 | 1/2004 | Arnold et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler et al. |
| 2004/0097788 A1* | 5/2004 | Mourlas et al. ............. 600/116 |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210239 A1 | 10/2004 | Nash et al. |
| 2004/0215180 A1 | 10/2004 | Starkebaum et al. |
| 2004/0215183 A1 | 10/2004 | Hoey et al. |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0065504 A1 | 3/2005 | Melsky et al. |
| 2005/0090818 A1 | 4/2005 | Pike, Jr. et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0119523 A1 | 6/2005 | Starksen et al. |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0158899 A1 | 7/2005 | Jacobsen et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0182465 A1 | 8/2005 | Ness |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2005/0267452 A1 | 12/2005 | Farr et al. |
| 2006/0009715 A1 | 1/2006 | Khairkhahan et al. |
| 2006/0009737 A1 | 1/2006 | Whiting et al. |
| 2006/0015096 A1 | 1/2006 | Hauck et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0030844 A1 | 2/2006 | Knight et al. |
| 2006/0069303 A1 | 3/2006 | Couvillon et al. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima |
| 2006/0184048 A1 | 8/2006 | Saadat |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0258909 A1 | 11/2006 | Saadat et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0055142 A1 | 3/2007 | Webler |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100241 A1 | 5/2007 | Adler |
| 2007/0100324 A1 | 5/2007 | Tempel et al. |
| 2007/0106146 A1 | 5/2007 | Claudio et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0167828 A1 | 7/2007 | Saadat |
| 2007/0265609 A1 | 11/2007 | Thapliyal et al. |
| 2007/0265610 A1 | 11/2007 | Thapliyal et al. |
| 2007/0270686 A1 | 11/2007 | Ritter et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015445 A1 | 1/2008 | Saadat et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033241 A1 | 2/2008 | Peh et al. |
| 2008/0033290 A1 | 2/2008 | Saadat et al. |
| 2008/0057106 A1 | 3/2008 | Erickson et al. |
| 2008/0058590 A1 | 3/2008 | Saadat et al. |
| 2008/0058650 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0188759 A1 | 8/2008 | Saadat et al. |
| 2008/0214889 A1 | 9/2008 | Saadat et al. |
| 2008/0228032 A1 | 9/2008 | Starksen et al. |
| 2008/0275300 A1 | 11/2008 | Rothe et al. |
| 2008/0281293 A1 | 11/2008 | Peh et al. |
| 2008/0287790 A1 | 11/2008 | Li |
| 2008/0287805 A1 | 11/2008 | Li |

| | | | |
|---|---|---|---|
| 2009/0030276 | A1 | 1/2009 | Saadat et al. |
| 2009/0030412 | A1 | 1/2009 | Willis et al. |
| 2009/0054803 | A1 | 2/2009 | Saadat et al. |
| 2009/0062790 | A1 | 3/2009 | Malchano et al. |
| 2009/0076489 | A1 | 3/2009 | Welches et al. |
| 2009/0076498 | A1 | 3/2009 | Saadat et al. |
| 2009/0082623 | A1 | 3/2009 | Rothe et al. |
| 2009/0125022 | A1 | 5/2009 | Saadat et al. |
| 2009/0143640 | A1 | 6/2009 | Saadat et al. |
| 2009/0187074 | A1 | 7/2009 | Saadat et al. |
| 2009/0203962 | A1 | 8/2009 | Miller et al. |
| 2009/0221871 | A1 | 9/2009 | Peh et al. |
| 2009/0227999 | A1 | 9/2009 | Willis et al. |
| 2009/0264727 | A1 | 10/2009 | Markowitz et al. |
| 2009/0267773 | A1 | 10/2009 | Markowitz et al. |
| 2009/0275799 | A1 | 11/2009 | Saadat et al. |
| 2009/0275842 | A1 | 11/2009 | Saadat et al. |
| 2009/0299363 | A1 | 12/2009 | Saadat et al. |
| 2009/0326572 | A1 | 12/2009 | Peh et al. |
| 2010/0004506 | A1 | 1/2010 | Saadat et al. |
| 2010/0004633 | A1 | 1/2010 | Rothe et al. |
| 2010/0004661 | A1 | 1/2010 | Verin et al. |
| 2010/0010311 | A1 | 1/2010 | Miller et al. |
| 2010/0094081 | A1 | 4/2010 | Rothe et al. |
| 2010/0130836 | A1 | 5/2010 | Malchano et al. |
| 2011/0060227 | A1 | 3/2011 | Saadat |
| 2011/0060298 | A1 | 3/2011 | Saadat |
| 2011/0144576 | A1 | 6/2011 | Rothe et al. |
| 2012/0016221 | A1 | 1/2012 | Saadat et al. |
| 2012/0059366 | A1 | 3/2012 | Drews et al. |

FOREIGN PATENT DOCUMENTS

| | | |
|---|---|---|
| EP | 0283661 | 9/1988 |
| EP | 0301288 A1 | 2/1999 |
| JP | 59093413 A | 5/1984 |
| JP | 59-181315 | 10/1984 |
| JP | 01-221133 | 9/1989 |
| JP | 03-284265 | 12/1991 |
| JP | 05-103746 | 4/1993 |
| JP | 09-051897 | 2/1997 |
| JP | 11-299725 | 11/1999 |
| JP | 2001-258822 | 9/2001 |
| WO | WO 92/21292 | 12/1992 |
| WO | WO 94/07413 | 4/1994 |
| WO | WO 95/03843 | 2/1995 |
| WO | WO 98/18388 | 5/1998 |
| WO | WO 03/039350 | 5/2003 |
| WO | WO 03/053491 | 7/2003 |
| WO | WO 03/101287 | 12/2003 |
| WO | WO 2004/043272 | 5/2004 |
| WO | WO 2004/080508 | 9/2004 |
| WO | WO 2005/070330 | 8/2005 |
| WO | WO 2005/077435 | 8/2005 |
| WO | WO 2005/081202 | 9/2005 |
| WO | WO 2006/017517 | 2/2006 |
| WO | WO 2006/024015 | 3/2006 |
| WO | WO 2006/083794 | 8/2006 |
| WO | WO 2006/091597 | 8/2006 |
| WO | WO 2006/126979 | 11/2006 |
| WO | WO 2007/067323 | 6/2007 |
| WO | WO 2007/079268 | 7/2007 |
| WO | WO 2007/133845 | 11/2007 |
| WO | WO 2007/134258 | 11/2007 |
| WO | WO 2008/015625 | 2/2008 |
| WO | WO 2008/021994 | 2/2008 |
| WO | WO 2008/021997 | 2/2008 |
| WO | WO 2008/021998 | 2/2008 |
| WO | WO 2008/024261 | 2/2008 |
| WO | WO 2008/079828 | 7/2008 |
| WO | WO 2009/112262 | 9/2009 |

OTHER PUBLICATIONS

U.S. Appl. No. 11/560,742, filed Nov. 16, 2006 in the name of Saadat, Notice of Allowance mailed Nov. 15, 2010.
U.S. Appl. No. 12/464,800 filed May 12, 2009 in the name of Peh et al., non-final Office Action mailed Nov. 24, 2010.
U.S. Appl. No. 11/848,429, filed Aug. 31, 2007 in the name of Peh et al., non-final Office Action mailed Nov. 24, 2010.
Avitall, A Catheter System to Ablate Atrial Fibrillation in a Sterile Pericarditis Dog Model, PACE, vol. 17, p. 774, 1994.
Avitall, Right-Sided Driven Atrial Fibrillation in a Sterile Pericarditis Dog Model, PACE, vol. 17, p. 774, 1994.
Avitall, Vagally Mediated Atrial Fibrillation in a Dog Model can be Ablated by Placing Linear Radiofrequency Lesions at the Junction of the Right Atrial Appendage and the Superior Vena Cava, PACE, vol. 18, p. 857, 1995.
Baker, Nonpharmacologic Approaches to the Treatment of Atrial Fibrillation and Atrial Flutter, J. Cardiovasc. Electrophysiol., vol. 6, pp. 972-978, 1995.
Bhakta, Principles of Electroanatomic Mapping, Indian Pacing & Electrophysiol J., vol. 8, No. 1, pp. 32-50, 2008.
Bidoggia, Transseptal Left Heart Catheterization: Usefulness of the Intracavitary Electrocardiogram in the Localization of the Fossa Ovalis, Cathet Cardiovasc Diagn., vol. 24, No. 3, pp. 221-225, 1991.
Bredikis, Surgery of Tachyarrhythmia: Intracardiac Closed Heart Cryoablation, PACE, vol. 13, pp. 1980-1984, 1990.
Cox, Cardiac Surgery for Arrhythmias, J. Cardiovasc. Electrophysiol., vol. 15, pp. 250-262, 2004.
Cox, Five-Year Experience With the Maze Procedure for Atrial Fibrillation, Ann. Thorac. Surg., vol. 56, pp. 814-824, 1993.
Cox, Modification of the Maze Procedure for Atrial Flutter and Atrial Fibrillation, J. Thorac. Cardiovasc. Surg., vol. 110, pp. 473-484, 1995.
Cox, The Status of Surgery for Cardiac Arrhythmias, Circulation, vol. 71, pp. 413-417, 1985.
Cox, The Surgical Treatment of Atrial Fibrillation, J. Thorac Cardiovasc. Surg., vol. 101, pp. 584-592, 1991.
Elvan, Replication of the "Maze" Procedure by Radiofrequency Catheter Ablation Reduces the Ability to Induce Atrial Fibrillation, PACE, vol. 17, p. 774, 1994.
Elvan, Radiofrequency Catheter Ablation (RFCA) of the Atria Effectively Abolishes Pacing Induced Chronic Atrial Fibrillation, PACE, vol. 18, p. 856, 1995.
Elvan, Radiofrequency Catheter Ablation of the Atria Reduces Inducibility and Duration of Atrial Fibrillation in Dogs, Circulation, vol. 91, pp. 2235-2244, 1995.
European Patent Application No. 06734083.6 filed Jan. 30, 2006 in the name of Saadat et al., extended European Search Report mailed Jul. 1, 2009.
European Patent Application No. 06734083.6 filed Jan. 30, 2006 in the name of Saadat et al., office action mailed Oct. 23, 2009.
Fieguth, Inhibition of Atrial Fibrillation by Pulmonary Vein Isolation and Auricular Resection—Experimental Study in a Sheep Model, European J. Cardiothorac. Surg., vol. 11, pp. 714-721, 1997.
Hoey, Intramural Ablation Using Radiofrequency Energy Via Screw-Tip Catheter and Saline Electrode, PACE, vol. 18, p. 487, 1995.
Huang, Increase in the Lesion Size and Decrease in the Impedance Rise with a Saline Infusion Electrode Catheter for Radiofrequency, Circulation, vol. 80, No. 4, pp. II-324, 1989.
Moser, Angioscopic Visualization of Pulmonary Emboli, CHEST, vol. 77, No. 2, pp. 198-201, 1980.
Nakamura, Percutaneous Intracardiac Surgery With Cardioscopic Guidance, SPIE, vol. 1652, pp. 214-216, 1992.
Pappone, Circumferential Radiofrequency Ablation of Pulmonary Vein Ostia, Circulation, vol. 102, pp. 2619-2628, 2000.
Sethi, Transseptal Catheterization for the Electrophysiologist: Modification with a "View", J. Interv. Card. Electrophysiol., vol. 5, pp. 97-99, 2001, Kluwer Academic Publishers, Netherlands.
Thiagalingam, Cooled Needle Catheter Ablation Creates Deeper and Wider Lesions than Irrigated Tip Catheter Ablation, J. Cardiovasc. Electrophysiol., vol. 16, pp. 1-8, 2005.
U.S. Appl. No. 11/828,267, filed Jul. 25, 2007 in the name of Saadat et al., Non-final Office Action mailed Jan. 14, 2010.
U.S. Appl. No. 12/117,655, filed May 8, 2008 in the name of Saadat et al., Non-final Office Action mailed Jun. 8, 2009.
Willkampf, Radiofrequency Ablation with a Cooled Porous Electrode Catheter, JACC, vol. 11, No. 2, p. 17A, 1988.
European Patent Application No. 06734083.6 filed Jan. 30, 2006 in the name of Voyage Medical, Inc., Office Action mailed Nov. 12, 2010.

U.S. Appl. No. 12/947,198, filed Nov. 16, 2010 in the name of Saadat, non-final Office Action mailed Feb. 18, 2011.
U.S. Appl. No. 12/947,246, filed Nov. 16, 2006 in the name of Saadat, non-final Office Action mailed Feb. 18, 2011.
U.S. Appl. No. 11/687,597, filed Mar. 16, 2007 in the name of Saadat, Notice of Allowance mailed Feb. 24, 2011.
U.S. Appl. No. 11/560,732, filed Mar. 16, 2007 in the name of Saadat, Notice of Allowance mailed Feb. 24, 2011.
U.S. Appl. No. 11/848,207, filed Aug. 30, 2007 in the name of Saadat et al., non-final Office Action mailed Feb. 25, 2011.
Japanese Patent Application No. 2007-554156 filed Jan. 30, 2006 in the name of Voyage Medical, Inc., Office Action mailed Feb. 15, 2011.
European Patent Application No. 07758716.0 filed Mar. 16, 2007 in the name of Voyage Medical, Inc., Supplemental European Search Report mailed Feb. 28, 2011.
U.S. Appl. No. 11/848,202, filed Aug. 30, 2007 in the name of Saadat et al., non-final Office Action mailed Mar. 11, 2011.
U.S. Appl. No. 11/763,399, filed Jun. 14, 2007 in the name of Saadat et al., non-final Office Action mailed Apr. 11, 2011.
U.S. Appl. No. 12/499,011, filed Jul. 7, 2009 in the name of Rothe et al., non-final Office Action mailed Apr. 12, 2011.
U.S. Appl. No. 12/367,019, filed Feb. 6, 2009 in the name of Miller et al., non-final Office Action mailed Apr. 22, 2011.
U.S. Appl. No. 11/959,158, filed Dec. 18, 2007 in the name of Saadat et al., non-final Office Action mailed Apr. 25, 2011.
U.S. Appl. No. 11/848,532, filed Aug. 31, 2007 in the name of Saadat et al., non-final Office Action mailed Apr. 26, 2011.
U.S. Appl. No. 11/828,281, filed Jul. 25, 2007 in the name of Peh et al., non-final Office Action mailed Apr. 27, 2011.
U.S. Appl. No. 11/961,950, filed Dec. 20, 2007 in the name of Saadat et al., non-final Office Action mailed May 9, 2011.
U.S. Appl. No. 11/961,995, filed Dec. 20, 2007 in the name of Saadat et al., non-final Office Action mailed May 9, 2011.
U.S. Appl. No. 11/962,029, filed Dec. 20, 2007 in the name of Saadat et al., non-final Office Action mailed May 9, 2011.
U.S. Appl. No. 11/828,267, filed Jul. 25, 2007 in the name of Saadat et al., non-final Office Action mailed May 11, 2011.
Japanese Patent Application No. 2009-500630 filed Mar. 16, 2007 in the name of Voyage Medical, Inc., Office Action mailed Apr. 27, 2011.
U.S. Appl. No. 11/775,771, filed Jul. 10, 2007 in the name of Saadat et al., final Office Action mailed May 12, 2011.
U.S. Appl. No. 11/877,386, filed Oct. 23, 2007 in the name of Saadat et al., non-final Office Action mailed May 20, 2011.
U.S. Appl. No. 11/775,819, filed Jul. 10, 2007 in the name of Saadat et al., non-final Office Action mailed May 20, 2011.
U.S. Appl. No. 11/775,837, filed Jul. 10, 2007 in the name of Saadat et al., non-final Office Action mailed May 23, 2011.
U.S. Appl. No. 12/117,655, filed May 8, 2008 in the name of Peh et al., final Office Action mailed Jun. 2, 2011.
U.S. Appl. No. 12/323,281, filed Nov. 25, 2008 in the name of Saadat et al., non-final Office Action mailed Jun. 7, 2011.
Japanese Patent Application No. 2007-554156 filed Jan. 30, 2006 in the name of Voyage Medical, Inc., Notice of Allowance mailed Jun. 13, 2011.
European Patent Application No. 06734083.6 filed Jan. 30, 2006 in the name of Saadat et al., Examination Communication mailed May 18, 2010.
European Patent Application No. 07841754.0 filed Aug. 31, 2007 in the name of Saadat et al., Supplemental European Search Report mailed Jun. 30, 2010.
European Patent Application No. 08746822.9 filed Apr. 24, 2008 in the name of Rothe et al., European Search Report mailed Mar. 29, 2010.
European Patent Application No. 08746822.9 filed Apr. 24, 2008 in the name of Rothe et al., Office Action mailed Jul. 13, 2010.
U.S. Appl. No. 11/259,498, filed Oct. 25, 2005 n. The name of Saadat et al., Non-final Office Action mailed Feb. 25, 2010.
U.S. Appl. No. 11/560,742, filed Nov. 16, 2006 in the name of Saadat, Non-final Office Action mailed Jun. 10, 2010.
U.S. Appl. No. 11/687,597 filed Mar. 16, 2007 in the name of Saadat et al., Non-final Office Action mailed Jul. 21, 2010.
U.S. Appl. No. 12/117,655, filed May 8, 2008 in the name of Peh et al., Final Office Action mailed Mar. 1, 2010.
U.S. Appl.No. 61/286,283 filed Dec. 14, 2009 in the name of Rothe et al.
U.S. Appl. No. 61/297,462, filed Jan. 22, 2010 in the name of Rothe et al.
Uchida, Developmental History of Cardioscopes, Coronary Angioscopy, pp. 187-197, 2001, Futura Publishing Co., Armonk, NY.
U.S. Appl. No. 11/775,771, filed Jul. 10, 2007 in the name of Saadat et al., Non-final Office Action mailed Aug. 27, 2010.
U.S. Appl. No. 11/828,267, filed Jul. 25, 2007 in the name of Saadat et al., final Office Action mailed Sep. 16, 2010.
U.S. Appl. No. 11/560,732, filed Nov. 16, 2006 in the name of Saadat, Notice of Allowance mailed Feb. 3, 2011.
U.S. Appl. No. 12/464,800, filed May 12, 2009 in the name of Peh et al., non-final Office Action mailed Nov. 24, 2010.
European Patent Application No. 07812146.4 filed Jun. 14, 2007 in the name of Voyage Medical, Inc., European Search Report mailed Nov. 18, 2010.
European Patent Application No. 07799466.3 filed Jul. 10, 2007 in the name of Voyage Medical, Inc., European Search Report mailed Nov. 18, 2010.
U.S. Appl. No. 12/117,655, filed May 8, 2008 in the name of Peh et al., non-final Office Action mailed Dec. 16, 2010.
U.S. Appl. No. 12/026,455, filed Feb. 5, 2008 in the name of Saadat et al., non-final Office Action mailed Dec. 27, 2010.

* cited by examiner

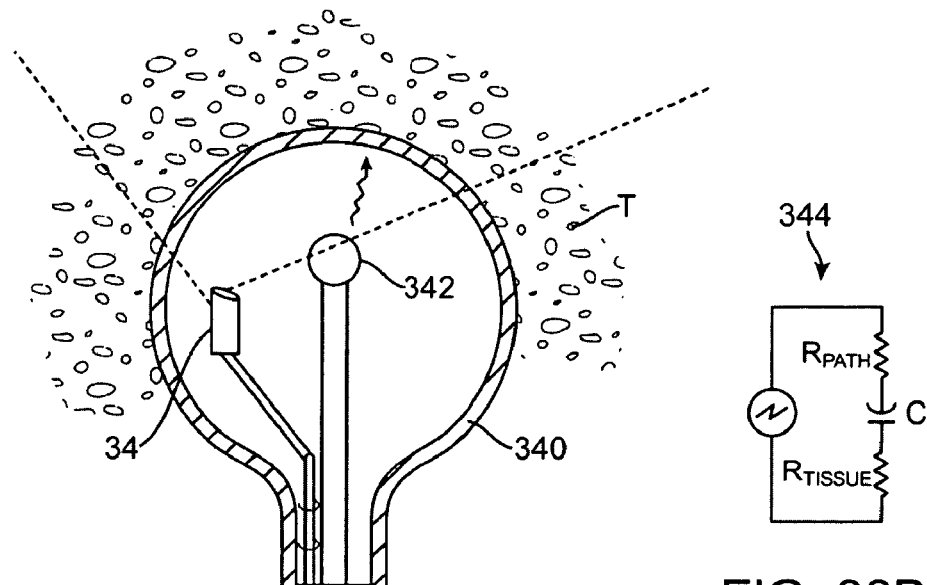
FIG. 33A
FIG. 33B
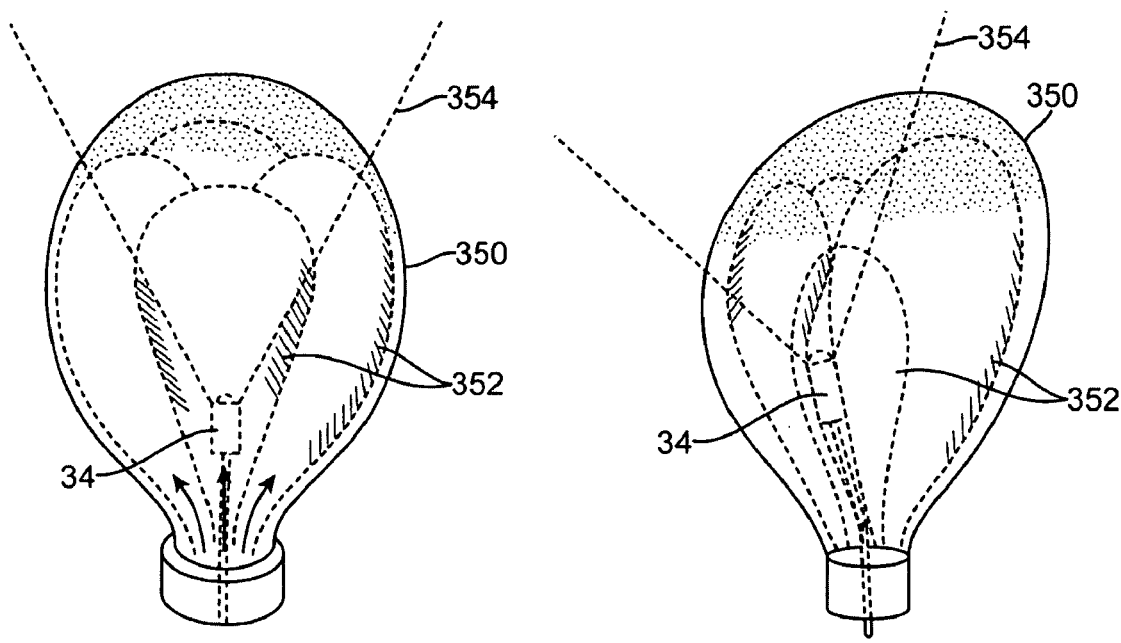
FIG. 34A
FIG. 34B

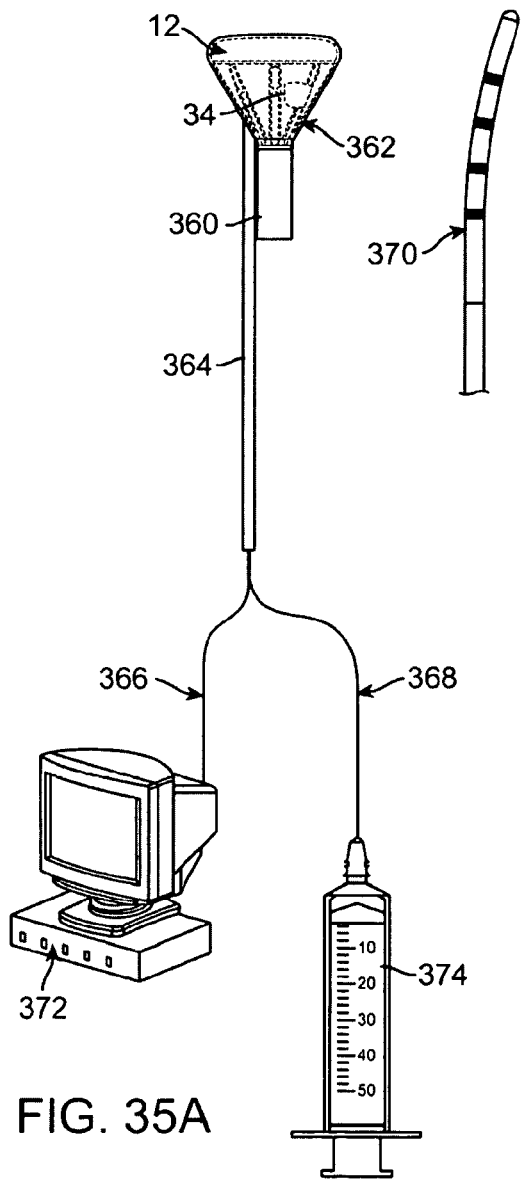
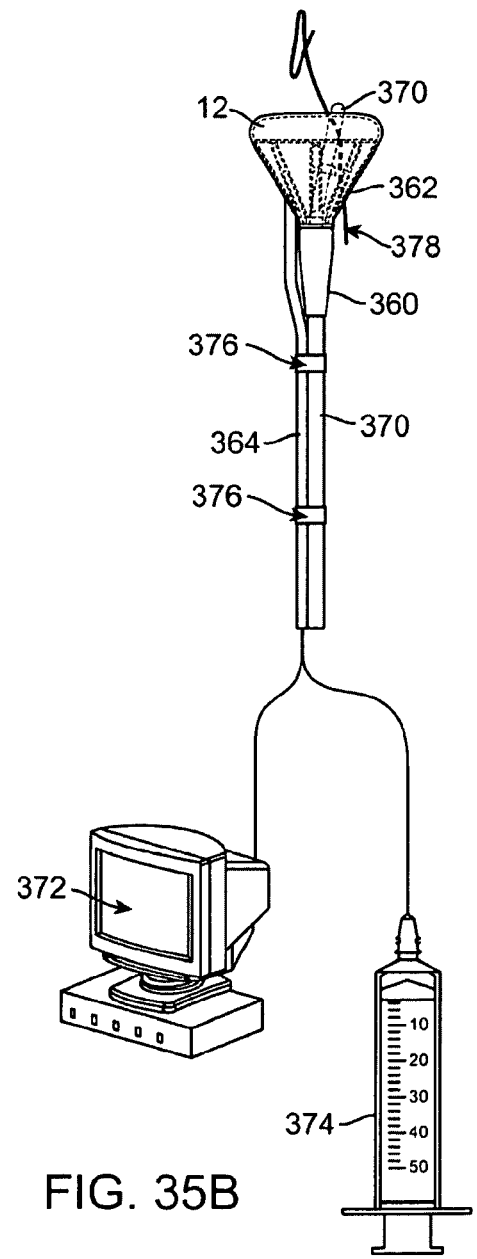
FIG. 35A
FIG. 35B

VISUALIZATION AND ABLATION SYSTEM VARIATIONS

CROSS-REFERENCE TO RELATED APPLICATIONS

This application claims the benefit of priority to U.S. Prov. Pat. App. 60/971,462 filed Sep. 11, 2007, and is also a continuation-in-part of U.S. patent application Ser. No. 12/201,811 filed Aug. 29, 2008 which claims the benefit of priority to U.S. Prov. Pat. App. 60/969,511 filed Aug. 31, 2007, each of which is incorporated herein by reference in its entirety.

FIELD OF THE INVENTION

The present invention relates generally to medical devices used for accessing, visualizing, and/or treating regions of tissue within a body. More particularly, the present invention relates to methods and apparatus for the delivery of ablation energy, such as radio-frequency (RF) ablation, to an underlying target tissue utilizing a bipolar electrode configuration for treatment in a controlled manner, while directly visualizing the tissue.

BACKGROUND OF THE INVENTION

Conventional devices for visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging. Additionally, imaging balloons are subject to producing poor or blurred tissue images if the balloon is not firmly pressed against the tissue surface because of intervening blood between the balloon and tissue.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Thus, a tissue imaging system which is able to provide real-time in vivo images of tissue regions within body lumens such as the heart through opaque media such as blood and which also provide instruments for therapeutic procedures upon the visualized tissue are desirable.

SUMMARY OF THE INVENTION

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

In an exemplary variation for imaging tissue surfaces within a heart chamber containing blood, the tissue imaging and treatment system may generally comprise a catheter body having a lumen defined therethrough, a visualization element disposed adjacent the catheter body, the visualization element having a field of view, a transparent fluid source in fluid communication with the lumen, and a barrier or membrane extendable from the catheter body to localize, between the visualization element and the field of view, displacement of blood by transparent fluid that flows from the lumen, and an instrument translatable through the displaced blood for performing any number of treatments upon the tissue surface within the field of view. The imaging hood may be formed into any number of configurations and the imaging assembly may also be utilized with any number of therapeutic tools which may be deployed through the deployment catheter.

More particularly in certain variations, the tissue visualization system may comprise components including the imaging hood, where the hood may further include a membrane having a main aperture and additional optional openings disposed over the distal end of the hood. An introducer sheath or the deployment catheter upon which the imaging hood is disposed may further comprise a steerable segment made of multiple adjacent links which are pivotably connected to one another and which may be articulated within a single plane or multiple planes. The deployment catheter itself may be comprised of a multiple lumen extrusion, such as a four-lumen catheter extrusion, which is reinforced with braided stainless steel fibers to provide structural support. The proximal end of the catheter may be coupled to a handle for manipulation and articulation of the system.

To provide visualization, an imaging element such as a fiberscope or electronic imager such as a solid state camera, e.g., CCD or CMOS, may be mounted, e.g., on a shape memory wire, and positioned within or along the hood interior. A fluid reservoir and/or pump (e.g., syringe, pressurized intravenous bag, etc.) may be fluidly coupled to the proximal end of the catheter to hold the translucent fluid such as saline or contrast medium as well as for providing the pressure to inject the fluid into the imaging hood.

In treating tissue regions which are directly visualized, as described above, treatments utilizing electrical energy may be employed to ablate the underlying visualized tissue. Many ablative systems typically employ electrodes arranged in a monopolar configuration where a single electrode is positioned proximate to or directly against the tissue to be treated within the patient body and a return electrode is located external to the patient body. Utilization of bipolar electrode ablation removes the need for a return or grounding electrode to be adhered to the skin of the patient and may further allow for a more precise delivery of ablation energy over a small target area for creation of precise lesions.

In particular, such assemblies, apparatus, and methods may be utilized for treatment of various conditions, e.g., arrhythmias, through ablation under direct visualization. Variations of the tissue imaging and manipulation apparatus may be configured to facilitate the application of bipolar energy delivery, such as radio-frequency (RF) ablation, to an underlying target tissue for treatment in a controlled manner while directly visualizing the tissue during the bipolar ablation process as well as confirming (visually and otherwise) appropriate treatment thereafter.

Various configurations may be utilized for a bipolar electrode arrangement which allows for bipolar ablation of tissue within the visual field being imaged via an imaging element. The current may be conducted between the electrodes through the transparent saline fluid infused into and through the hood. One example may include a first electrode positioned within or along the imaging hood and a second electrode positioned along the distal membrane of hood. The electrode along the hood membrane may be in a number of different configurations such as a ring electrode. Alternatively, two or more electrodes may be positioned in various arrangements over the membrane.

In other variations, the hood (or balloon in other variations) may be internally segmented into two or more separated chambers where saline fluid having opposite charges may be introduced into each respective chamber for bipolar ablation. Each chamber may define a corresponding first and second aperture over the distal membrane and may also each have a corresponding first and second electrode positioned within each respective chamber. Each electrode may be positioned within the chambers via respective first and second electrode support members. The transparent fluid may be introduced into each chamber past the electrodes such that the charged fluid passing through their respective apertures may contact one another over the tissue to conduct energy therebetween and ablate the underlying tissue. In another variation, rather than utilizing two separate chambers, a second inner hood may be positioned within the visualization hood to achieve the same or similar electrode arrangement.

In yet other variations, one or more of the support struts may be configured as electrodes well. The current may flow between the respective support struts or between a first electrode and one or more of the support struts. In yet additional variations, a bipolar electrode arrangement may be positioned along the hood and/or hood membrane such that tissue drawn into the hood or portions thereof may be ablated accordingly. In drawing portions of tissue relative to the hood, various instruments, such as tissue graspers, may also be utilized and optionally configured as an electrode as well.

Other variations may also include one or more struts having conductive tips which are configured to extend distally and project past the hood. In use, as the underlying tissue is visualized, as previously described, the one or more conducting tips may be extended distally into the tissue region surrounding the hood and contacted against the tissue surface and the conducting fluid may be infused into hood and into the area immediately surrounding the hood. The ablation energy may be thus conducted between a first electrode and the one or more conducting tips to ablate the tissue therebetween.

Additional instruments such as needles or needle assemblies may be advanced into the underlying tissue being visualized. The one or more needles may be configured as electrodes as well to allow for conduction into the underlying tissue for creating transmural lesions. Aside from needles, other instruments such as expandable anchors or ablation probe members may alternatively be utilized.

In yet other variations, a return electrode may be positioned proximally of the hood, e.g., along the deployment catheter or outer sheath. In such an arrangement, the return electrode may be positioned along a first tissue region, such as an atrial septum, while the first electrode is advanced distally such as in a left atrium of the heart. Conduction between the electrodes may thus be effected to ablate the tissue underlying and/or surrounding the electrode arrangement. In other variations, a separate instrument incorporating a return electrode may be advanced within the patient body, e.g., intravascularly or through a body cavity, and positioned in proximity to the electrode to effect ablation of the tissue region surrounding or in proximity to the electrodes.

In a further variation, ablation energy may be controlled utilizing parameters such as the salinity concentration of saline or by controlling the temperature of the transparent saline fluid, which is also utilized for visualization.

BRIEF DESCRIPTION OF THE DRAWINGS

FIG. 33A shows a partial cross-sectional side view of a visualization balloon which is configured to ablate contacted tissue through capacitive coupling while under visualization.

FIG. 33B shows a schematic of the electrical coupling when capacitively coupled to tissue.

FIGS. 34A and 34B show perspective views of another variation of a tissue visualization and ablation balloon system where individual balloons are inflatable at variable rates to articulate an imaging element within the device.

FIG. 35A shows a representative assembly view of another variation of an imaging and ablation system which is removably attachable onto a separate instrument.

FIG. 35B shows an example of an assembled imaging and ablation system where the removable assembly is attached to an ablation probe.

DETAILED DESCRIPTION OF THE INVENTION

A tissue-imaging and manipulation apparatus described herein is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
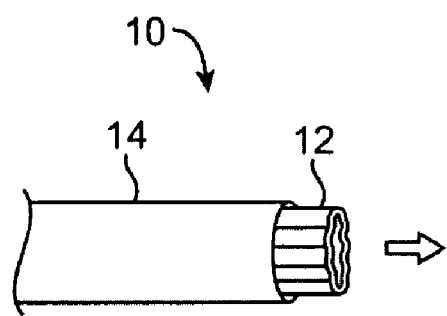
FIG. 1A shows a side view of one variation of a tissue imaging apparatus during deployment from a sheath or delivery catheter.
Figure 1B:
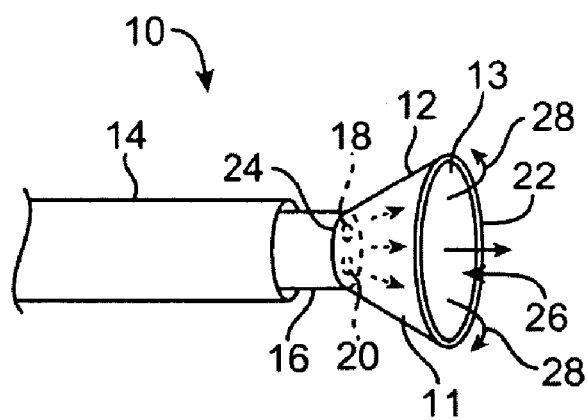
FIG. 1B shows the deployed tissue imaging apparatus of FIG. 1A having an optionally expandable hood or sheath attached to an imaging and/or diagnostic catheter.
Figure 1C:
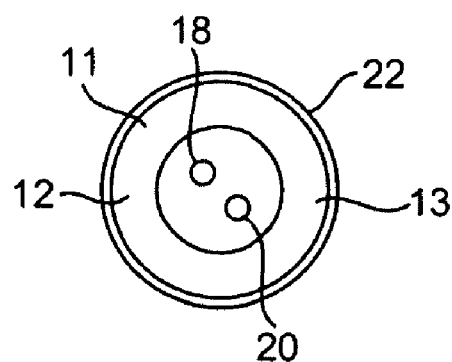
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intraatrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E.I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 1.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
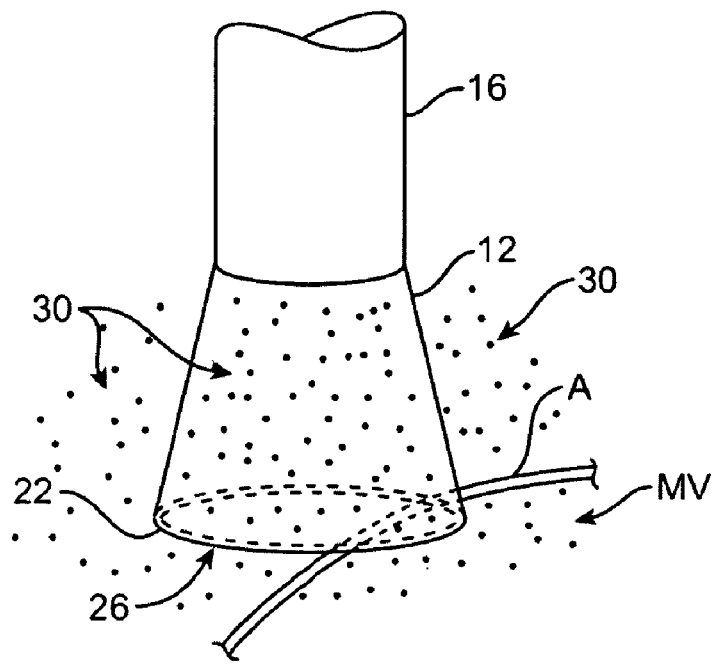
FIGS. 2A and 2B show one example of a deployed tissue imager positioned against or adjacent to the tissue to be imaged and a flow of fluid, such as saline, displacing blood from within the expandable hood.
Figure 2B:
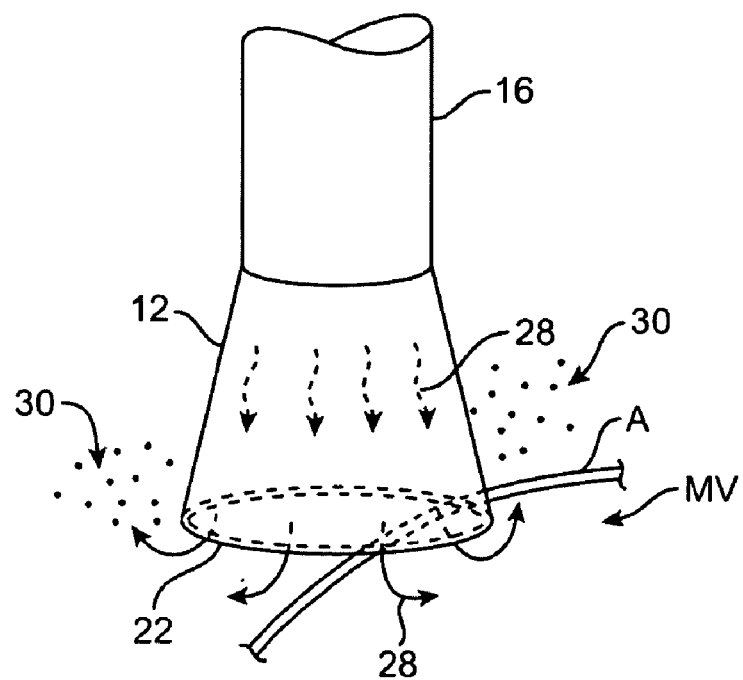

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
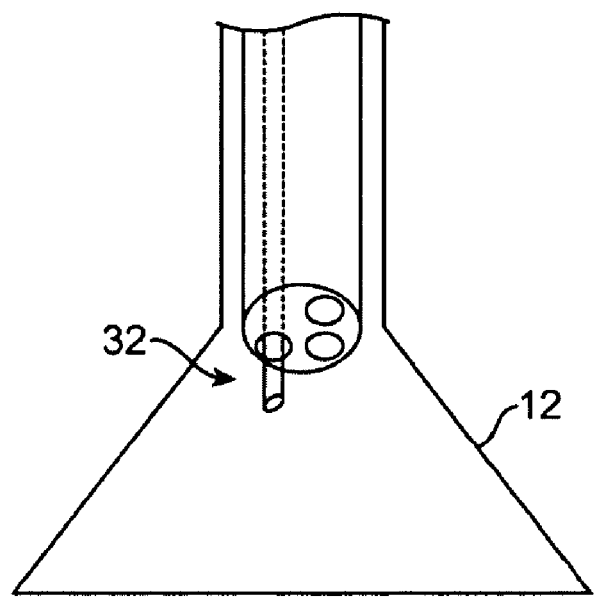
FIGS. 3A and 3B show examples of various visualization imagers which may be utilized within or along the imaging hood.
Figure 3B:
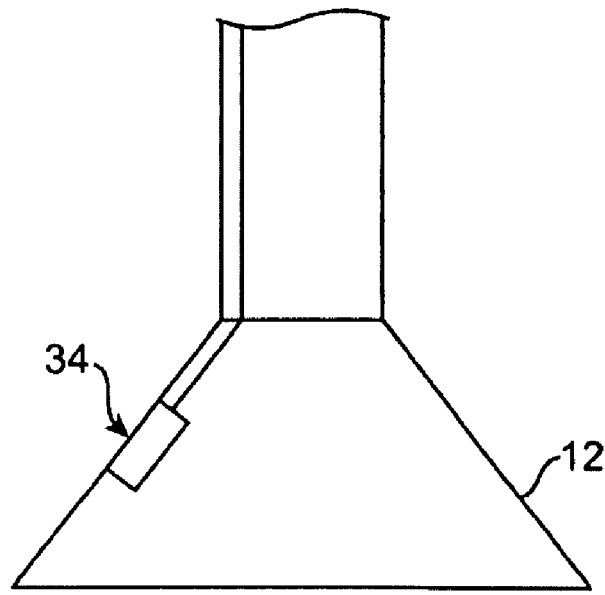

FIG. 3A shows a partial cross-sectional view of an example where one or more optical fiber bundles 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

Figure 4A:
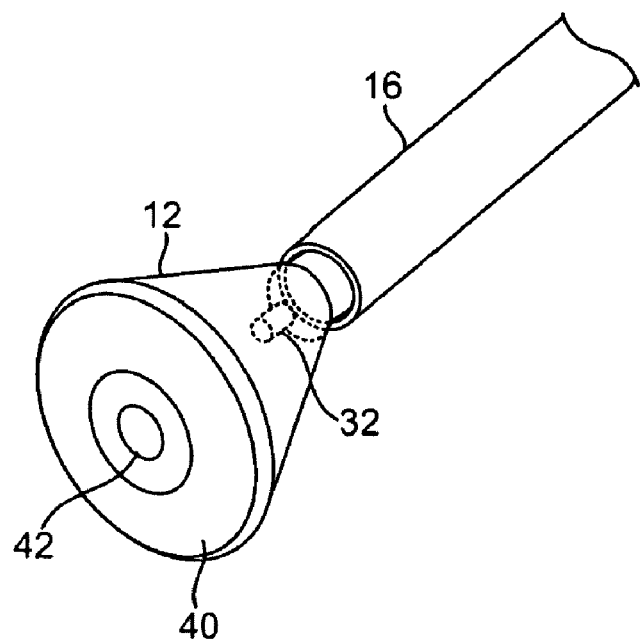
FIGS. 4A and 4B show perspective and end views, respectively, of an imaging hood having at least one layer of a transparent elastomeric membrane over the distal opening of the hood.
Figure 4B:
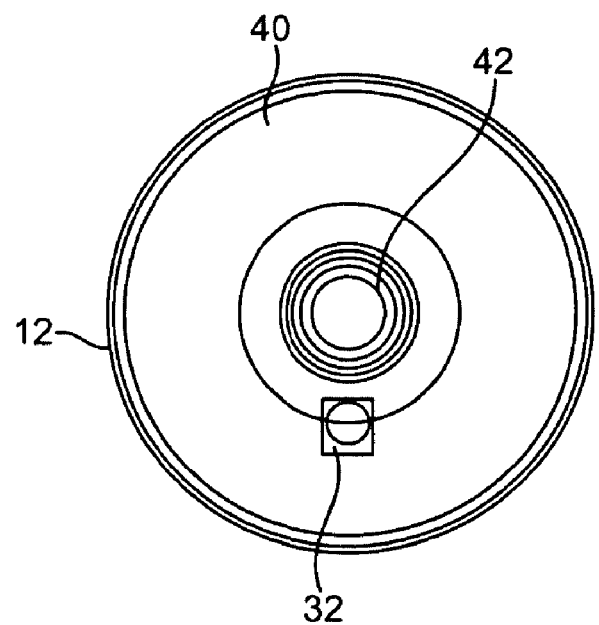

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
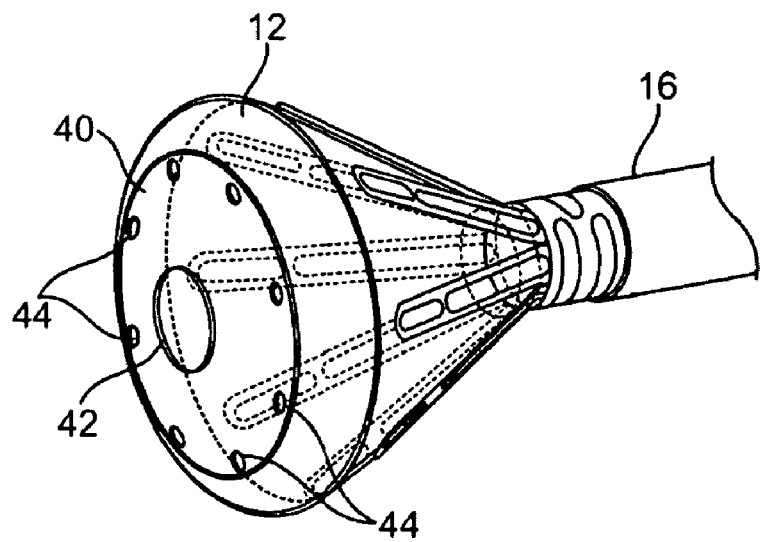
FIGS. 5A and 5B show perspective and end views, respectively, of an imaging hood which includes a membrane with an aperture defined therethrough and a plurality of additional openings defined over the membrane surrounding the aperture.
Figure 5B:
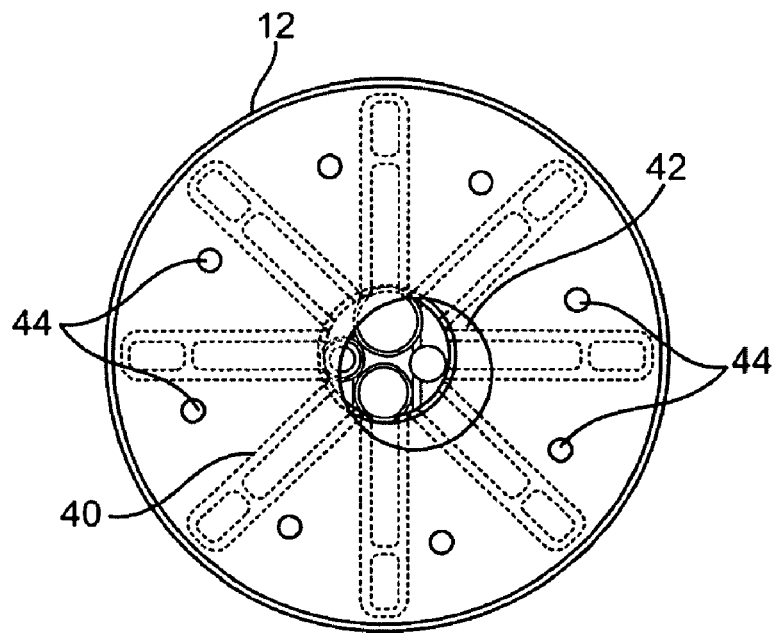

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. patent application Ser. No. 11/259,498 filed Oct. 25, 2005 (U.S. Pat. Pub. No. 2006/0184048 A1); 11/763,399 filed Jun. 14, 2007 (U.S. Pat. Pub. No. 2007/0293724 A1); and also in 11/828,267 filed Jul. 25, 2007 (U.S. Pat. Pub. No. 2008/0033290 A1), and 11/775,837 filed Jul. 10, 2007 (U.S. Pat. Pub. No. 2008/0009747 A1) each of which is incorporated herein by reference in its entirety.

Figure 6:
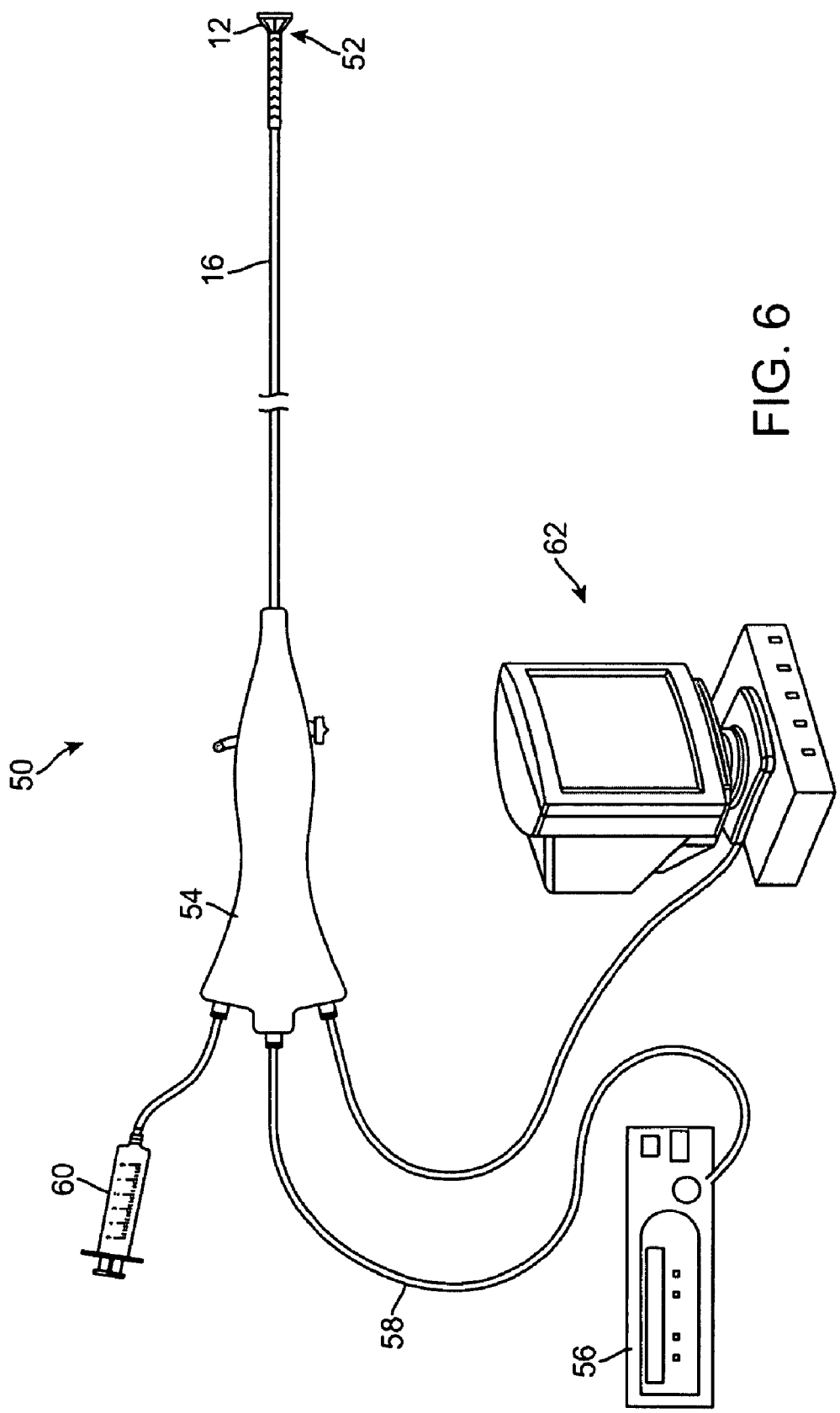
FIG. 6 shows an assembly view of a visualization system configured for tissue ablation utilizing a bipolar electrode configuration.

In treating tissue regions which are directly visualized, as described above, treatments utilizing electrical energy may be employed to ablate the underlying visualized tissue. Many ablative systems typically employ electrodes arranged in a monopolar configuration where a single electrode is positioned proximate to or directly against the tissue to be treated within the patient body and a return electrode is located external to the patient body. The assembly illustrated in FIG. 6 shows an example of a tissue visualization system which is configured with electrodes arranged in a bipolar configuration where the electrode and return electrode are arranged in proximity to the tissue region to be treated and visualized. Utilization of bipolar electrode ablation removes the need for a return or grounding electrode to be adhered to the skin of the patient and may further allow for a more precise delivery of ablation energy over a small target area for creation of precise lesions.

In particular, such assemblies, apparatus, and methods may be utilized for treatment of various conditions, e.g., arrhythmias, through ablation under direct visualization. Details of examples for the treatment of arrhythmias under direct visualization which may be utilized with apparatus and methods described herein are described, for example, in U.S. patent application Ser. No. 11/775,819 filed Jul. 10, 2007 (U.S. Pat. Pub. No. 2008/0015569 A1), which is incorporated herein by reference in its entirety. Variations of the tissue imaging and manipulation apparatus may be configured to facilitate the application of bipolar energy delivery, such as radio-frequency (RF) ablation, to an underlying target tissue for treatment in a controlled manner while directly visualizing the tissue during the bipolar ablation process as well as confirming (visually and otherwise) appropriate treatment thereafter.

As shown, bipolar ablation and visualization catheter assembly 50 illustrates one variation where the visualization hood 12 may incorporate a bipolar ablation assembly 52 within and/or along the hood 12. The assembly 50 is further illustrated where bipolar ablation assembly 52 may be coupled or otherwise in electrical communication with power generator 56 (e.g., RF power generator) through deployment catheter 16 and handle 54 via cable 58. Fluid reservoir 60 is also illustrated as being coupled to handle 54 and in fluid communication with hood 12 as well as image display assembly 62 which may be coupled to an optical fiber bundle or to an electronic imaging sensor (e.g., CCD or CMOS imager) positioned within or along hood 12 for visualizing the underlying tissue, as described above.

Figure 7:
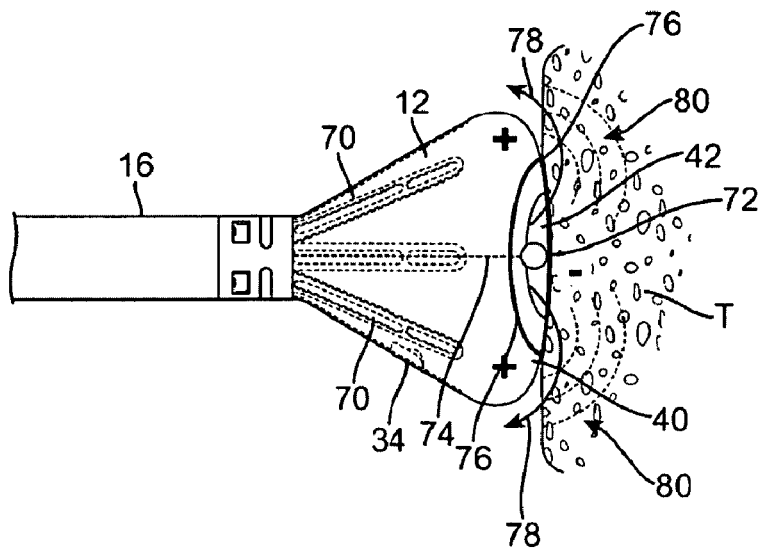
FIG. 7 shows a side view of a visualization hood configured for tissue ablation utilizing a bipolar electrode configuration with a central electrode and a ring electrode.

Bipolar ablation assembly 52 may be configured in a number of different arrangements to effect bipolar ablation of the underlying tissue. One example is shown in the side view of FIG. 7, which illustrates hood 12 having a number of longitudinally oriented support struts 70 therealong and membrane 40 defining aperture 42 over a distal end of hood 12. Imaging element 34 may be positioned along an inner surface of hood 12 to provide imaging the underlying tissue. In this variation, an electrode 72 may extend from catheter 16 via electrode support member 74 and positioned within hood 12, e.g., positioned near or along a central axis of aperture 42 and proximate to or through aperture 42. An electrically conductive electrode ring 76 may be positioned along the membrane 40 and enclose aperture 42. The electrically conductive central 72 and ring electrode 76 may be made from a number of bio-inert materials such as, though not limited to, stainless stain, silver, gold, platinum, etc. Moreover, electrodes 72, 76 may be connected by conductive wires which are insulated by a thin layer of insulation such as PET, latex or other biocompatible polymers.

In use, the visualization hood 12 is placed against or adjacent to a region of tissue T to be imaged and/or ablated in a body lumen that is normally filled with opaque bodily fluids such as blood. Translucent or transparent fluids 78 which are also electrically conductive, such as saline, may be then introduced into the imaging hood 12 until the transparent fluid 78 displaces the blood thus leaving a clear region of tissue T to be imaged via the imaging element 34 before an ablation process. Upon attaining visual confirmation of the target tissue T surface, RF energy may be generated from power generator 56 such that ablation energy 80 is conducted between central electrode 72 and ring electrode 76 via the saline fluid 78 flowing therebetween in effect ablating the underlying tissue. The saline fluid 78 purged from hood 12 and out through aperture 42 may thus serve multiple functions of clearing blood for visualization, conducting ablative energy, as well as optionally cooling the ablated tissue region to prevent tissue charring, desiccation, or other endothelial disruptions such as "tissue popping". Other examples of utilizing energy conductive fluid for tissue visualization and ablation are described in further detail in U.S. patent application Ser. No. 12/118,439 filed May 9, 2008 as well as U.S. Prov Pat. App. No. 60/917,487 filed May 11, 2007, each of which is incorporated herein by reference in its entirety.

Figure 8:
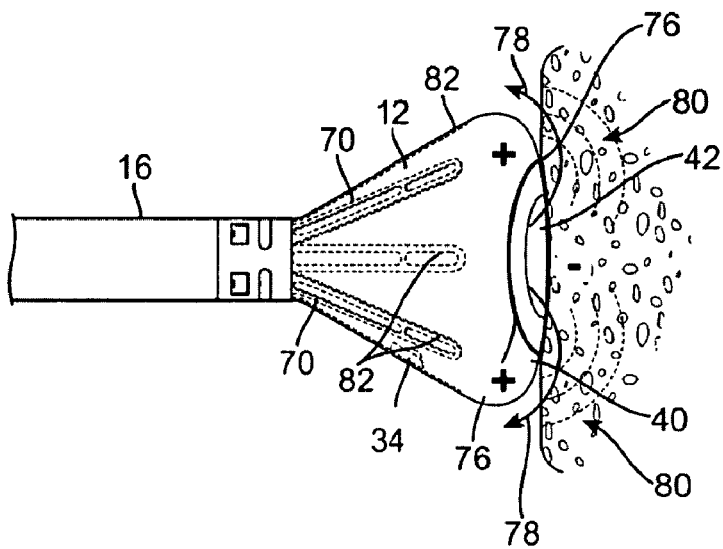
FIG. 8 shows a side view of another variation where a transparent fluid may conduct the charge to or from a ring electrode.

Another variation is illustrated in the side view of FIG. 8, which shows hood 12 having ring electrode 76 positioned on membrane 40 and serving as the return electrode. In this variation, RF energy may be conducted through saline 78 between one or more electrically charged support struts 70, which may have one or more portions 82 exposed along an inner surface of hood 12 in contact with the introduced saline 78, and ring electrode 76. As the saline fluid 78 is introduced into and through hood 12 and aperture 42, the ablation energy is conducted through the saline fluid 78 from the exposed electrode portions 82 and to the return ring electrode 76.

Figure 9:
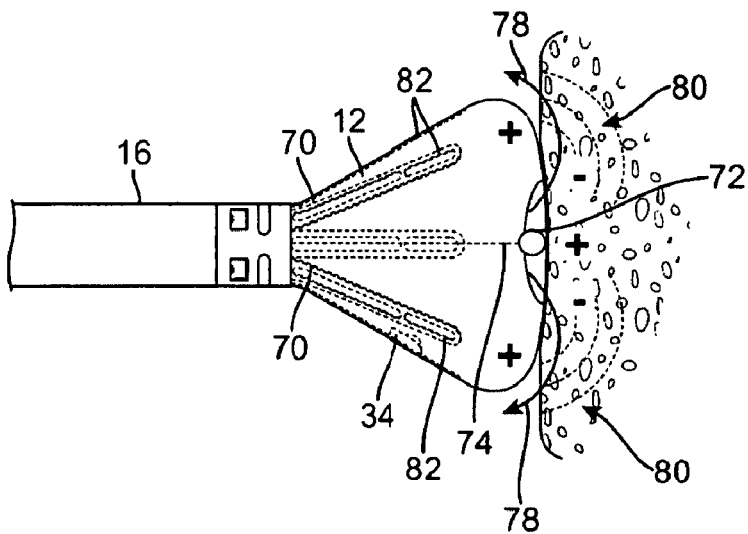
FIG. 9 shows a side view of another variation where a transparent fluid may conduct the charge to or from a central electrode.

In another variation, FIG. 9 shows an example where a centrally positioned electrode 72 may be placed near or at aperture 42, as described above, and instead of utilizing a ring electrode, energy may be conducted through the saline fluid 78 between the exposed portions 82 of electrically charged support struts 70 and electrode 72 to ablate the underlying tissue. In this and other variations described herein, electrode 72 may be comprised at least in part by a transparent casing, e.g., polycarbonate polymers.

Figure 10:
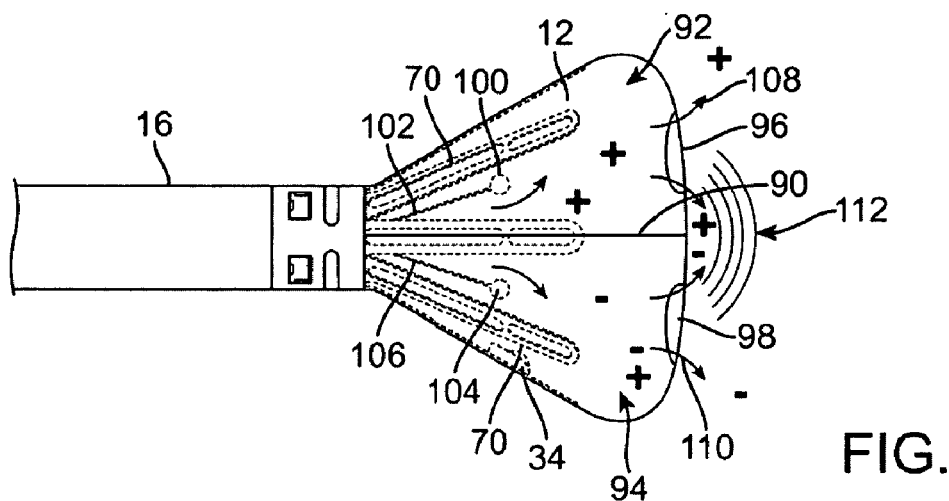
FIG. 10 shows a side view of another variation of a visualization hood having at least two chambers through which transparent fluid conducting a current may flow to effect tissue ablation.

FIG. 10 illustrates a side view of another bipolar electrode arrangement variation where hood 12 may be internally segmented into two or more separated chambers where saline fluid having opposite charges may be introduced into each respective chamber for bipolar ablation. In the variation shown, hood 12 may have first chamber 92 and second chamber 94 divided by septum 90, which may be fabricated from the same material as hood 12 or any other number of electrically non-conductive transparent medical-grade materials, e.g., ChronoFlex™, such that both chambers and the underlying tissue may be visualized via imaging element 34. Each chamber 92, 94 may define a corresponding first and second aperture 96, 98 over the distal membrane and may also each have a corresponding first and second electrode 100, 104 positioned within each respective chamber 92, 94. Each electrode may be positioned within the chambers via respective first and second electrode support members 102, 106. The transparent fluid may be introduced into each chamber 92, 94 past the electrodes 100, 104 such that the charged fluid 108, 110 passing through their respective apertures 96, 98 may contact one another over the tissue to conduct energy 112 therebetween and ablate the underlying tissue.

Figure 11:
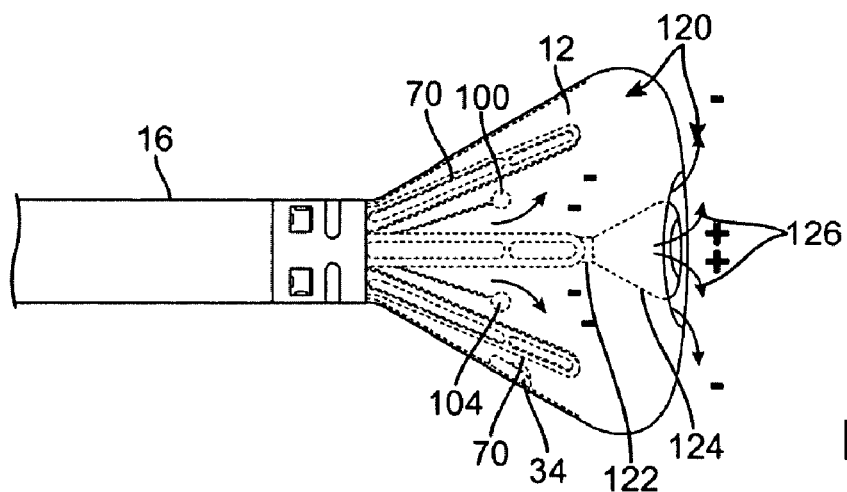
FIG. 11 shows a side view of another variation where a current may be flowed through the transparent fluid flowing between co-axially overlapping hoods.

In another variation, FIG. 11 shows a side view of a hood 12 having a second smaller inner hood 124 positioned within the interior of hood 12. The conductive fluid 120 may be infused into the interior of hood 12 past one or more conductive electrodes 100, 104 and over inner hood 124 and distally through the hood aperture. Fluid may be infused through an inner fluid lumen 122 containing a return electrode such that the fluid 126 infused through lumen 122 and into inner hood 124 may contact the charged fluid introduced into hood 12. When the fluid infused through hood 12 and through lumen 122 come into contact, the underlying tissue may be ablated by the energy conducted through the fluid. In other variations, additional inner hood structures may also be contained by the outer hood for bipolar electrode ablation.

Figure 12A:
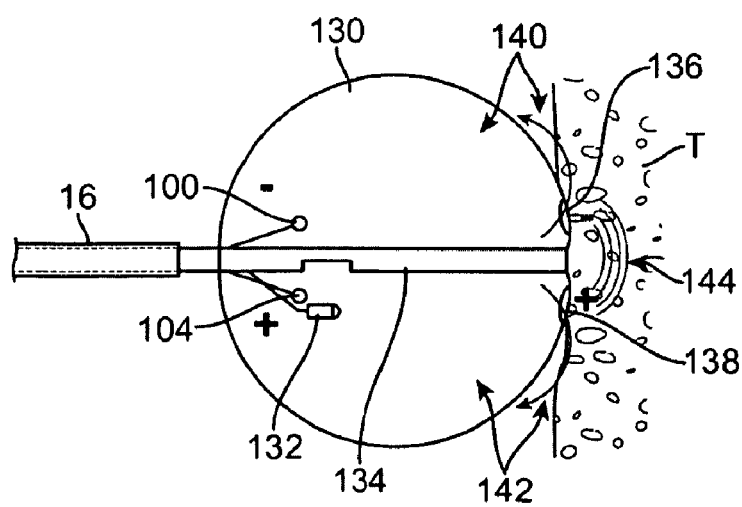
FIG. 12A shows a side view of another variation where an inflatable visualization balloon may have at least two chambers through which transparent fluid conducting a current may flow to effect tissue ablation.

FIG. 12A shows a side view of another variation where hood 12 is replaced by an expandable balloon 130 which may be inflated by the transparent fluid. The balloon 130 may be fabricated from a transparent material to allow for visualization of contacted tissue underlying the balloon 130 by an imaging element 132 positioned within the balloon 130. Additionally, a balloon support member 134 may extend through the balloon from deployment catheter 16 to a distal end of the balloon 130 to provide structural integrity. Optionally, support member 134 can be made from a transparent material, such as polycarbonate, PVC, silicone, etc., in order to provide for unobstructed visualization. The balloon 130 may itself be divided into two or more separate chambers each defining a respective first and second aperture 136, 138 near a distal end of balloon 130. Within each separate chamber, a first and second electrode 100, 104 may be positioned such that the conductive fluid 140, 142 flowing past each respective electrode may conduct ablation energy 144 between the electrodes 100, 104 via the conductive fluid when flowed out of the respective apertures 136, 138 and into contact with the underlying tissue T. By inflating the balloon 130 when it reaches the site of ablation, imaging element 132 can be deployed from a work channel defined in support member 134 to visualize the ablated site throughout the ablation procedure.

Figure 12B:
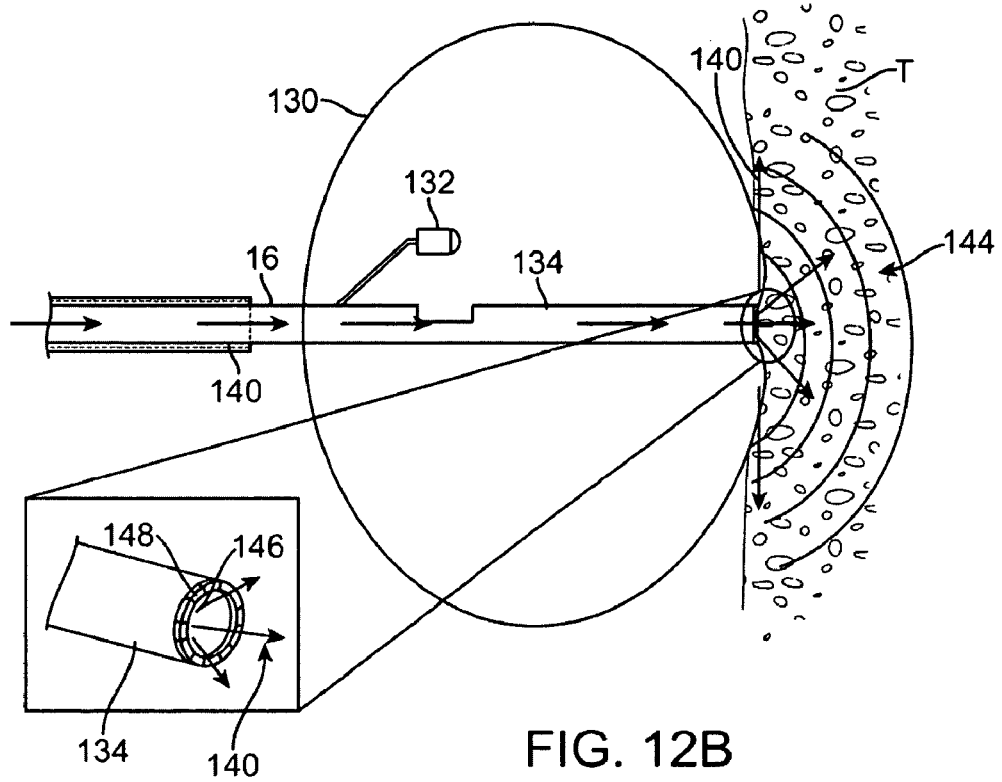
FIG. 12B shows a side view of an inflatable visualization balloon having one or more ring electrodes ablating the underlying tissue while under visualization.

FIG. 12B shows a side view of yet another variation where expandable balloon 130 may have support member 134 define a fluid lumen 146 therethrough. The distal end of lumen 146 which contacts against the tissue surface may define one or more ring electrodes 148 surrounding the opening of lumen 146 for ablating the underlying tissue. A return/ground electrode (e.g., grounding pad) may be utilized for ablation if a monopolar RF modality is used.

Figure 12C:
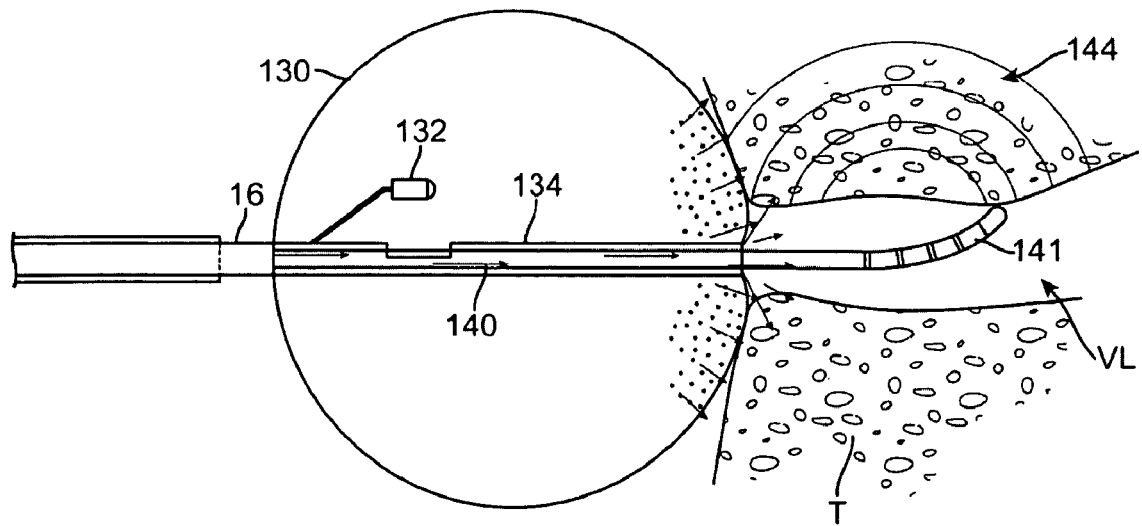
FIG. 12C shows a partial cross sectional side view of the visualization balloon having a porous contact surface and an ablation probe advanced through the balloon.

FIG. 12C shows a side view of another variation where ablation probe 141 may be advanced through the support member 134 lumen and advanced into, e.g., a vessel lumen VL, to contact and ablate the tissue surrounding the vessel opening. The distal surface of the balloon 130 may optionally define a plurality of holes, slits, openings, or apertures (e.g., micro-holes) that allow the purging saline fluid to seep through the balloon membrane. In this variation, the balloon 130 may facilitate cooling of the ablated tissue and increase flow and efficiency of saline purged and may also function to increase the tissue surface subjected to ablation.

Figure 12D:
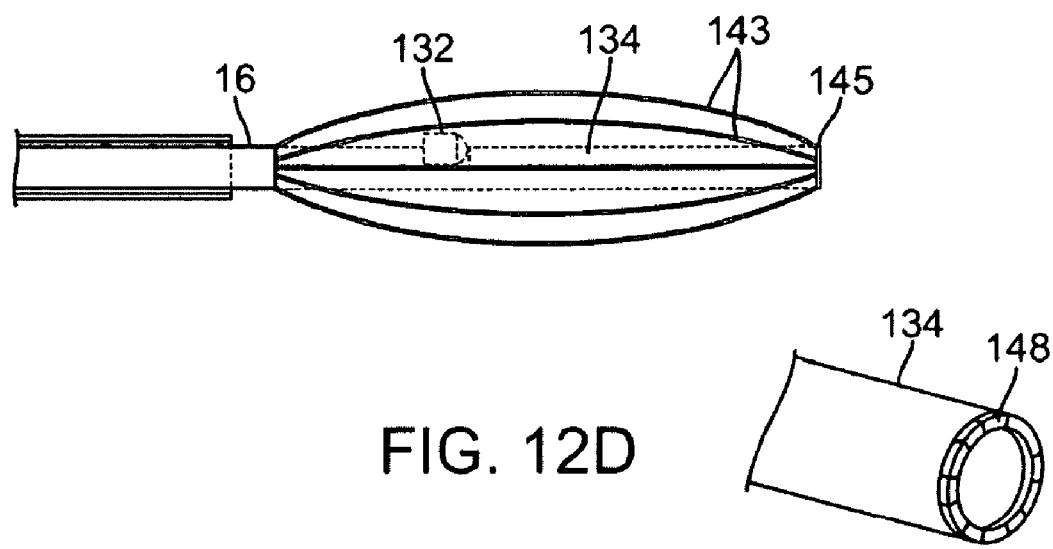
FIGS. 12D and 12E show side views of another variation of a visualization balloon having an ablating ring electrode and which is expandable via mechanical activation in its low-profile and expanded configurations.
Figure 12E:
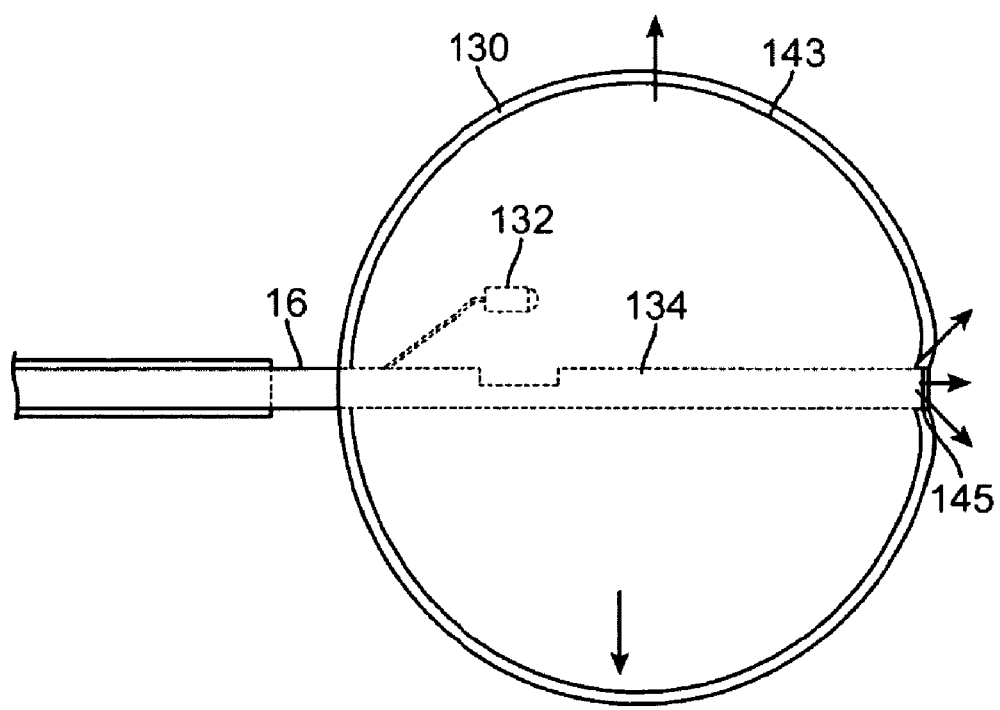

FIGS. 12D and 12E show side views of yet another variation where the visualization balloon 130 may be expanded or deployed by mechanical actuation either alone or in combination with fluid inflation from a low profile delivery shape to an expanded deployment shape, as shown. This particular variation illustrates a number of reconfigurable support members 143 configured as a scaffold or reconfigurable basket frame which is attached along the deployment catheter 16 and at attachment point 145 at a distal end of support member 134. The support members 143 may be made from a shape memory alloy such as Nitinol and may be passively stored in its delivery configuration by compressing the balloon and frame into a sheath. Upon deployment from the sheath, the balloon 130 and/or support members 143 may self-expand. Alternatively, the support members 143 may be made from non-shape memory materials such as stainless steel, tungsten, Elgiloy®, etc. and be actively deployed into its expanded configuration, e.g., compressing the frame longitudinally, or by other push mechanisms known to those skilled in the art. As above, ring electrodes 148 can be attached on the distal circumference of the work channel 134 that is exposed and in contact with imaged tissue. The electrodes 148 can also be used for ablating and/or detecting electrophysiological signals of contacted imaged tissue.

Figure 12F:
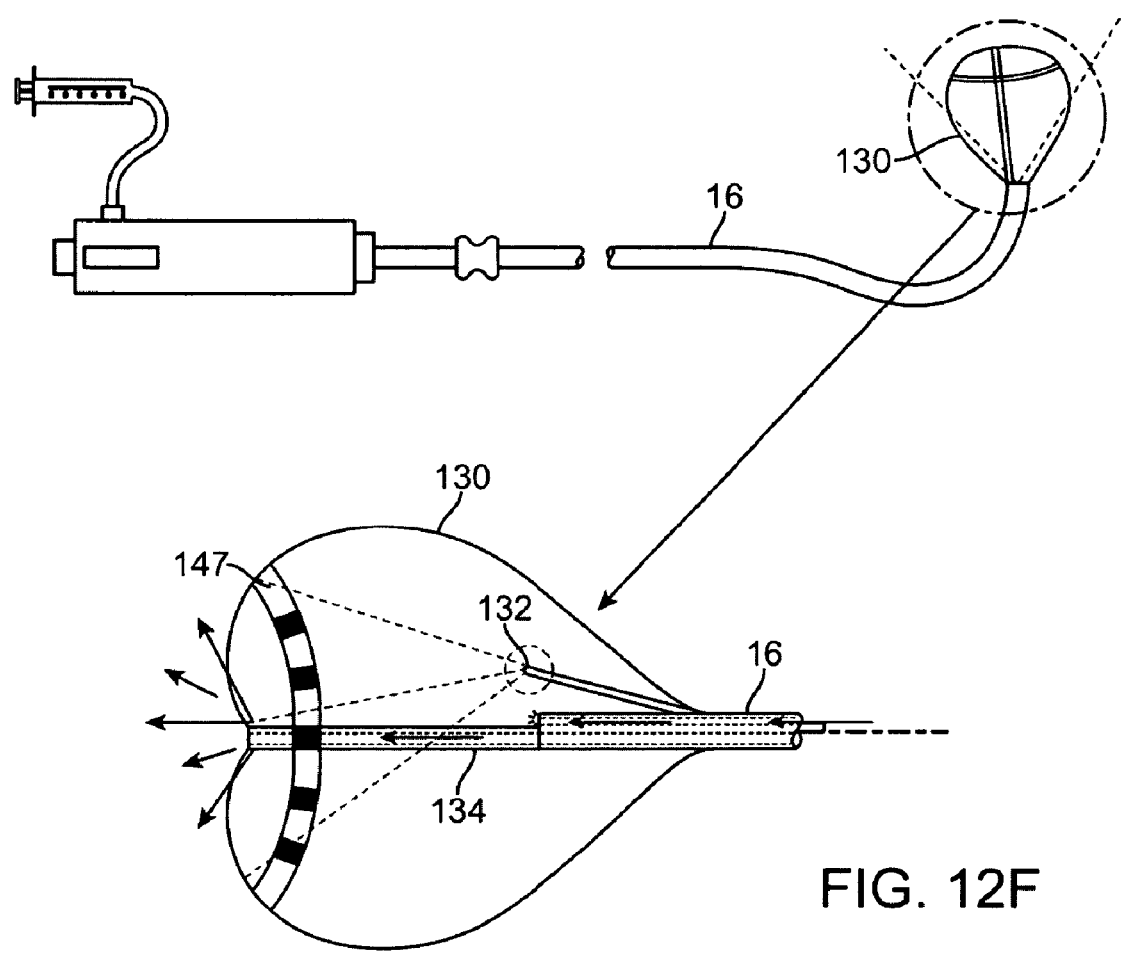
FIG. 12F shows a side view of another variation of a visualization balloon having ablation electrodes on the distal front surface of the imaging balloon.

As illustrated in the side and detail side views of FIG. 12F, electrodes 147 positioned circumferentially about the work channel can also be used for mapping and pacing of electrophysiological signals of tissue in contact with the electrodes. As shown, the electrodes 147 may be alternatively arranged over a distal exterior face of the imaging balloon 130.

Figure 13A:
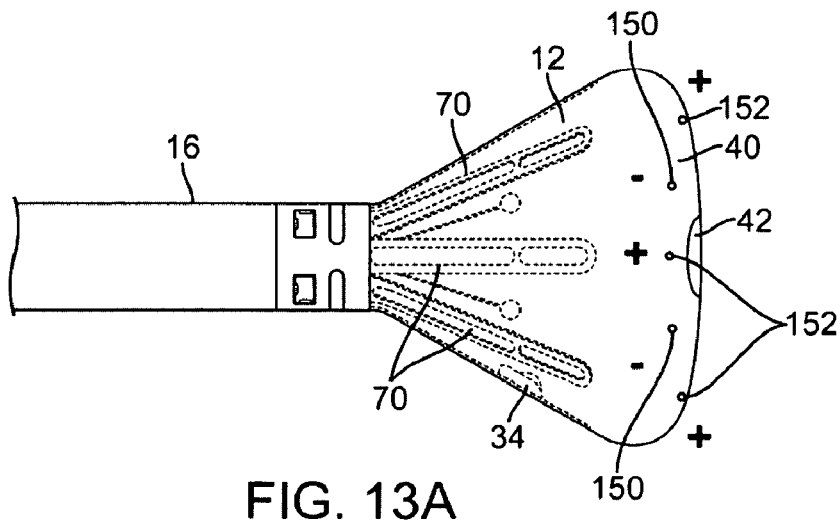
FIG. 13A shows a side view of another variation where a plurality of electrodes configured in a bipolar arrangement may be positioned along a distal membrane of the hood.
Figure 13B:
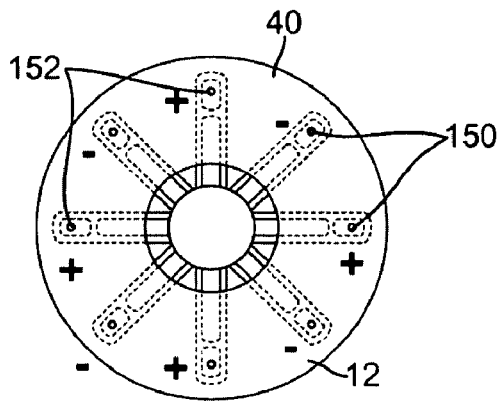
FIGS. 13B and 13C illustrate end views of electrode arrangement variations along the distal membrane.
Figure 13C:
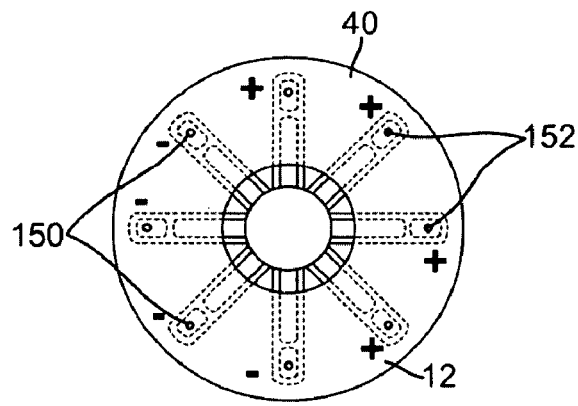
Figure 13D:
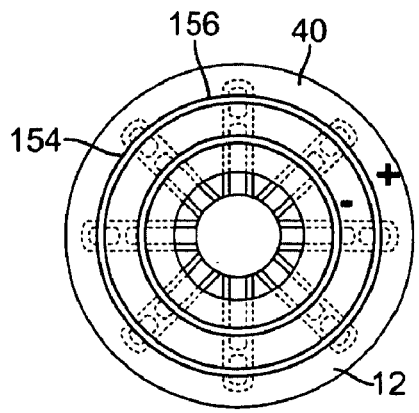
FIG. 13D illustrates an end view of a concentric ring electrodes configured in a bipolar electrode arrangement.

FIG. 13A shows a side view of yet another variation where the distal membrane 40 of hood 12 may have multiple conducting electrodes 150 and return electrodes 152 directly upon the face of membrane 40 for contact against the underlying tissue. The shape and size of the formed lesions can be controlled by the arrangement of bipolar electrodes across the hood membrane 40. In one arrangement shown in the end view of FIG. 13B, oppositely charged electrodes 150, 152 may be placed adjacent to each other in an alternating circumferential pattern over membrane 40. In another variation shown in the end view of FIG. 13C, similarly charged electrodes 150, 152 may be grouped together in a circumferential pattern over membrane 40. Such an arrangement may result in the formation of linear lesions which is normally desirable in ablation procedures. Another bipolar electrode arrangement is shown in the end view of FIG. 13D, which shows a conducting electrode ring 154 and a return electrode ring 156 arranged in a concentric pattern with respect to the aperture over the face of membrane 40. The flow of current passing between these oppositely charged rings 154, 156 may aid in the formation of lesions in the tissue region within the periphery of these ring electrodes. The flow rate of the saline can be regulated from the proximal end of the catheter system if so desired.

Figure 14A:
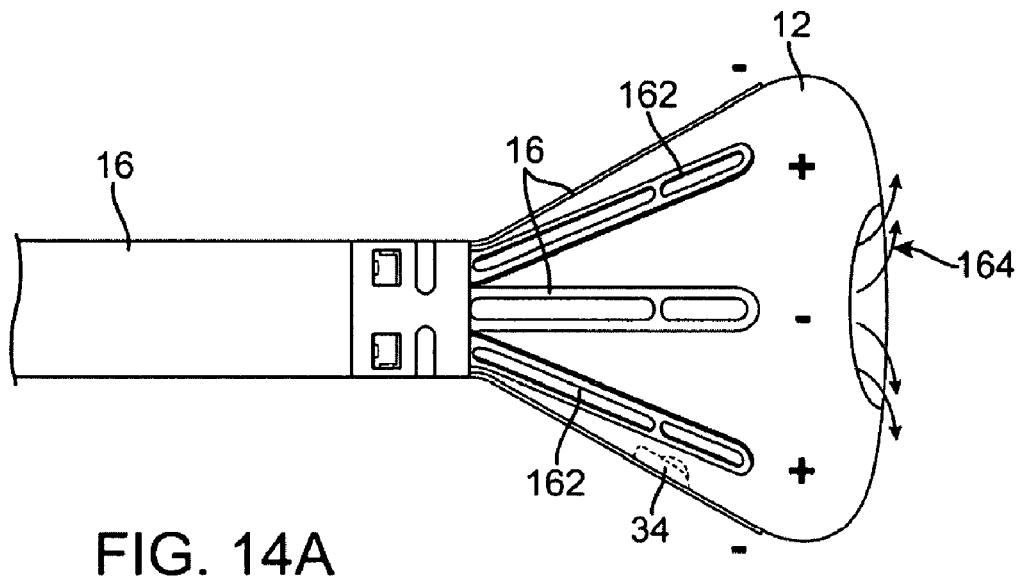
FIG. 14A shows a side view of another variation where one or more support struts serve as electrodes.
Figure 14B:
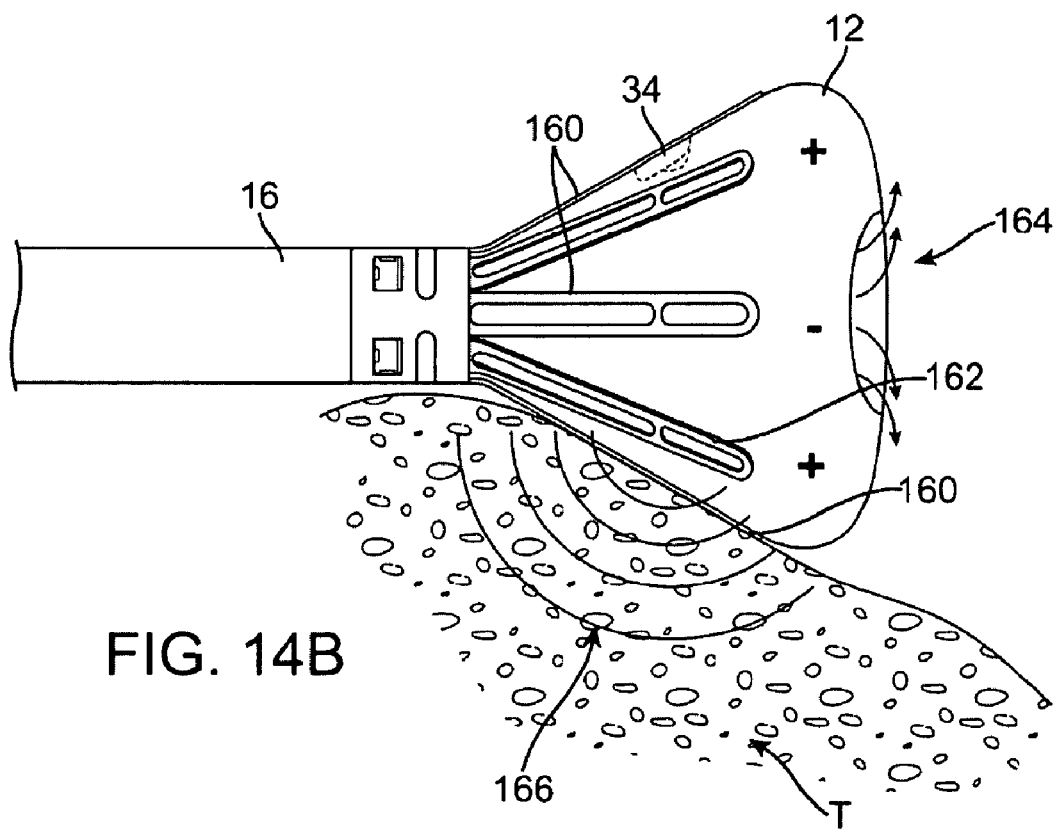
FIG. 14B shows a side view of the variation of FIG. 14A ablating tissue via the one or more support struts.

FIG. 14A shows a side view of another variation where one or more electrically conductive support struts 160 may be function as an electrode to conduct electricity to one or more corresponding return electrode support strut 162. These electrode support struts 160, 162 may be positioned along hood 12 such that they are exposed exteriorly along an outer surface of hood 12. The conductive fluid 164 flowing through hood 12 may flow out of the aperture and around the electrode struts such that energy is conducted between the struts 160, 162. Because of the positioning of the struts along an exterior surface of hood 12, the hood outer surface may be utilized to contact and ablate underlying tissue, as illustrated in the side view of FIG. 14B. The flow of ablation energy 166 through the electrically charged fluid 164 between the struts 160, 162 may result in the formation of lesions on the tissue region under the base of the hood 12 as well as along the side surfaces of the hood 12.

Figure 14C:
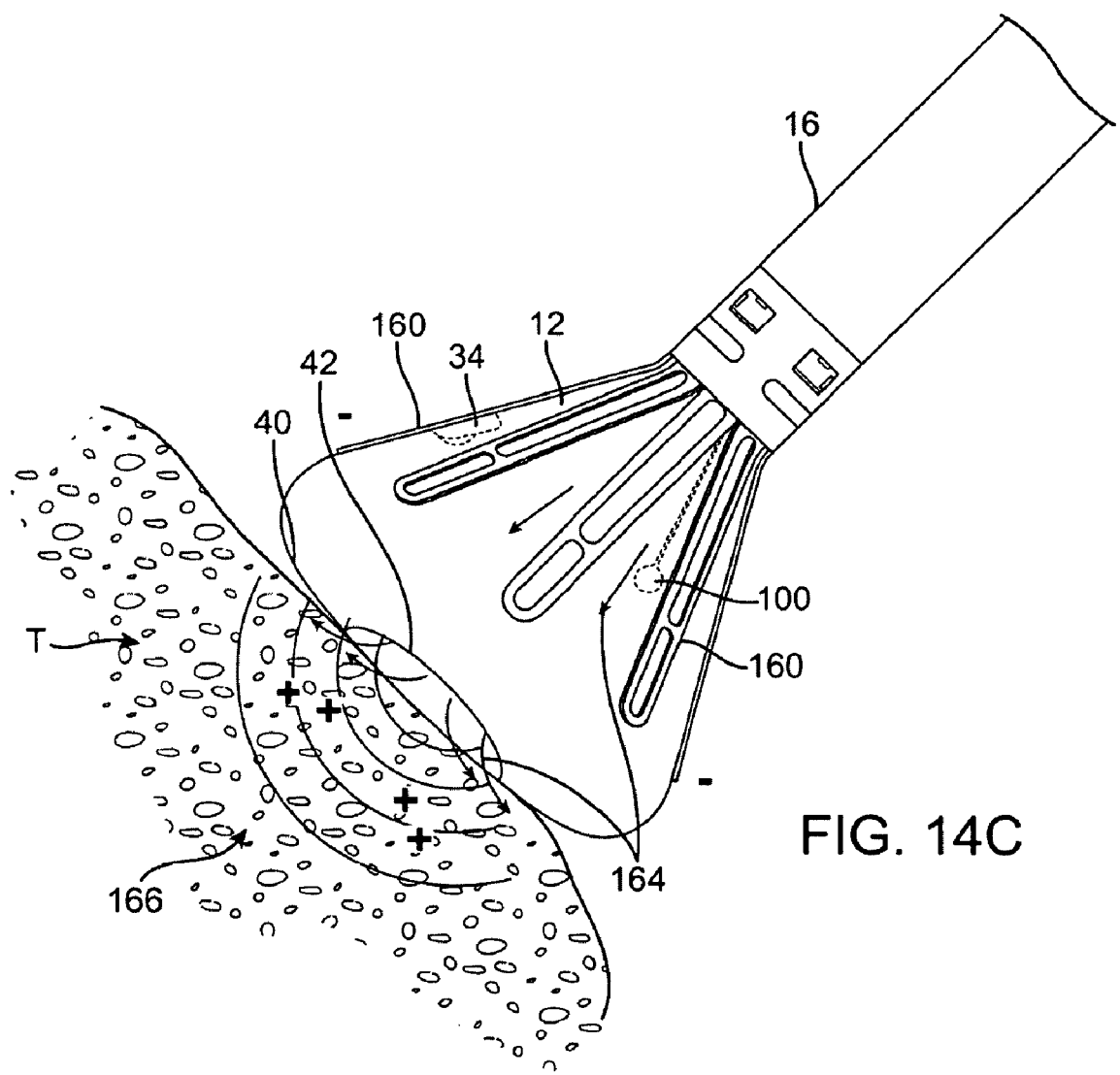
FIG. 14C shows a side view of a visualization hood ablating tissue via energy conducted through the transparent fluid between an electrode within the hood and one or more support struts serving as electrodes.

In yet another variation shown in the side view of FIG. 14C, an electrode 100 may be positioned within hood 12 such that the flow of conducting fluid 164 past the electrode 100 may conduct ablation energy when contacted against one or more support struts 160 configured as a return electrode to ablate the underlying tissue T. The conducting saline fluid 164 may not only purge the hood 12 of blood to facilitate visualization of the underlying tissue but may also be used to potentially cool the ablation area and ensure the formation of uniform lesions on the tissue regions T.

Figure 15:
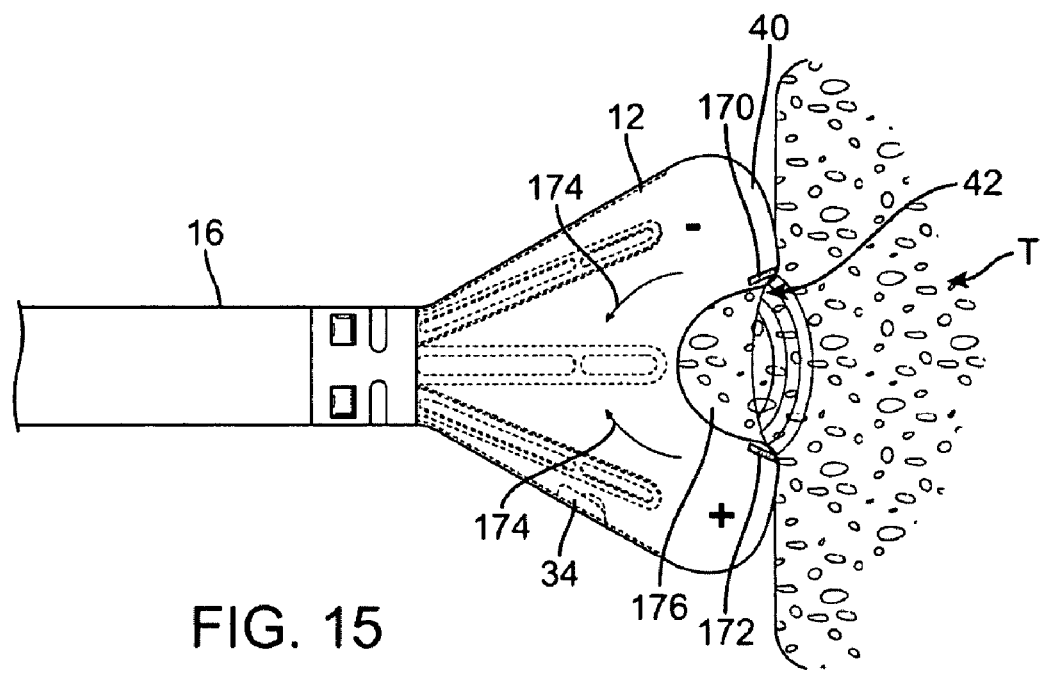
FIG. 15 shows a side view of another variation where tissue drawn partially into the hood through the aperture is ablated between electrodes.

FIG. 15 illustrates a side view of another variation where a portion of tissue 176 under visualization through hood 12 may be drawn at least partially into the interior of hood 12 through aperture 42 by back-flowing the transparent fluid 174 back through a fluid lumen in deployment catheter 16. At least one conducting electrode 170 and at least one return electrode 172 may be positioned about the hood aperture 42 such that the tissue 176 pulled into the hood 12 may be subjected to ablation energy conducted between the two electrodes 170, 172 while under direct visualization from imaging element 34. Such an electrode arrangement may enable lesion formation across the entire depth of tissue 176 in a more efficient and predictable manner as compared to surface ablation.

Figure 16A:
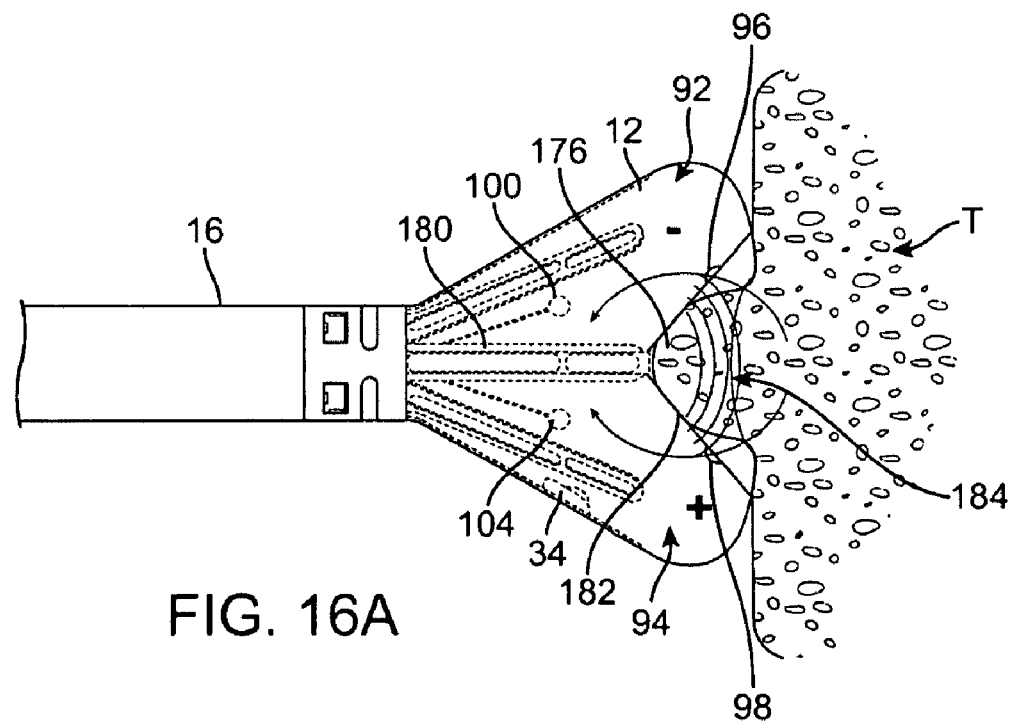
FIG. 16A shows a side view of another variation where tissue drawn between at least two separate chambers may be ablated as current is conducted therebetween.

FIG. 16A illustrates another variation also utilizing suction where hood 12 may be segmented into at least two chambers where each chamber defines a respective aperture 96, 98, as previously described. The targeted tissue T may be adhered via back-flowed saline or via a separate suction lumen 180 to pull a portion of tissue 176 into a working space or theater 182 defined between the apertures 96, 98. Ablation energy 184 may be subsequently conducted through the saline fluid between the respective electrodes 100, 104 positioned within each chamber such that the adhered tissue 176 is ablated through its thickness as well as the underlying tissue T.

Figure 16B:
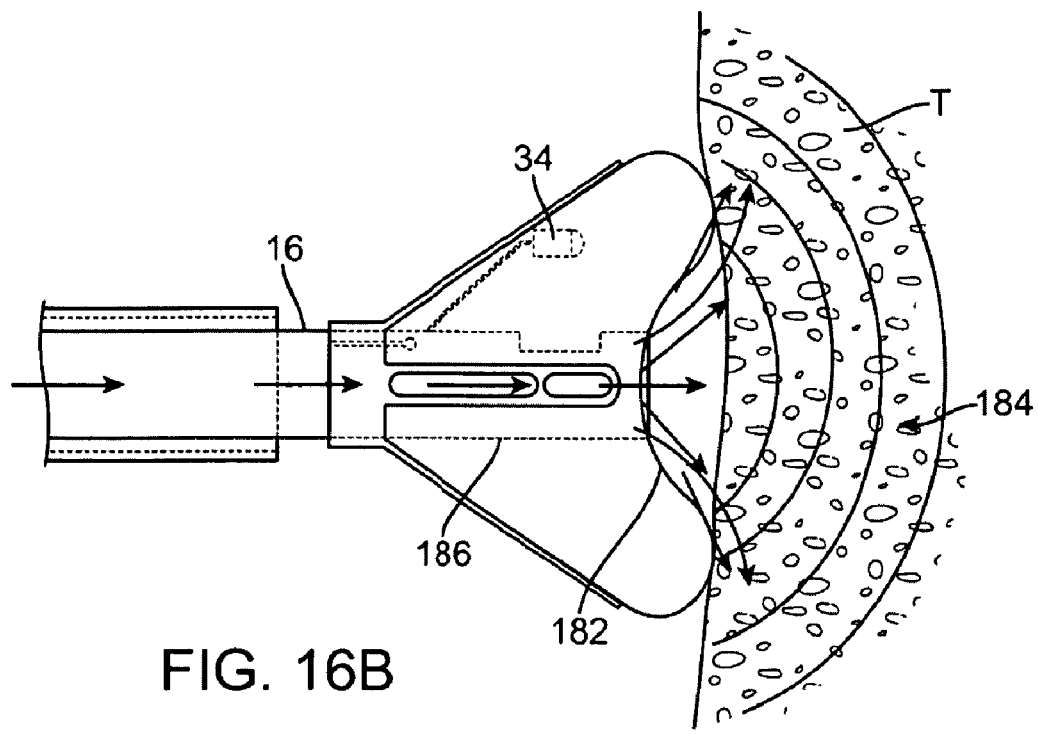
FIG. 16B shows a side view of another variation where the visualization balloon may enclose a working space within which tissue may be ablated.

FIG. 16B illustrates another variation where the expandable member or hood may have a working space or theater 182 defined within in communication with a working channel 186. An electrode may be positioned within the working channel 186 and terminated where the distal end of the electrode is proximity to tissue and in contact with the conductive fluid purged from the work channel. The body of the energy delivery wire can be insulated by a thin layer of insulation such as PET or other biocompatible polymers. At its distal end, the electrode may comprise an exposed electrically conductive probe that can be made from or plated with conductive materials such as stainless stain, Nitinol, copper, silver, gold, or platinum, etc. Saline enclosed within the work space 182 can be energized to ablate the underlying tissue.

Figure 16C:
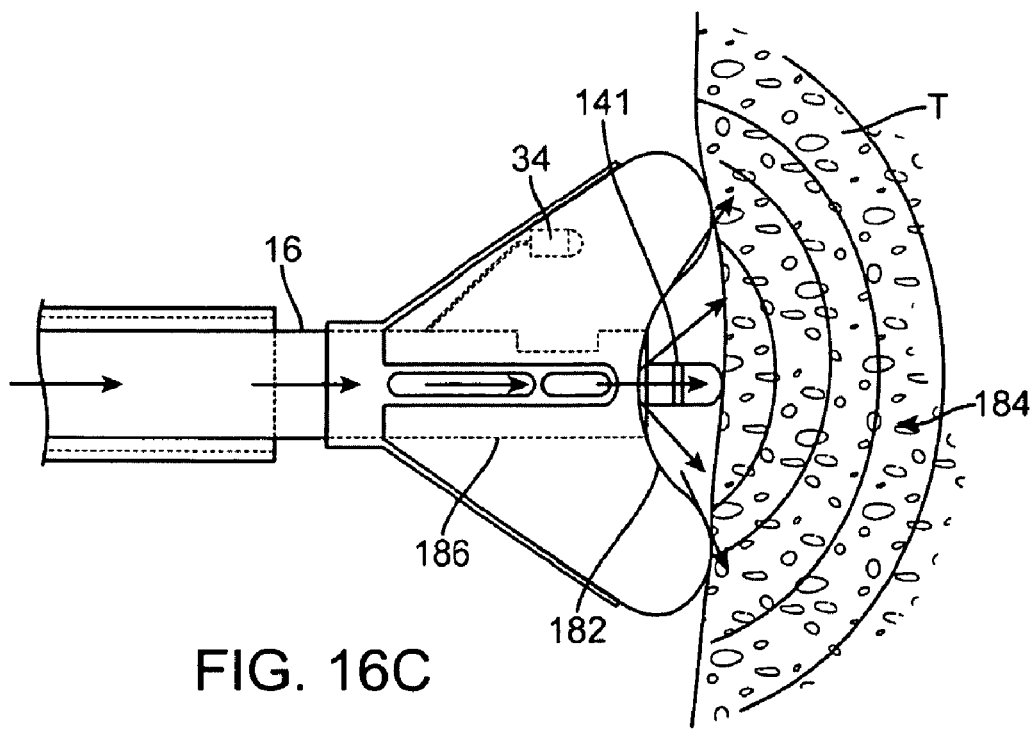
FIG. 16C shows a side view of another variation where an ablation probe may be advanced through a working lumen into contact against tissue bounded within a working space.

As shown in FIG. 16C, shows another variation where ablation may be subsequently performed with an ablation catheter 141, such as RF catheter, on the tissue surface with the purged saline serving multiple functions of visualization, cooling, and conductive medium for creating relatively larger lesions.

Figure 17:
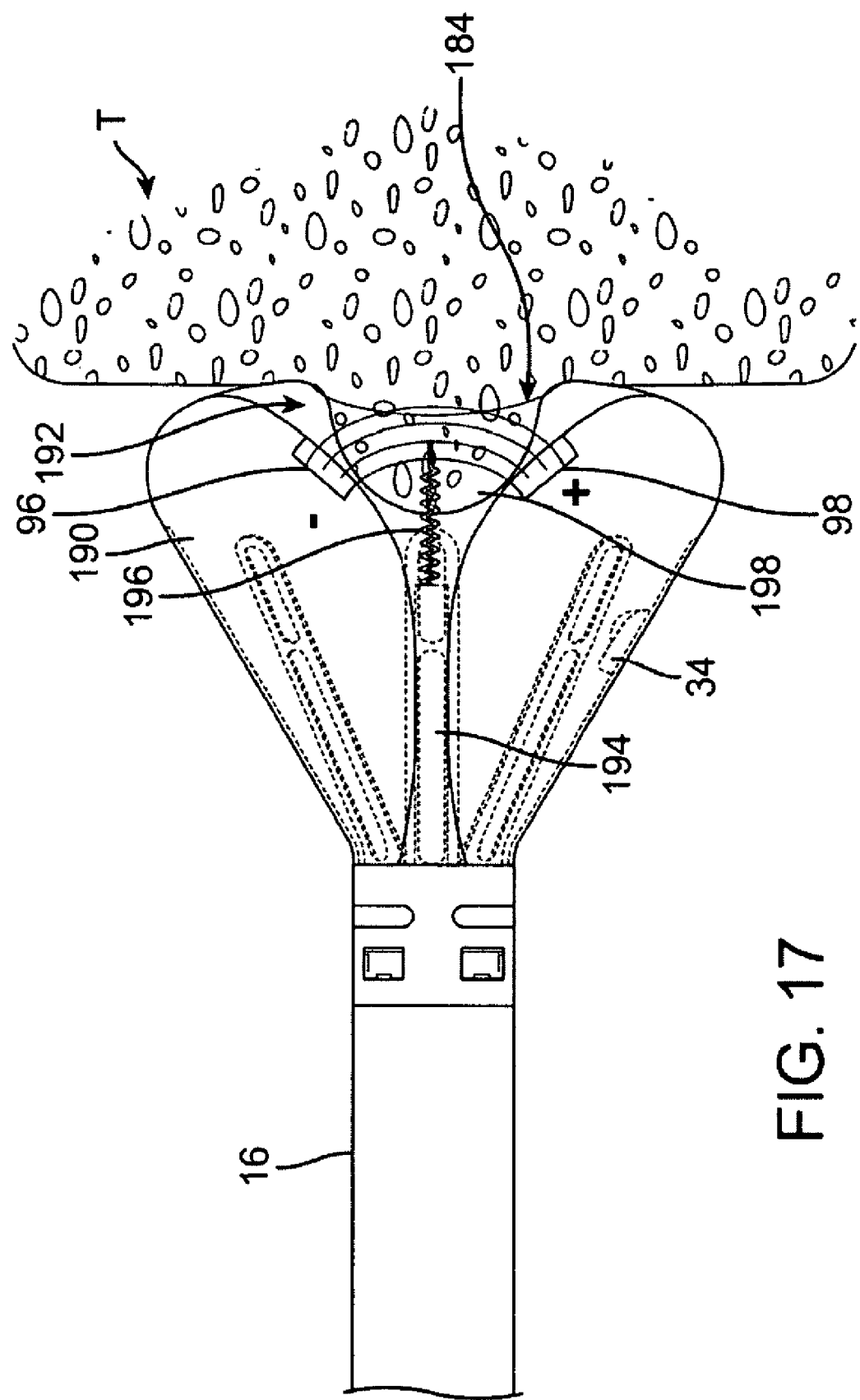
FIG. 17 shows a side view of another variation where tissue drawn between two separate chambers via a tissue grasper may be ablated therebetween.

FIG. 17 shows a side view of yet another variation where hood 12 may be replaced by a toroidal balloon 190 which may be fabricated from a transparent material, as previously described. Toroidal balloon 190 may be tapered to extend radially away from catheter 16 while defining a working space or theater 192 within the balloon interior. A tissue grasper 196, e.g., helical grasper, extending from an instrument shaft 194 may be translatable through catheter 16 and working space 192 such that tissue to be ablated may be engaged by the grasper 196 and pulled proximally into working space 192. The grasped tissue 198 may be brought into contact against electrodes 96,98 positioned about the working space 192 along balloon 190 such that ablation may be effected upon the tissue.

Figure 18:
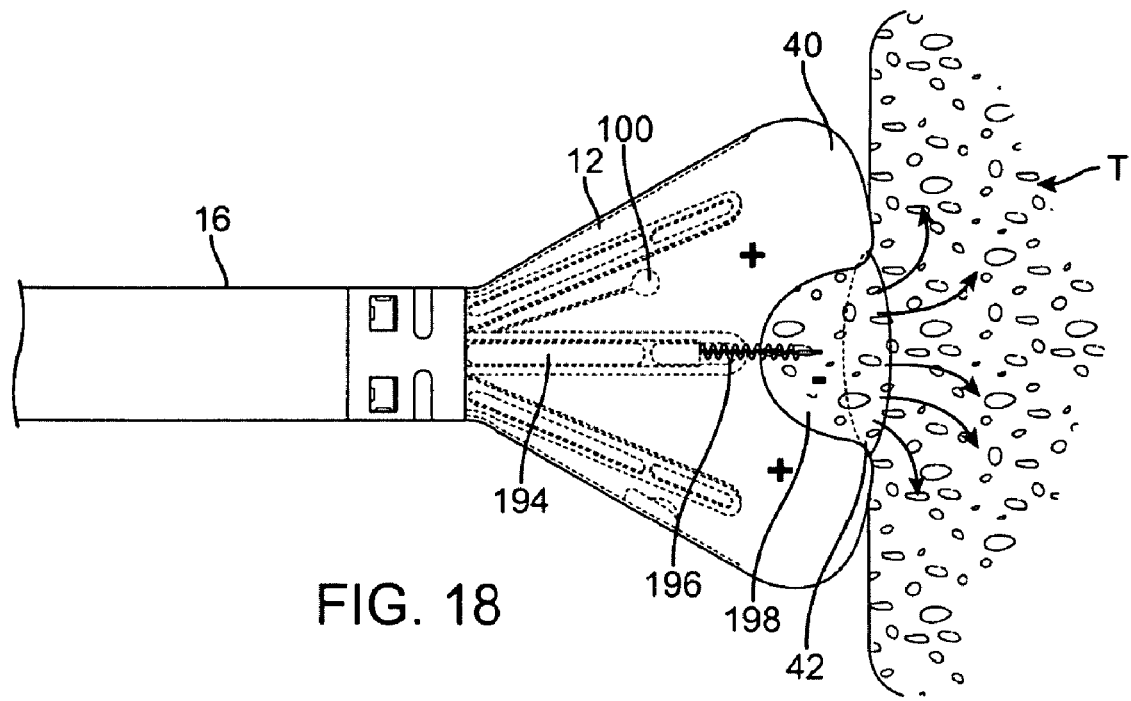
FIG. 18 shows a side view of another variation where tissue adhered to a tissue grasping instrument may be ablated through the instrument.

Another variation is shown in the side view of FIG. 18, which shows a tissue grasper 196 engaging and pulling a portion of tissue 198 to be ablated at least partially into the hood 12 through aperture 42. In this variation, grasper 196 may be configured as an electrode such that ablation energy may be conducted between the grasper 196 and electrode 100 via the saline fluid and through the grasped tissue 198.

Figure 19:
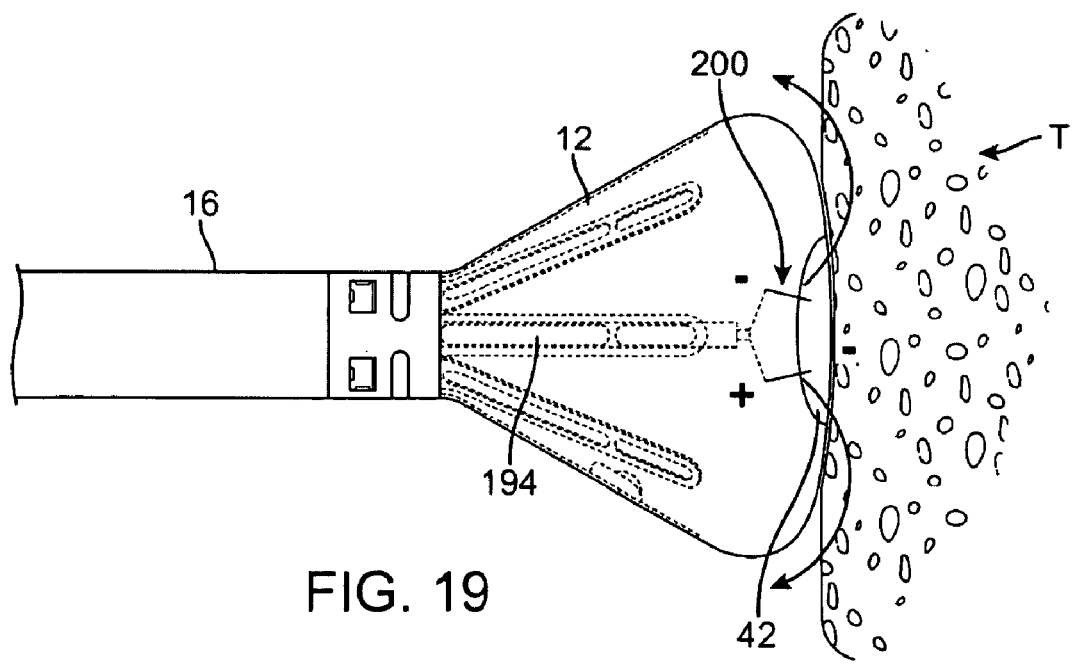
FIG. 19 shows a side view of another variation where a tissue grasper having at least two grasping members may ablate the tissue.

FIG. 19 shows another variation in the side view of an imaging hood 12 having an instrument shaft 194 with a tissue grasper 200 having at least two members configured for engaging tissue and also for functioning as electrodes in a bipolar arrangement. The mechanical action of the grasper 200 enables the engagement of a tissue fold through which ablation energy may be conducted. The members of grasper 200 can be manipulated by applying a push or pull force at the proximal end of the catheter.

Figure 20:
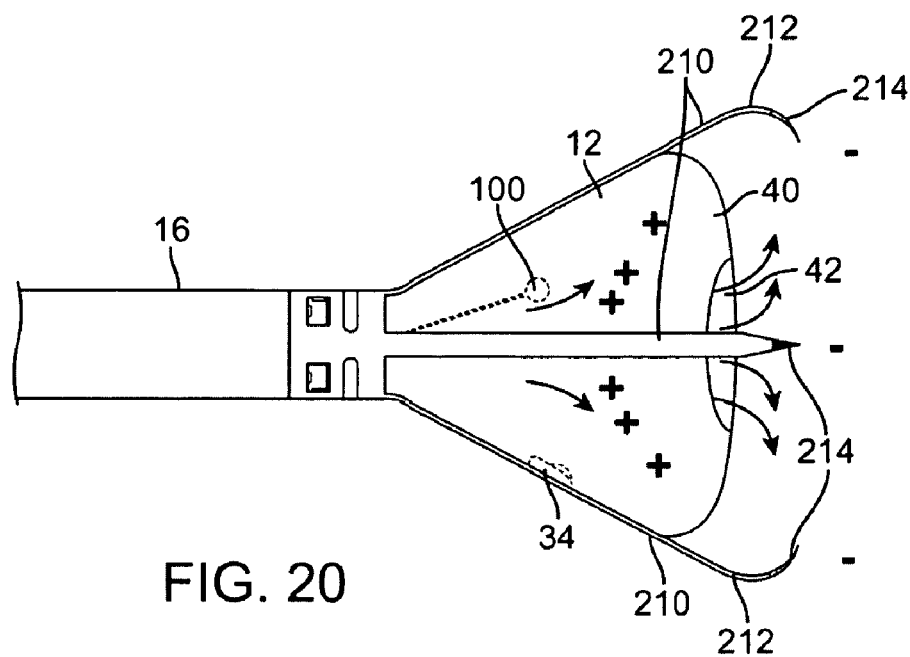
FIG. 20 shows a side view of another variation where one or more distally projecting struts may be employed as electrodes.

FIG. 20 shows yet another variation in a side view of an assembly which may be used to controllably form lesions which are relatively wider than an area of the hood distal membrane 40. One or more electrically conductive struts 210 may have a projecting portion 212 extending distally at an angle from hood 12 and terminating at a conducting tip 214 which may be optionally tapered into a needle-like tissue piercing tip. In use, as the underlying tissue is visualized, as previously described, the one or more conducting tips 214 may be extended distally into the tissue region surrounding the hood 12 contacted against the tissue surface and the conducting fluid may be infused into hood 12 past electrode 100 and through aperture 42 and into the area immediately surrounding hood 12. The ablation energy may be thus conducted between electrode 100 and the one or more conducting tips 214 via the fluid to ablate the tissue therebetween. The conducting tips 214 extended by the projecting portions 212 may thus result in effective and relatively deeper transmural ablation of the tissue area not only directly beneath hood 12 but also the tissue surrounding the hood 12.

Figure 21:
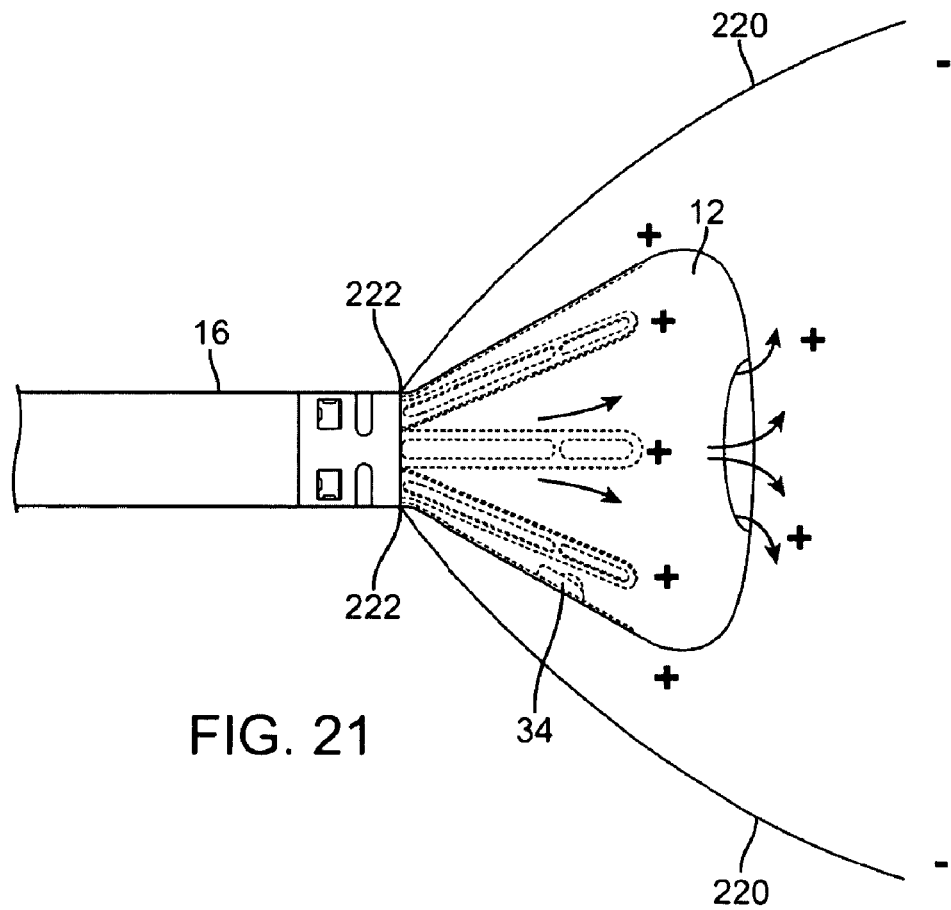
FIG. 21 shows a side view of another variation where one or more distally projecting conducting wires may be employed as electrodes.
Figure 22:
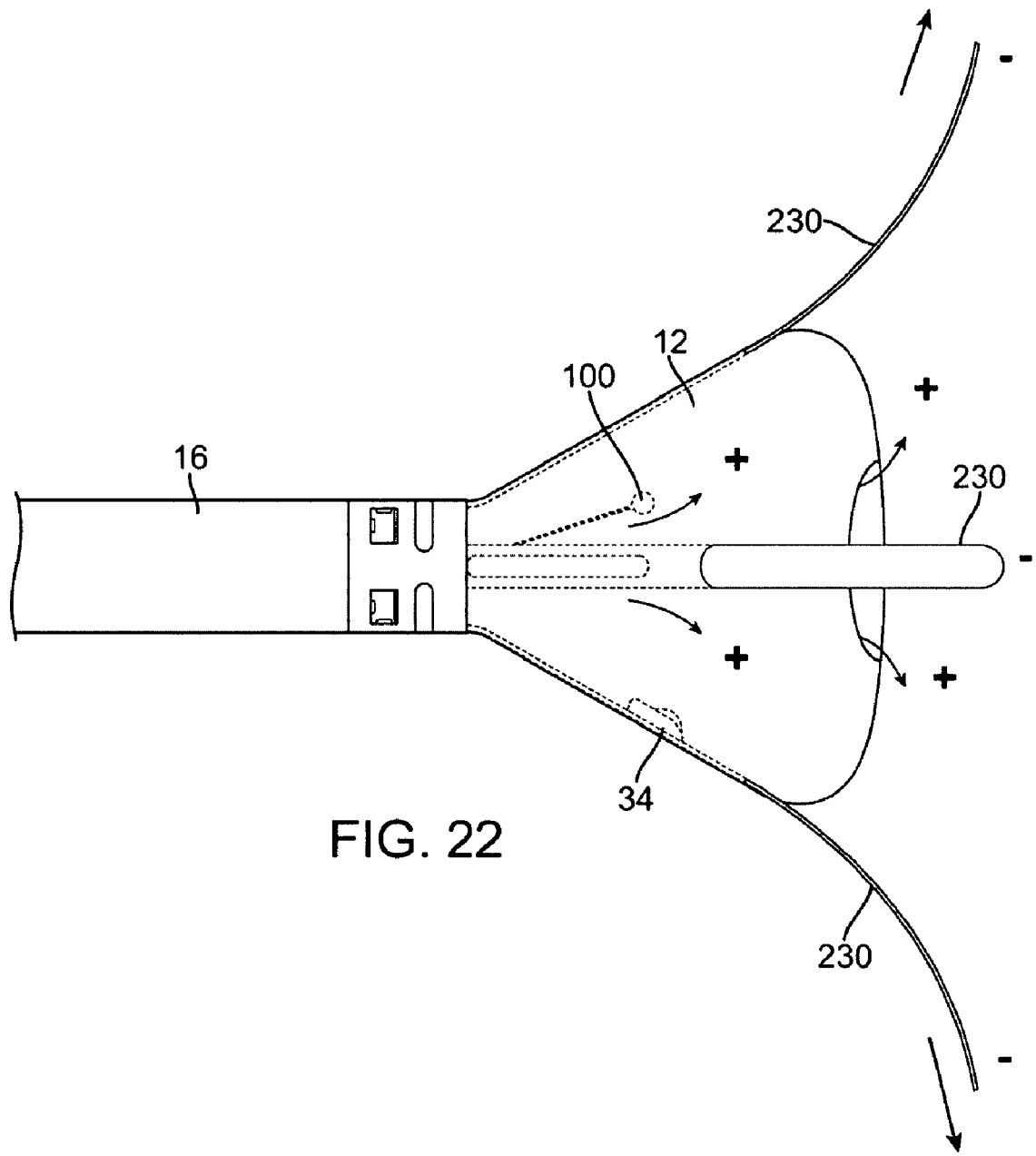
FIG. 22 shows a side view of another variation where one or more distally extendable members may be employed as electrodes.

FIG. 21 shows a side view of an alternative variation where one or more conductive wires 220 may extend distally past hood 12 from attachment points 222 located proximal to hood 12. In a similar manner, the one or more conductive wires 220 may extend linearly or in an arcuate manner distal to hood 12 such that when hood 12 is positioned against a tissue region to be treated, the conductive wires 220 contact the tissue region surrounding the hood 12 to create a lesion pattern extending beyond the hood 12. FIG. 22 shows yet another alternative utilizing one or more distally extendable conducting struts 230 which may be extended from hood 12 such that the struts 230 curve and extend radially from hood 12 within a plane formed by the distal membrane of hood 12. The extendable struts 230 may function as return electrodes for the ablation energy conducted from electrode 100 within hood 12 via the conductive transparent fluid flowing through the aperture. Depending upon the size of desired lesion, the distance which the struts 230 extend from hood 12 can be controlled.

Figure 23:
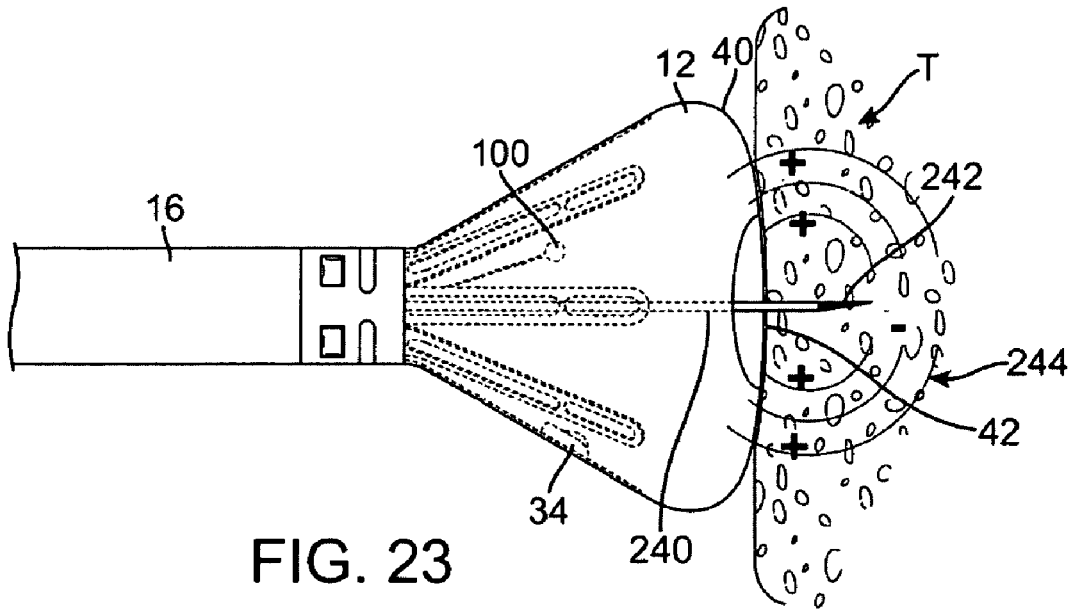
FIG. 23 shows a side view of another variation where a distally projecting needle may be employed as an electrode for tissue ablation.
Figure 24:
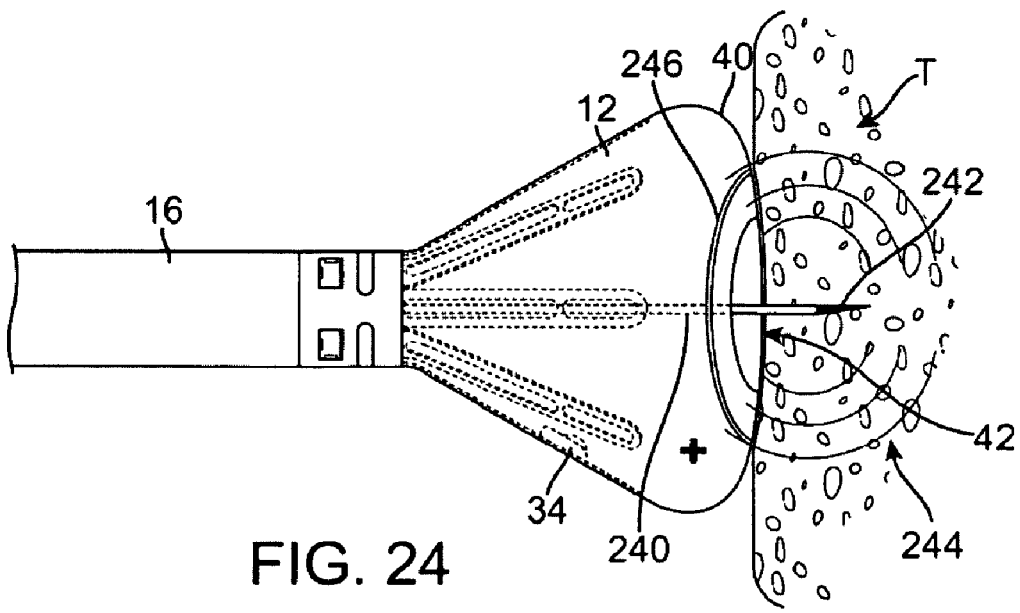
FIG. 24 shows a side view of another variation where a distally projecting needle may be employed with a ring electrode for tissue ablation.

FIG. 23 depicts a side view of another variation where a transmural needle tip advanceable through hood 12 and into underlying tissue T may be used as a return electrode to create relatively deeper lesions. Needle support member 240 may comprise a piercing conductive needle tip 242 which may be advanced through aperture 42 and into the underlying visualized tissue. With electrode needle tip 242 inserted at a predetermined depth into the tissue T, ablation energy 244 may be conducted through the saline between electrode 100 and needle tip 242 to ablate the tissue T transmurally. FIG. 24 shows an alternative variation where an electrode ring 246 may be positioned along the membrane 40 in contact against the tissue surface such that the ablation energy 244 is conducted between electrode ring 246 and needle tip 242 positioned within the tissue T. The conductive saline fluid introduced into the hood 12 may thus serve in aiding in visualization of the tissue, optionally cooling of the tissue region being ablated, and may also serve as a transparent electrode for bipolar electrode ablation between the tissue in contact with the saline and the transmural needle tip 242 penetrated subsurface to the ablation site.

Figure 25:
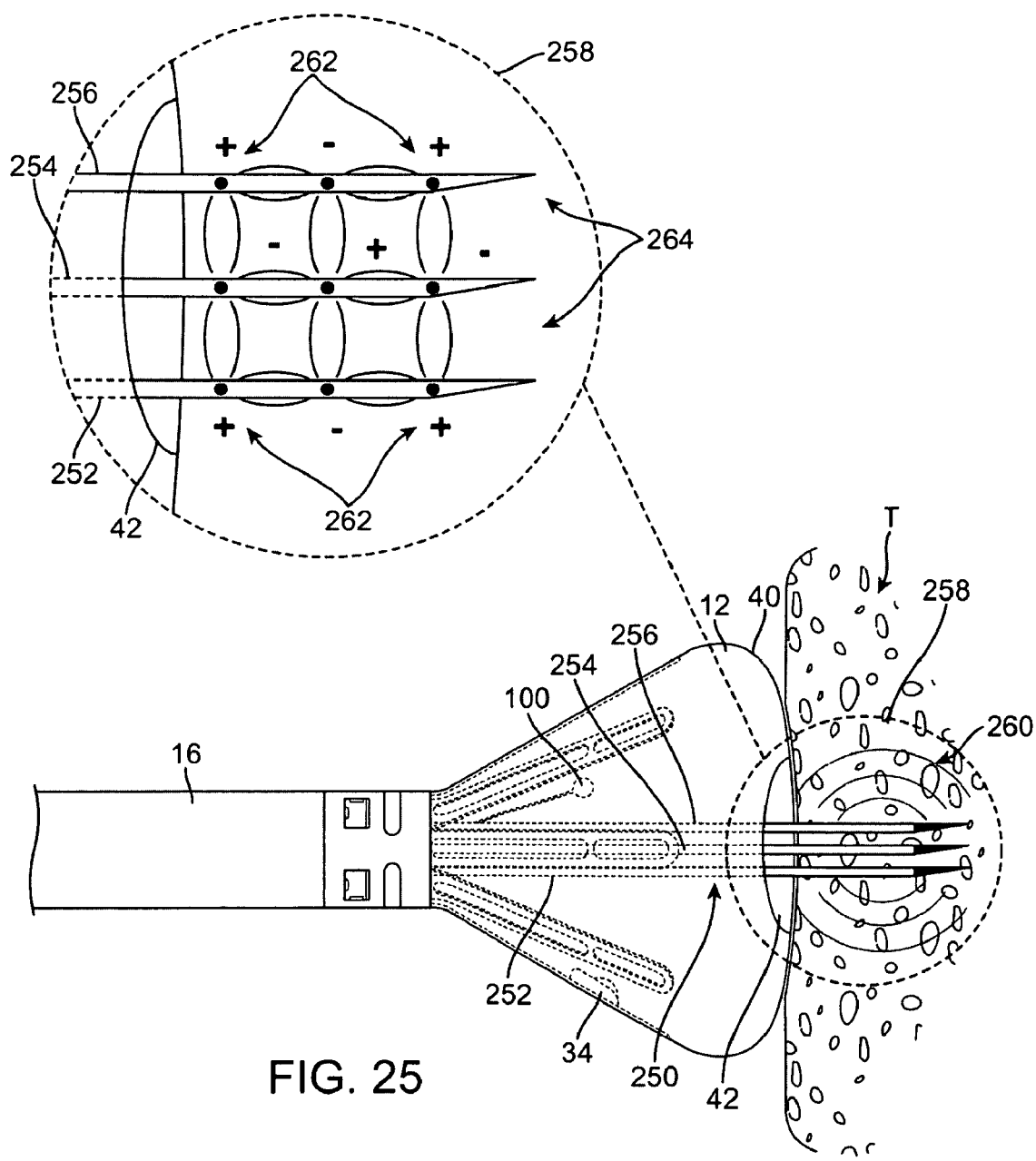
FIG. 25 shows a side view and a detail view of a multiple needle assembly having an arrangement of electrodes along the needle body.

FIG. 25 shows yet another alternative variation where ablation needle assembly 250 having a number of needles 252, 254, 256 (e.g., three in this example although two needles or four or more may also be utilized, as practicable) may be advanced through hood 12 and into the underlying tissue T while positioned adjacent to one another. Each of the needles may have a distal portion, as illustrated in ablation tip detail 258, which comprises a plurality of exposed electrodes 262 at or proximal to the needle tips 264. As the needle assembly 250 is introduced into the tissue while under visualization via imaging element 34, as previously described, energy may be conducted between the exposed electrodes 262 along needle assembly 250 to ablate 260 the tissue T surrounding the needles. The flow of current between the electrodes 262 can result in isolated resistive heating at the specific subsurface tissue region. Further details of transmural needles which may be utilized with apparatus and methods described herein are described in detail in U.S. patent application Ser. Nos. 11/828,267 filed Jul. 25, 2007 (U.S. Pat. Pub. No. 2008/0033290 A1) and 11/775,837 filed Jul. 10, 2007 (U.S. Pat. Pub. No. 2008/0009747 A1), each of which has been incorporated herein by reference above.

Figure 26:
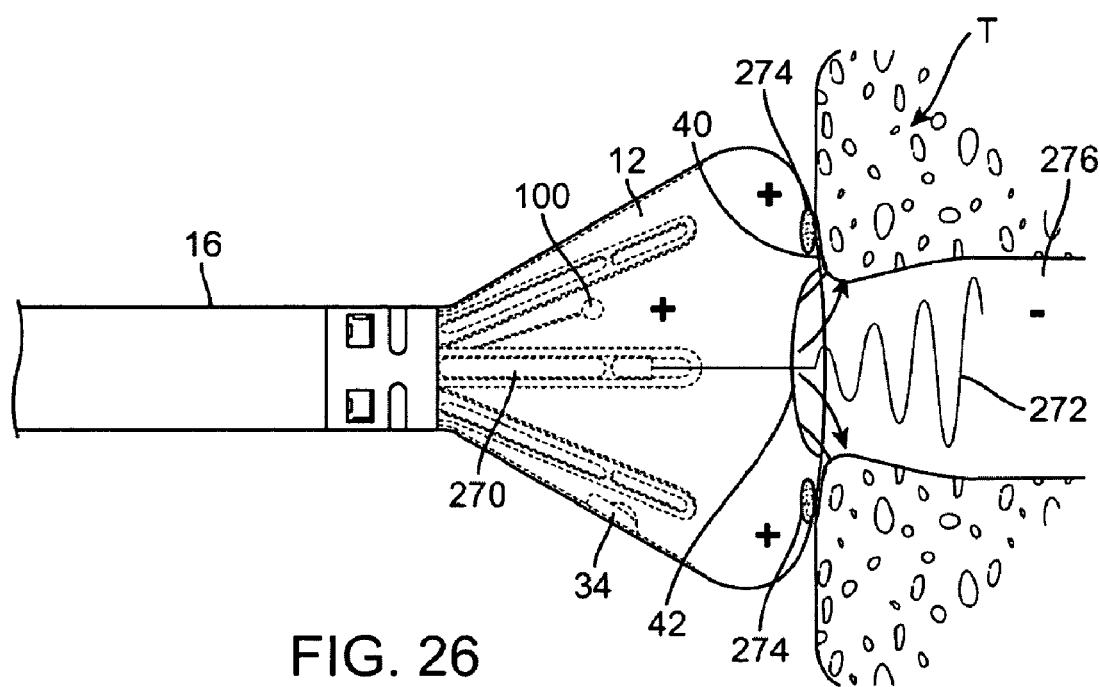
FIG. 26 shows a side view of a another variation where a distally protruding anchor member may be utilized as an electrode for tissue ablation.

FIG. 26 shows yet another example in the side view illustrating hood 12 utilized with an anchoring member 272, e.g., a helical anchor, extendable via an instrument support member 270 which may also be configured as an electrode. For example, anchoring member 272 may be comprised of a wire member made of gold or silver coated Nitinol. Examples of helical anchoring members and methods of use are described in further detail in U.S. patent application Ser. No. 11/959,158 filed Dec. 18, 2007 and U.S. Prov. Pat. App. 60/870,598 filed Dec. 18, 2006, each of which is incorporated herein by reference in its entirety. In this example, anchoring member 272 may be advanced in a low-profile into a vessel lumen 276, such as a lumen of a pulmonary vein, and expanded to temporarily engage the vessel walls. The circumference of membrane 40 in contact against the lumen ostium may comprise one or more return electrodes 274 such that when the electrodes are energized, current may flow between the electrodes via the saline fluid flowing past to ablate the surrounding tissue region T while under direct visualization, e.g., via imaging element 34.

Figure 27B:
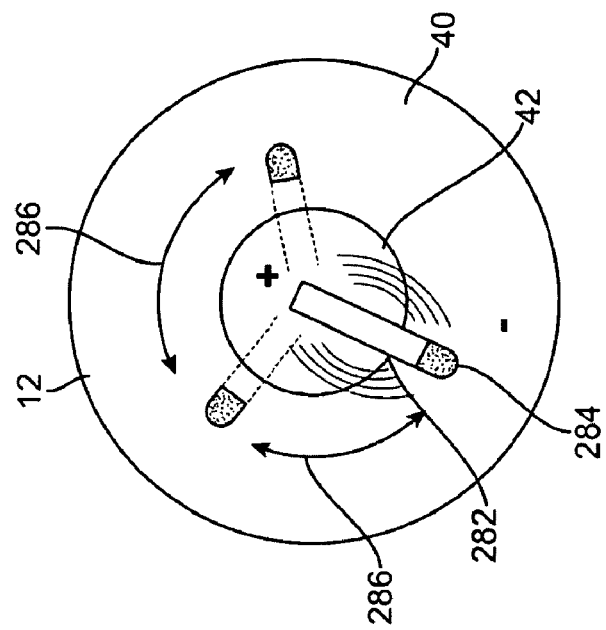
FIGS. 27A and 27B show side and end views, respectively, of a rotatable member utilized as an electrode for bipolar ablation.
Figure 27A:
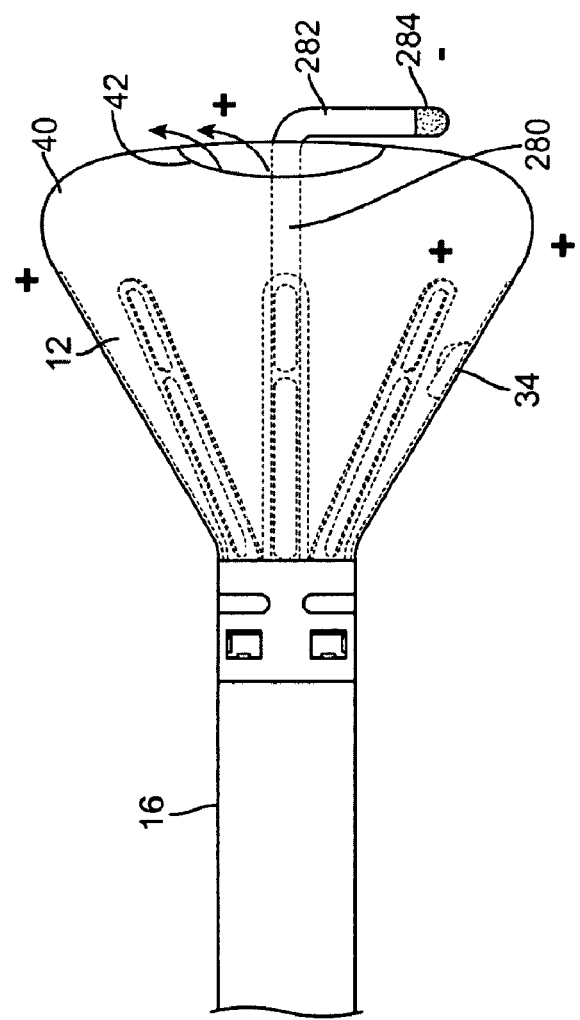

FIGS. 27A and 27B show side and end views, respectively, of another variation where current may flow between an ablation instrument extending through hood 12 having an electrode support member 280 with an angled portion 282 and at least one conducting electrode 284 positioned near or at a distal end thereof. Electrode 284 may be rotatable about a longitudinal axis of support member 280, as indicated by the direction of rotation 286, to facilitate placement of the electrode 284 over the underlying visualized tissue for optimizing ablation. One or more support struts along hood 12 may be configured as an electrode such that the ablation current may be conducted through the saline fluid between electrode 284 and the one or more electrodes of the support struts.

Figure 27C:
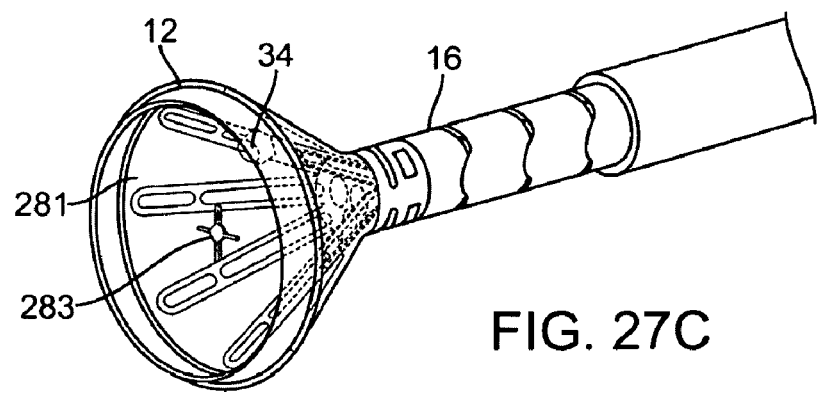
FIG. 27C shows a perspective view of a tissue visualization hood defining an expandable aperture over its distal membrane.
Figure 27D:
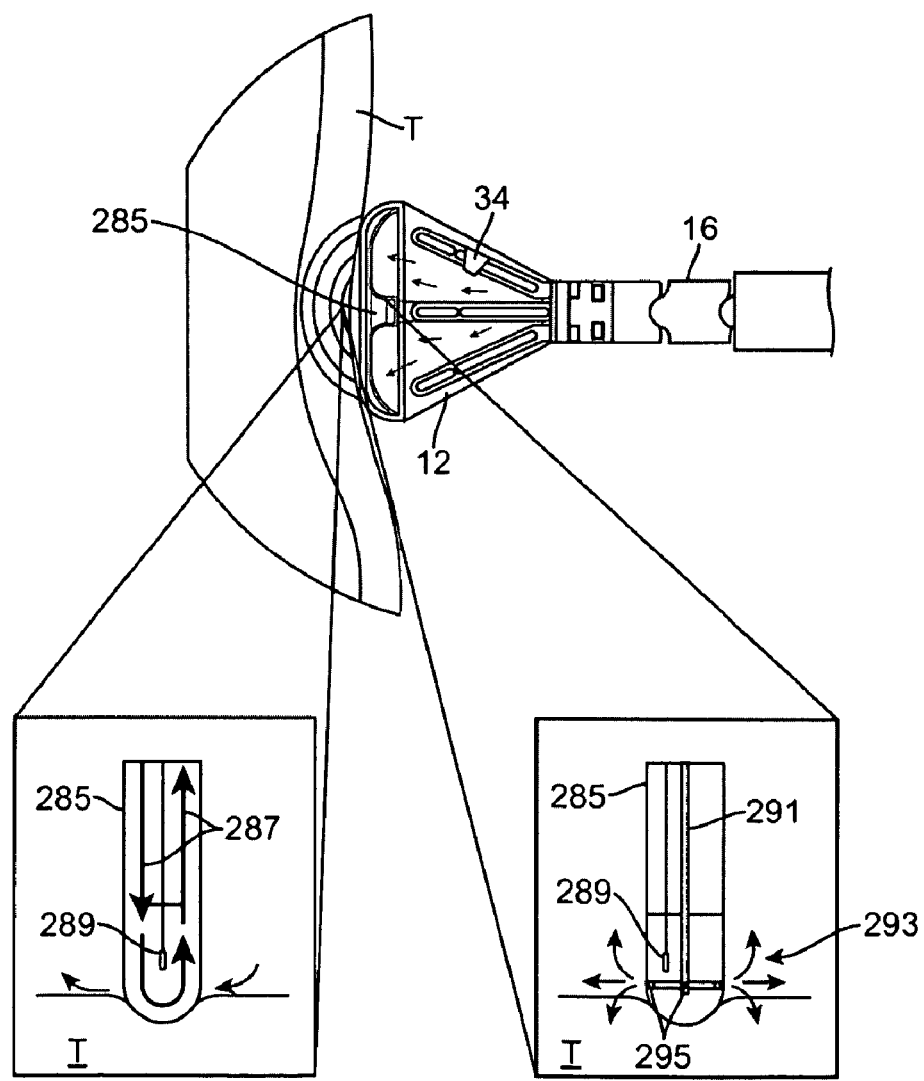
FIG. 27D shows a side view of the apparatus of FIG. 27C having an ablation probe advanced distally through the expandable aperture.

FIGS. 27C and 27D show perspective and side views of yet another variation where hood 12 may define a distal membrane 281, as previously described, which defines an expandable aperture 283, where in this example, may define a multi-slit opening which is sized to narrowly allow for the passage of an instrument therethrough (such as an ablation catheter 285. Once the ablation catheter 285 has been advanced through aperture 283, flow of the purging visualization fluid may remain restricted from flowing therethrough due to the interference between the aperture 283 and outer surface of the ablation catheter 285.

Examples of ablation catheters are shown for illustrative purposes where in one example, the catheter 285 may have a circulating coolant 287 flowing through in a circulating flow pattern. The catheter in this example may include a 7 Fr, 4 mm electrode having a fluid of 5% dextrose circulating at 36 ml/min therethrough. A thermocouple 289 may be positioned within for detecting the electrode temperature. Another example is illustrated where the catheter may define an infusion lumen 291 through which a cooling fluid 293 (e.g., a 7.5 Fr, 3.5 mm electrode with 0.9% NaCl saline infusion) may be flowed through. The electrode distal end may define one or more irrigation lumens 295 through which the cooling fluid may be infused for contacting the underlying tissue (e.g., 6 irrigation holes each having a 0.4 mm diameter). Examples of such ablation catheters may include, though not limited to, commercially available instruments such as the THERMOCOOL® Irrigated tip catheter (Biosense Webster, Inc.), Chilli II™ Cooled Ablation Catheter Boston Scientific, Inc.), or the Cool Path™ Irrigated Tip Ablation Catheter (St. Jude, Inc.). Other configurations may alternatively include the use of a one-way valve in place of the aperture 283 and the use of multiple circumferential balloons attached on the inner wall of the hood inflated around the ablation catheter to isolate saline from ablated tissue.

Figure 28:
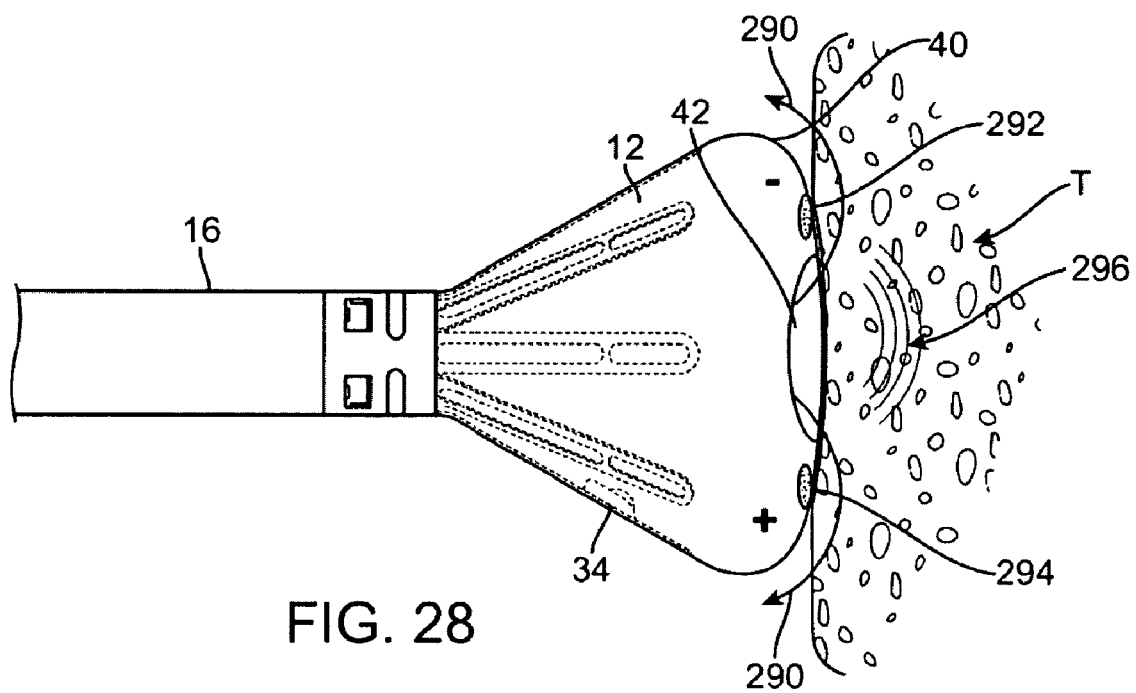
FIG. 28 shows a side view of another variation where hyposaline or chilled saline may be used to reduce or control the conductivity of the fluid for tissue ablation.

FIG. 28 shows a side view of yet another variation where hood 12 may be configured with electrode 292, 294 arranged over the membrane 40, as previously described. In this variation, or in any of the other configurations described herein, the salinity and/or temperature of the saline fluid may be controlled or altered to affect the conductivity of the saline fluid. For example, a transparent fluid 290 having its salinity altered (e.g., hyposaline fluid having a salt concentration less than 0.9%) may be introduced through hood 12 to reduce the conductivity of the fluid 290 and to accordingly adjust the ablation energy 296 through the tissue T. Additionally and/or alternatively, a temperature of the fluid 290 may also be altered to further control a conductivity of the fluid (e.g., saline fluid having a temperature of 20° C.). Moreover, the use of a hyposaline fluid 290 (and/or optionally reduced in temperature relative to body temperature) may reduce the conductivity of the surface of the ablated tissue region to potentially increase the depth of the ablated lesion as higher power and/or longer ablation durations can be applied without charring, desiccating, or causing endothelial disruption to the tissue surface. This can be applied with both monopolar and bipolar electrode arrangements.

Figure 29A:
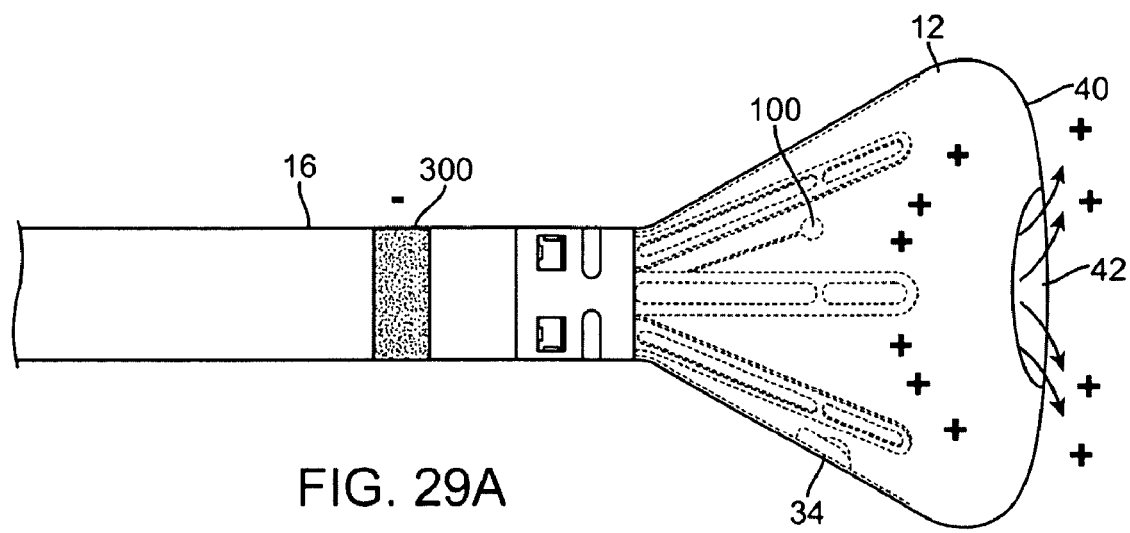
FIGS. 29A and 29B show side views of a return electrode positioned optionally along the deployment catheter shaft and the sheath, respectively.
Figure 29B:
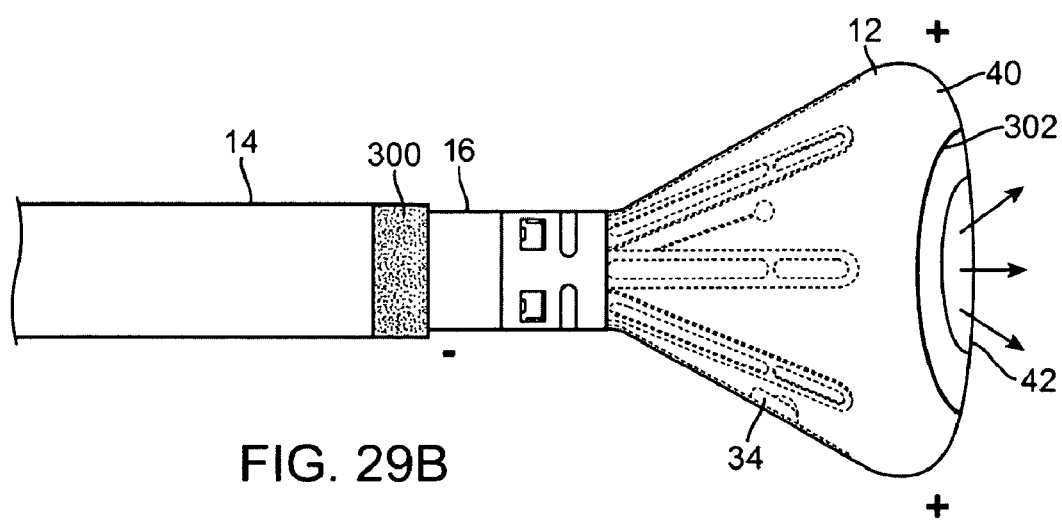

FIGS. 29A and 29B show side views of additional variations where a return electrode may be positioned externally and proximally to hood 12. In the example of FIG. 29A, return electrode 300 may be positioned proximal to hood 12 along a portion of the deployment catheter 16 while in the example of FIG. 29B, return electrode 300 may be positioned proximal to hood 12 along the outer sheath 14, in which case a position of the electrode 300 may be adjusted by movement of the sheath 14 and/or catheter 16 relative to one another. The example in FIG. 29B also illustrates the use of an electrode ring 302 positioned about aperture 42 over membrane 40, although other electrode variations may be utilized.

Figure 30:
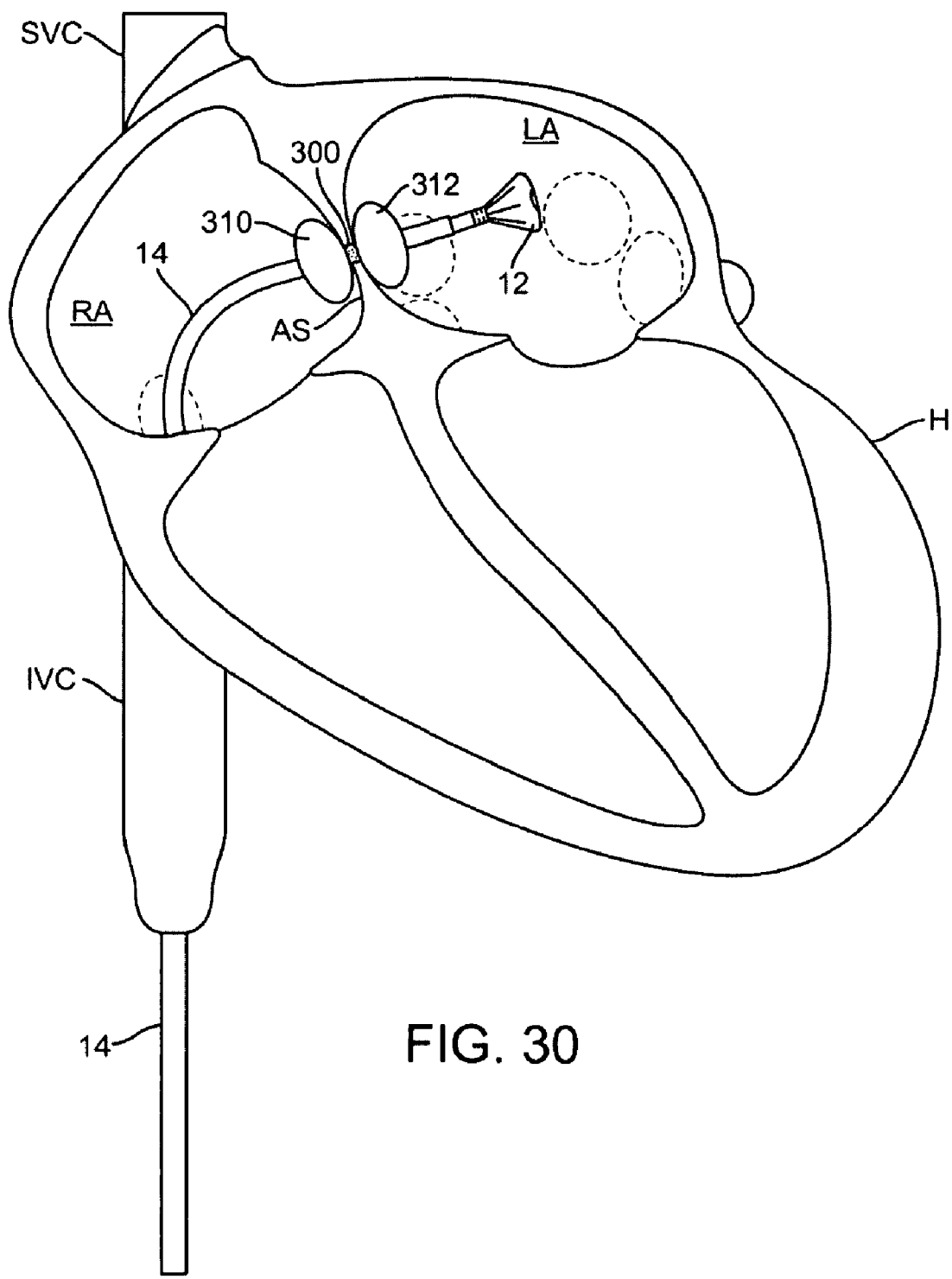
FIG. 30 illustrates a visualization catheter positioned transseptally within a left atrium where a return electrode is positioned along the sheath proximate to the atrial septum.

FIG. 30 illustrates one example of use in a patient heart H where the electrode 300, positioned in this example along outer sheath 14, may be positioned adjacent or proximate to the atrial septum AS with the hood 12 extending through the atrial septum AS and into the left atrium LA. The device may be advanced intravascularly, e.g., through the inferior vena cava IVC and the right atrium RA. The superior vena cava SVC is also illustrated for reference. A position of the electrode 300 may be optionally maintained relative to the atrial septum AS via one or more stabilizing balloons 310, 312 inflated on one or both sides of the septum. Electrode 300 may thus serve as a return electrode for ablation via an electrode positioned within or along hood 12, as previously described.

Figure 31:
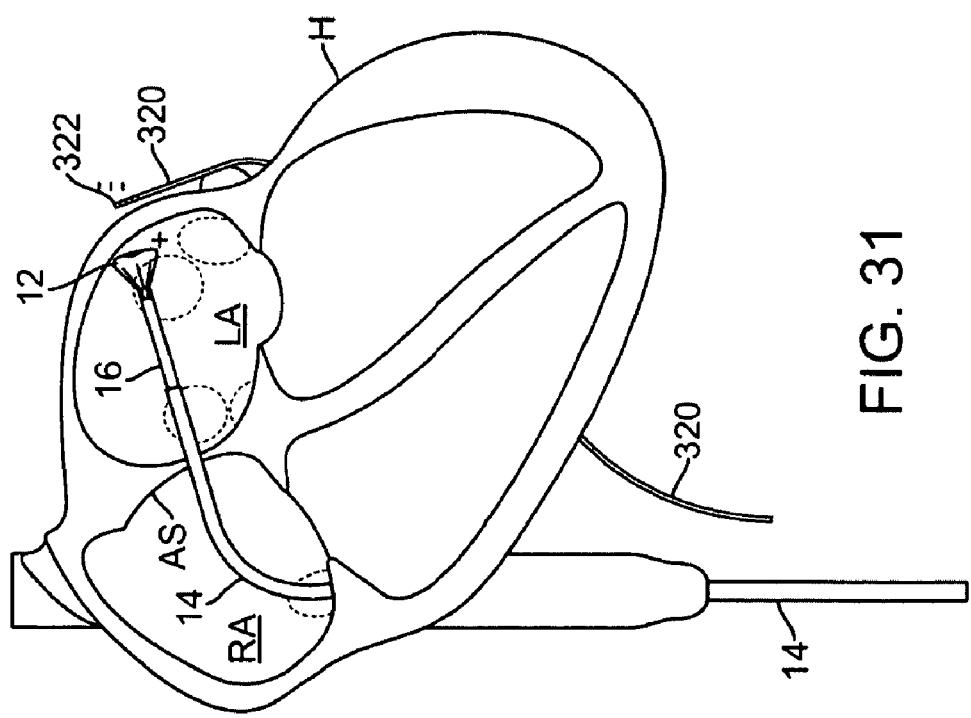
FIG. 31 illustrates a visualization catheter where a return electrode is positioned external to the atrial chamber along an epicardial surface.

In the example shown in FIG. 31, hood 12 may be advanced within the patient heart H as previously described, yet an electrode catheter 320 having a return electrode 322 positioned therealong may be advanced as an instrument separate from the visualization assembly and positioned in proximity to the hood 12. In this example, return electrode 322 may be placed along an external surface of the patient heart H, e.g., along the epicardial wall via a thoracotomy or through a vessel within the heart in proximity to the ablation site, such as through the coronary sinus, pulmonary artery, superior vena cava, inferior vena cava, etc.

Figure 32:
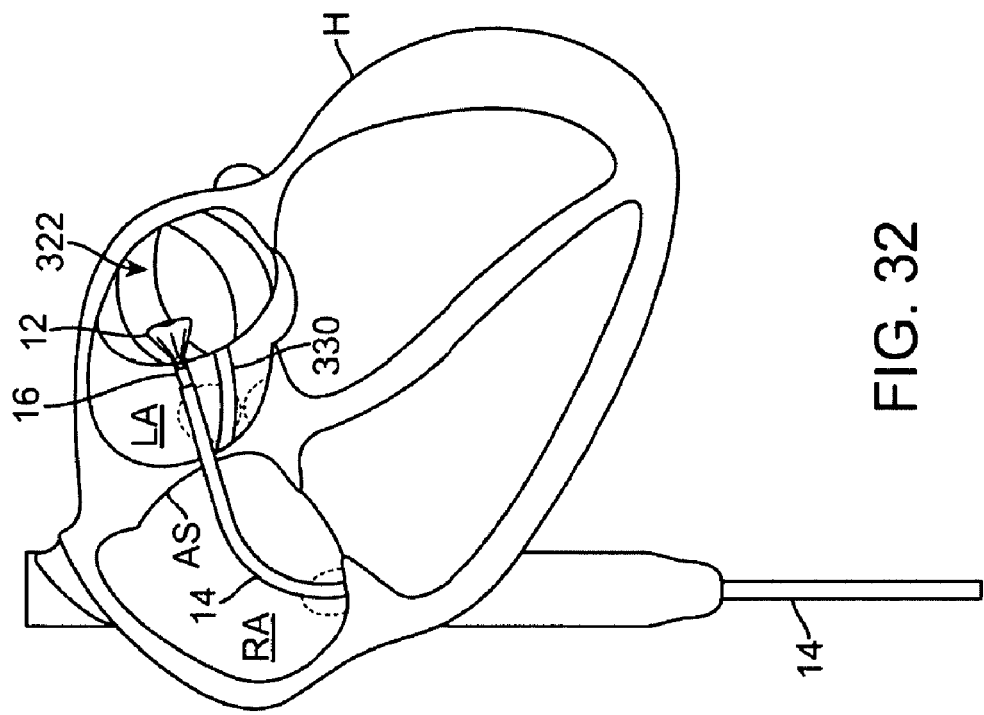
FIG. 32 illustrates a visualization catheter where a return electrode may be configured as a basket deployed in proximity to the hood.

FIG. 32 shows another example where the hood 12 may be positioned, e.g., within the left atrium LA as previously described but with a return electrode 332 positioned intravascularly via a separate electrode catheter 330 such that the return electrode 332 is positioned endocardially. The return electrode 332 may take the shape, in one example, of a shape memory expandable basket with a plurality of electrodes forming the frame of the basket, as shown. This electrode basket can be made from a conductive material such as gold or silver-coated Nitinol.

In yet another variation, FIG. 33A shows a partial cross-sectional side view of a visualization and ablation instrument which utilizes an inflatable balloon 340 which may capacitively couple through balloon 340, which may comprise a transparent, electrically conductive, and non-porous shell which may contact against the tissue to be visualized and ablated. The balloon may be fabricated from materials such as indium-tin oxide, elastomers embedded with carbon nanotubes, or translucent firms with gold, silver or platinum coatings manufactured by the Spi-Met™ process (Spire Medical Inc.). As previously described, balloon 340 may be inflated by a transparent electrically conductive fluid, such as saline, from a collapsed configuration to an expanded configuration. A conducting electrode 342 may be positioned within the balloon 340 and an imaging element 34 may also be positioned within the balloon 340. In use, the current conducted from the electrode 342 and carried through the saline fluid may couple via ionic transport through the saline and the balloon 340 to capacitively couple to the contacted tissue for ablation. FIG. 33B illustrates a schematic 344 of the capacitive coupling which occurs to ablate the tissue where the resistance through the fluid and balloon 340 ($R_{PATH}$) may couple capacitively couple (C) to the tissue ($R_{TISSUE}$).

Another variation is illustrated in the perspective views of FIGS. 34A and 34B which illustrate an expandable balloon 350 having imaging element 34 positioned within and surrounded by multiple inflatable balloons 352 which are also contained within the expandable balloon 350. By the manipulating the pressure within the smaller balloons 352, the imaging element 34 can be articulated to move its field of view 354 to different regions of the ablation site. The internal balloons used in this variation can be made from transparent elastomeric materials to permit visualization through the imaging element 34. Further examples of variable balloon inflation for controlling an instrument is described in further detail in 11/775,837 filed Jul. 10, 2007, which has been incorporated herein in its entirety.

In yet another variation, the tissue visualization and ablation system may be configured as an end effector assembly which may be attachable or coupled to any number of other instruments. An example is shown in the assembly view of FIG. 35A, which shows hood 12 having imaging element 34 self-contained as a separate assembly with a wire and/or connector 364 bundle leading to an imaging element processor and/or display 372 via imaging element wires 366 and a purging fluid reservoir 374 via irrigation channel 368. A hood attachment 360 (e.g., elastic band) may be attached to a proximal end of hood 12 which allows the assembly to be attached to another instrument, such as an articulatable ablation probe 370. FIG. 35B shows an assembled view where the hood assembly may be coupled to ablation probe 370 via attachment 360 such that the distal tip of probe 370 extends within and optionally beyond hood 12. Wire and/or connector bundle 364 may be attached to probe 370 along its length via one or more connectors or attachment bands 376 such that the ablation probe may be advanced along with the hood assembly. Hood 12 may also optionally define a rapid exchange port 362 through which a guidewire 378 may be passed to facilitate use and advancement of the instrument within the patient body. Further details and examples of rapid exchange ports 362 and their methods of use are described in Ser. No. 11/961, 950 filed Dec. 20, 2007, which is incorporated herein by reference in its entirety. In use, hood 12 may be utilized, as previously described for visualization, while its positioning and control may be provided by the ablation probe 370.

Figure 36A:
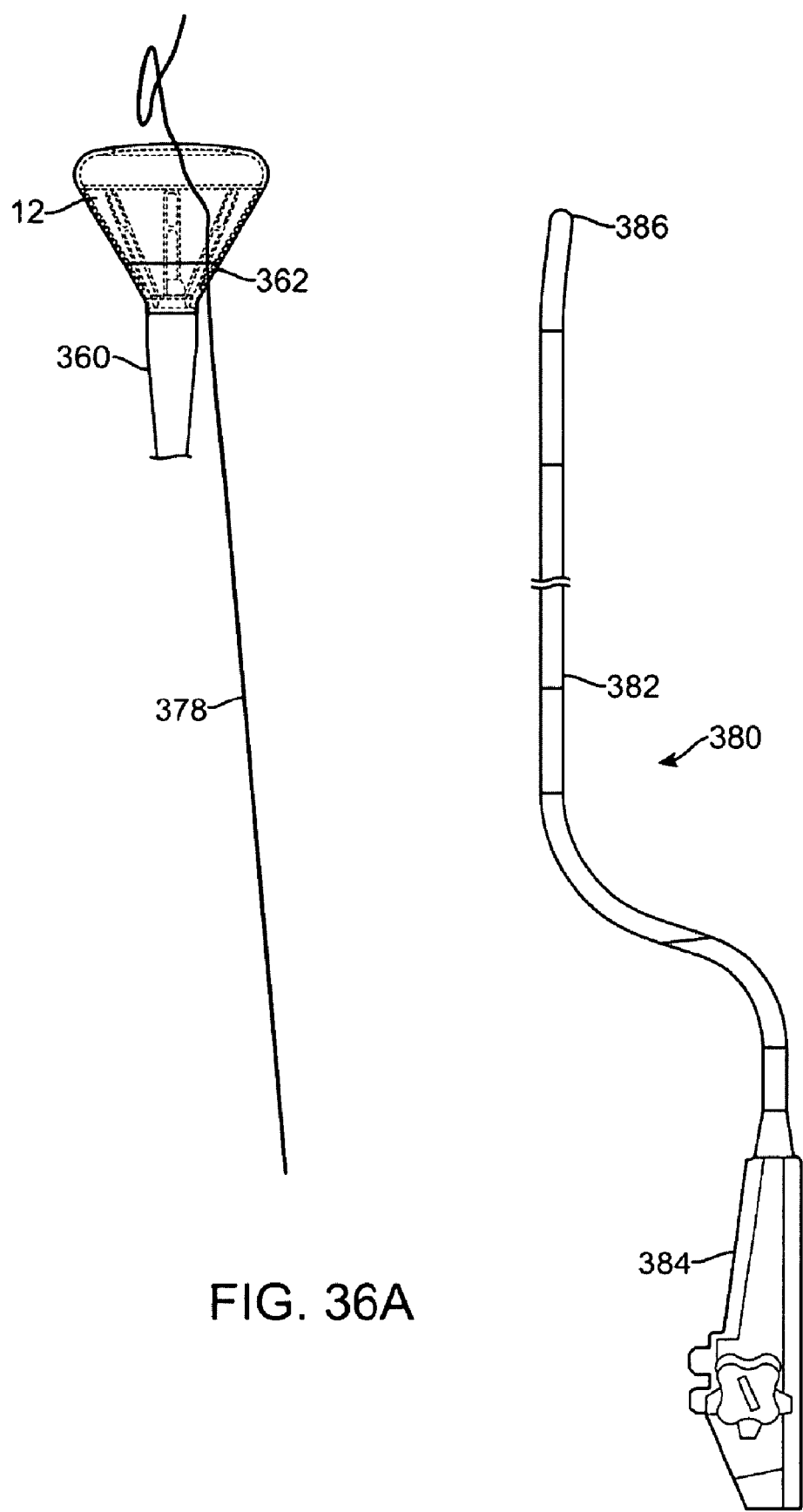
FIG. 36A shows a representative assembly view of another variation where a removably attachable imaging and ablation system may be coupled to an endoscope.
Figure 36B:
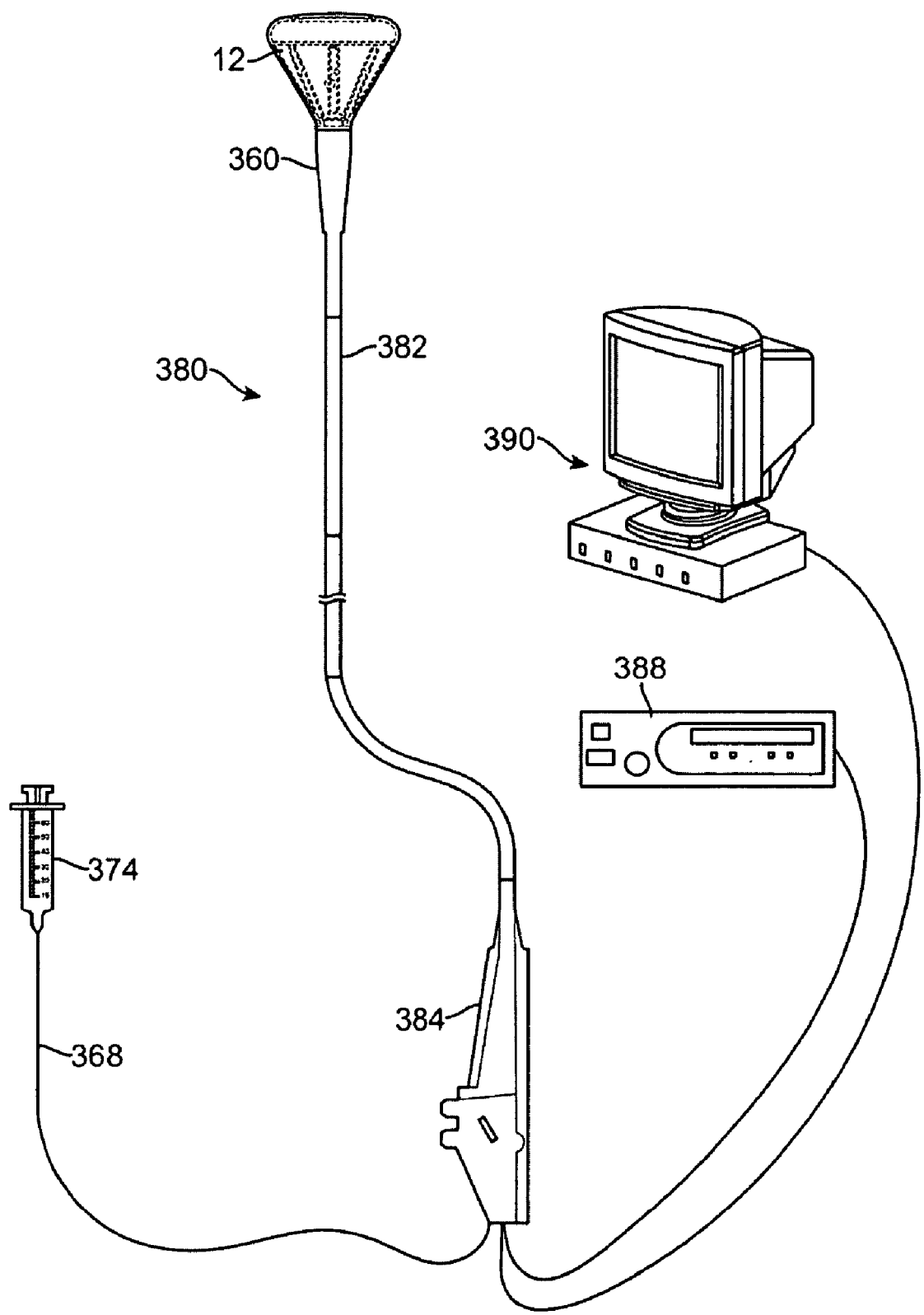
FIGS. 36B and 36C show an example of the assembled imaging and ablation system and the system utilized to visualize and ablate underlying tissue, respectively.

Another variation is shown in the pre-assembly side view of FIG. 36A and the assembled view of FIG. 36B which show a hood assembly, as described above, which may be incorporated with other instruments such as an endoscope 380 which may have an articulatable distal end 386 coupled to a handle 384 via shaft 382. The imaging hood assembly can be attached to the endoscope 380 by having attachment 360 affixed to the distal end 386 of the endoscope 380, e.g., via usage of elastic bands, clamps, screws threads, slip-fit components, adhesive, sleeve couplers, etc. Saline or other transparent/translucent electrically conductive fluid, can be purged through the working channel of the endoscope 380. Other instruments (e.g., energy delivery probes, graspers, guidewires, ablation catheters, etc.) can also be advanced into the imaging hood via the working channel of the endoscope 380. Additionally, power generator 388 may provided for generating the ablation energy as well as an image processor and/or display 390 for viewing images either from an imaging element contained within or along hood 12 and/or as provided directly by the endoscope 380. The rapid exchange port 362 defined along hood 12 can additionally serve as an alternative path for instruments which may not be able to be passed through the working lumens of the endoscope 380, e.g., due to limited size of the lumen channel or the number of channels the endoscope can provide.

Figure 36C:
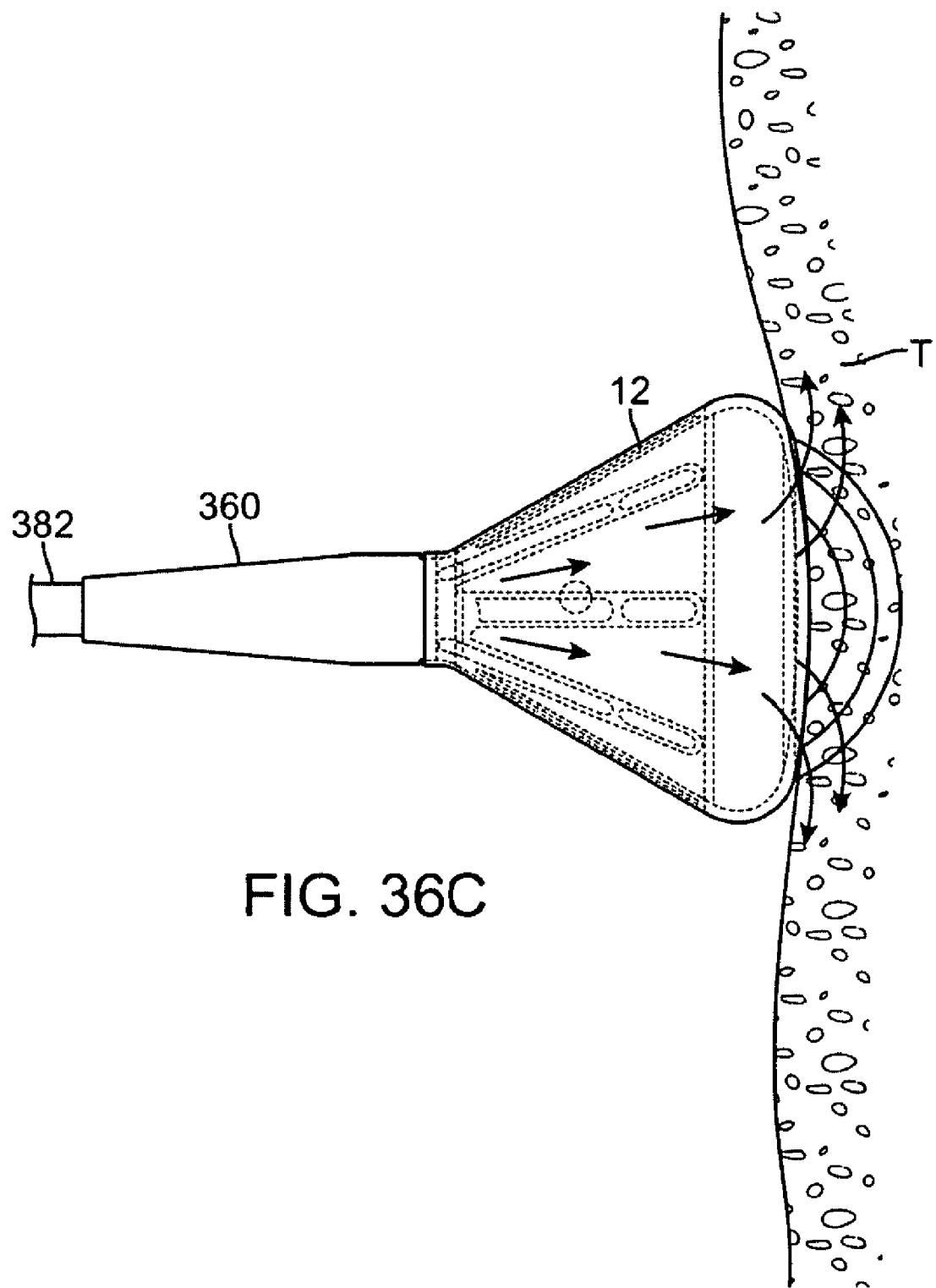

FIG. 36C shows a side view of the hood assembly positioned against a tissue region to be visualized and treated. Any number of energy modalities may be utilized for ablating the underlying tissue (such as RF, cryo, laser, HIFU or other forms of energy) through the lumen of the endoscope 380 while under direct visualization. Alternatively, an energy delivery probe may be passed through the working channels of the endoscope 380 and brought in contact with the saline inside the hood 12 to deliver RF ablation energy through the fluid, as previously described.

Figure 37A:
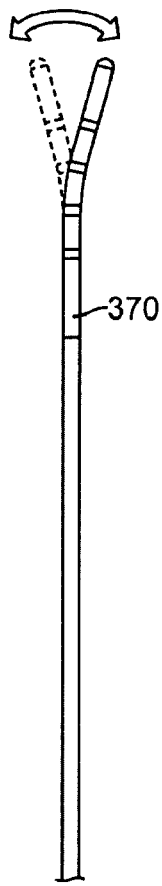
FIGS. 37A and 37B show side views of an articulatable ablation catheter and a tissue visualization catheter, respectively, which may be passively articulated.
Figure 37B:
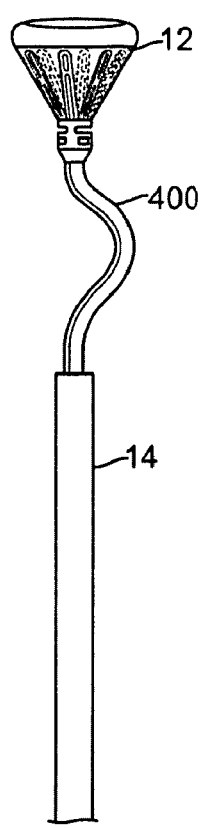
Figure 37C:
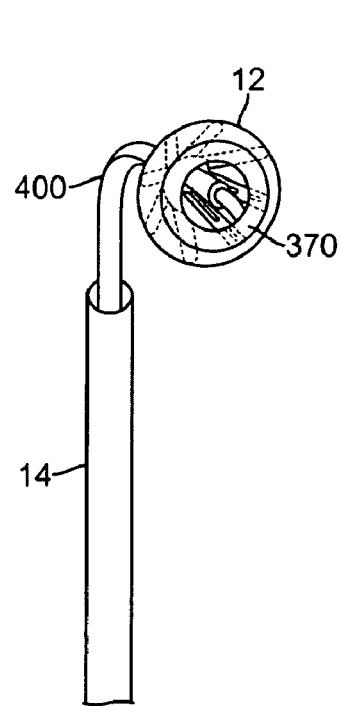
FIGS. 37C and 37D show perspective views of the tissue visualization catheter passively steered by the ablation catheter positioned therethrough.
Figure 37D:
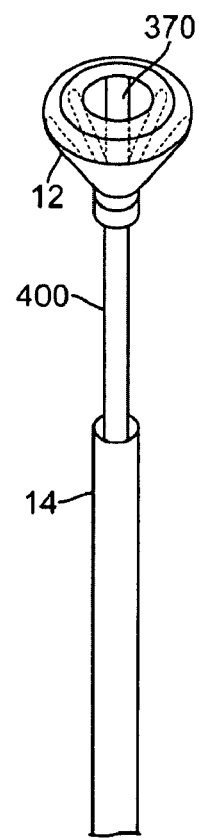

In yet another variation, an articulatable ablation probe 370, as shown in FIG. 37A, may be incorporated in a deployment catheter 400 having a flexible shaft and hood 12 positioned thereupon, as shown in FIG. 37B. The flexible segment can be constructed from relatively low durometer and/or transparent polymers such as silicone or thin-walled polyurethanes. Alternatively, the flexible segment can be constructed by wire frames with struts longitudinally arranged by thin wires (e.g., approximately 0.005" to 0.015") such as Nitinol, stainless stain, Elgiloy®, tungsten, etc. where the wire frame may be circumferentially covered/sealed by a membrane or heat shrink material such as polyester (as available from Advance Polymer Inc), latex, etc. The ablation probe 370 may be introduced through the passively steerable flexible shaft of catheter 400 such that articulation of the ablation probe 370 may be utilized to articulate a position of the hood 12, as illustrated in the perspective views of FIGS. 37C and 37D.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure.

Moreover, various combinations of aspects between examples are also contemplated and are considered to be within the scope of this disclosure as well.

What is claimed is:

1. A tissue treatment system, comprising:
    a reconfigurable and non-inflating hood structure having an attachment member and which is capable of intravascular delivery in a low profile delivery configuration and expansion to a deployed configuration which defines an open area bounded at least in part by the hood structure;
    a fluid lumen in communication with the open area of the hood structure such that introduction of a conductive fluid through the lumen purges the open area of blood when the structure is further bounded by a tissue surface, wherein the open area is in fluid communication with an environment external to the hood structure through an opening defined by the hood structure; and
    an instrument removably attachable to the hood structure via the attachment member such that a position of the hood structure is maintained relative to the instrument.

2. The system of claim 1 further comprising an imaging element within or along the structure such that the open area is contained within a visual field of the imaging element.

3. The system of claim 1 wherein the hood structure comprises a distal membrane which defines an aperture.

4. The system of claim 1 wherein the fluid lumen is positionable within or along the instrument.

5. The system of claim 1 further comprising a deployment catheter having a flexible shaft through which the instrument is positioned.

6. The system of claim 1 wherein the instrument comprises an ablation probe.

7. The system of claim 6 wherein the ablation probe is articulatable.

8. The system of claim 1 wherein the instrument comprises an endoscope having an articulatable distal end.

9. A tissue treatment system, comprising:
    a reconfigurable and non-inflating hood structure having a flexible shaft and which is capable of intravascular delivery in a low profile delivery configuration and expansion to a deployed configuration which defines an open area bounded at least in part by the structure;
    a fluid lumen in communication with the open area of the hood structure such that introduction of a conductive fluid through the lumen purges the open area of blood when the structure is further bounded by a tissue surface, wherein the open area is in fluid communication with an environment external to the hood structure through an opening defined by the hood structure; and
    an instrument removably positionable through the flexible shaft such that the hood structure is steerable via articulation of the instrument.

10. The system of claim 9 further comprising an imaging element within or along the structure such that the open area is contained within a visual field of the imaging element.

11. The system of claim 9 wherein the hood structure comprises a distal membrane which defines an aperture.

12. The system of claim 9 wherein the fluid lumen is positionable within or along the instrument.

13. The system of claim 9 wherein the instrument comprises an ablation probe.

14. The system of claim 13 wherein the ablation probe is articulatable.

15. The system of claim 9 wherein the instrument comprises an endoscope having an articulatable distal end.

* * * * *